United States Patent
Klinger et al.

(10) Patent No.: US 12,351,872 B2
(45) Date of Patent: *Jul. 8, 2025

(54) DETERMINING ANTIGEN-SPECIFIC T-CELLS

(71) Applicant: Adaptive Biotechnologies Corporation, Seattle, WA (US)

(72) Inventors: Mark Klinger, Seattle, WA (US); Malek Faham, Seattle, WA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 586 days.

This patent is subject to a terminal disclaimer.

(21) Appl. No.: 17/579,900

(22) Filed: Jan. 20, 2022

(65) Prior Publication Data

US 2022/0251653 A1 Aug. 11, 2022

Related U.S. Application Data

(60) Continuation of application No. 16/106,867, filed on Aug. 21, 2018, now Pat. No. 11,261,490, which is a division of application No. 14/242,520, filed on Apr. 1, 2014, now Pat. No. 10,066,265.

(51) Int. Cl.
*C12Q 1/6881* (2018.01)

(52) U.S. Cl.
CPC ..... *C12Q 1/6881* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,189,147 A | 2/1993 | Saito et al. |
| 5,213,960 A | 5/1993 | Chang |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,418,134 A | 5/1995 | Morley |
| 5,506,126 A | 4/1996 | Seed et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,925,517 A | 7/1999 | Tyagi et al. |
| 5,935,793 A | 8/1999 | Wong |
| 5,981,176 A | 11/1999 | Wallace |
| 6,087,096 A | 7/2000 | Dau et al. |
| 6,091,000 A | 7/2000 | Haynes |
| 6,136,566 A | 10/2000 | Sands et al. |
| 6,172,214 B1 | 1/2001 | Brenner |
| 6,207,371 B1 | 3/2001 | Zambrowicz et al. |
| 6,214,613 B1 | 4/2001 | Higuchi et al. |
| 6,228,589 B1 | 5/2001 | Brenner |
| 6,255,071 B1 | 7/2001 | Beach et al. |
| 6,258,568 B1 | 7/2001 | Nyren |
| 6,291,183 B1 | 9/2001 | Pirrung et al. |
| 6,300,065 B1 | 10/2001 | Kieke et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,423,538 B1 | 7/2002 | Wittrup et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |

(Continued)

FOREIGN PATENT DOCUMENTS

| | | |
|---|---|---|
| CN | 101225441 A | 7/2008 |
| CN | 102272327 A | 12/2011 |

(Continued)

OTHER PUBLICATIONS

US 6,331,391 B1, 12/2001, Wittrup et al. (withdrawn)
Kim (Plos One vol. 7 Issue 5 e37338 May 23, 2012).*
Klinger (Plos One vol. 8 Issue 9 e74231 Sep. 19, 2013).*
Aird, et al., "Analyzing and minimizing PCR amplification bias in Illumina sequencing libraries." Genome Biology (2011); 12: R18, pp. 1-14.
Akamatsu, Y. et al., "Essential Residues in V(D)J Recombination Signals." The Journal of Immunology (1994); 153 (10): 4520-4529.
Barbas III, et al., "Assembly of combinatorial antibody libraries on phage surfaces: the gene III site." Proc Natl Acad Sci U S A. (Sep. 1991); 88(18): 7978-7982.
Barnard, et al., "PCR Bias Toward the Wild-Type k-rasand p53 Sequences: Implications for PCR Detection of Mutations and Cancer Diagnosis." BioTechniques (Oct. 1998); 25: 684-691.

(Continued)

*Primary Examiner* — Amanda Haney
(74) *Attorney, Agent, or Firm* — Shweta Chandra; Bozicevic, Field & Francis LLP

(57) ABSTRACT

The invention is directed to methods for determining antigen-specific T cells. In some embodiments, methods of the inven-tion may be implemented by the steps of reacting under interaction conditions one or more antigens with T cells in a plurality of subsets of a tissue sample, such as peripheral blood; sorting antigen-interacting T cells from other T cells; separately sequencing for each subset recombined nucleic acid encoding a segment of a TCR chain from a sample of T cells prior to exposure to antigen and from a sample off cells isolated based on their interaction with antigen, thereby form-ing a clonotype profile for the former sample and the latter sample for each subset; and identifying as antigen-specific T cells those T cells associated with a clonotype whose fre-quency increases in the latter sample relative to its frequency in the former sample.

19 Claims, 15 Drawing Sheets

(56) References Cited

U.S. PATENT DOCUMENTS

| | | |
|---|---|---|
| 6,524,829 B1 | 2/2003 | Seegar |
| 6,569,627 B2 | 5/2003 | Wittwer et al. |
| 6,596,492 B2 | 7/2003 | Avery et al. |
| 6,753,147 B2 | 6/2004 | Vogelstein et al. |
| 6,787,308 B2 | 9/2004 | Balasubramanian et al. |
| 6,919,434 B1 | 7/2005 | Goto et al. |
| 6,964,850 B2 | 11/2005 | Bevilacqua |
| 6,969,597 B2 | 11/2005 | Lukyanov et al. |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 * | 1/2016 | Faham ............... C12N 15/1072 |
| 9,279,159 B2 | 3/2016 | Robins et al. |
| 9,371,558 B2 | 6/2016 | Robins et al. |
| 9,394,567 B2 | 7/2016 | Asbury et al. |
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 10,066,265 B2 | 9/2018 | Klinger et al. |
| 10,077,473 B2 | 9/2018 | Asbury et al. |
| 10,077,478 B2 | 9/2018 | Faham et al. |
| 10,150,996 B2 | 12/2018 | Robins et al. |
| 10,155,992 B2 | 12/2018 | Faham et al. |
| 10,214,770 B2 | 2/2019 | Robins et al. |
| 10,246,701 B2 | 4/2019 | Dewitt et al. |
| 10,246,752 B2 | 4/2019 | Faham et al. |
| 10,266,901 B2 | 4/2019 | Faham et al. |
| 10,323,276 B2 | 6/2019 | Wiley |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | Macevicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0275752 A1 | 7/2006 | Sindhi |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |

(56) References Cited

U.S. PATENT DOCUMENTS

| | | |
|---|---|---|
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1* | 8/2011 | Faham ............... C12Q 1/6883 435/6.11 |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0220494 A1 | 8/2012 | Samuels et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham et al. |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1* | 12/2014 | Faham ............... C12Q 1/6869 435/6.12 |
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Li et al. |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0024493 A1 | 1/2016 | Robins et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |

(56) References Cited

U.S. PATENT DOCUMENTS

| | | |
|---|---|---|
| 2016/0251721 A1 | 9/2016 | Robins et al. |
| 2016/0251728 A1 | 9/2016 | Faham et al. |
| 2016/0258025 A1 | 9/2016 | Klinger et al. |
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0023143 A9 | 1/2018 | Faham et al. |
| 2018/0037953 A1 | 2/2018 | Emerson et al. |
| 2018/0073015 A1 | 3/2018 | Robins et al. |
| 2018/0080078 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |
| 2018/0312832 A1 | 11/2018 | Robins et al. |
| 2018/0355429 A1 | 12/2018 | Klinger et al. |
| 2019/0040462 A1 | 2/2019 | Asbury et al. |
| 2019/0062848 A1 | 2/2019 | Faham et al. |
| 2019/0100810 A1 | 4/2019 | Faham et al. |

FOREIGN PATENT DOCUMENTS

| | | |
|---|---|---|
| CN | 103097888 A | 5/2013 |
| EA | 007958 B1 | 2/2007 |
| EP | 0303459 A2 | 2/1989 |
| EP | 0799897 A1 | 10/1997 |
| EP | 1516929 A2 | 3/2005 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088205 A1 | 8/2009 |
| EP | 2088432 A1 | 8/2009 |
| EP | 2418287 A2 | 2/2012 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2011-505123 A | 2/2011 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013868 A1 | 4/1997 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2001/014424 A2 | 3/2001 |
| WO | WO 2002/024322 A2 | 3/2002 |
| WO | WO 2003/008624 A2 | 1/2003 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/010200 A2 | 2/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/083456 A1 | 7/2010 |
| WO | WO 2010/151416 A1 | 12/2010 |
| WO | WO 2011/017151 A2 | 2/2011 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A1 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |

(56) References Cited

FOREIGN PATENT DOCUMENTS

| WO | WO 2013/169957 A1 | 11/2013 |
|---|---|---|
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |
| WO | WO 2016/138122 A1 | 9/2016 |
| WO | WO 2016/161273 A1 | 10/2016 |

OTHER PUBLICATIONS

Bessette, et al., "Rapid isolation of high-affinity protein binding peptides using bacterial display." Protein Engineering, Design and Selection (Oct. 2004); 17(10): 731-739.
Bhatia, et al., "Rolling Adhesion Kinematics of Yeast Engineered to Express Selectins." Biotechnology Progress (2003); 19(3): 1033-1037.
Bidwell, "Advances in DNA-based HLA-typing methods." Immunol Today (Jul. 1994); 15 (7): 303-307.
Boder and Wittrup, "Yeast surface display for screening combinatorial polypeptide libraries." Nat Biotechnol. (Jun. 1997); 15(6): 553-557.
Boulware and Daugherty, "Protease specificity determination by using cellular libraries of peptide substrates (CLiPS)." PNAS (May 2006); 103 (20): 7583-7588.
Bradbury, et al., "Use of Living cols. to Select Specific Phage Antibodies." BioTechnology (1993); 11: 1565-1568.
Bupp and Roth, "Altering retroviral tropism using a random-display envelope library." Mol Ther. (Mar. 2002); 5(3): 329-335.
Charbit, et al., "Versatility of a vector for expressing foreign polypeptides at the surface of Gram-negative bacteria." Gene (1988); 70(1): 181-189.
Chestnut, et al., "Selective isolation of transiently transfected cells from a mammalian cell population with vectors expressing a membrane anchored single-chain antibody." J Immunol Methods. (Jun. 1996); 193(1): 17-27.
Chou, et al., "Expression of Chimeric Monomer and Dimer Proteins on the Plasma Membrane of Mammalian Cells." Biotechnol Bioeng (Oct. 1999); 65(2): 160-169.
Dane, et al., "Isolation of cell specific peptide ligands using fluorescent bacterial display libraries." J Immunol Methods. (Feb. 2006); 309(1-2): 120-129. Epub Jan. 11, 2006.
Daugherty, et al., "Quantitative analysis of the effect of the mutation frequency on the affinity maturation of single chain Fv antibodies." PNAS (Feb. 2000); 97 (5): 2029-2034.
Day, et al., "Identification of non-amplifying CYP21 genes when using PCR-based diagnosis of 21-hydroxylase deficiency in congenital adrenal hyperplasia (CAH) affected pedigrees." Hum Mol Genet. (Dec. 1996); 5(12): 2039-2048.
De Cárcer, et al., "Strategy for Modular Tagged High-Throughput Amplicon Sequencing." Applied and Environmental Microbiology (Sep. 2011); 77(17): 6310-6312.
DeWitt, et al., "Dynamics of the Cytotoxic T Cell Response to a Model of Acute Viral Infection." J. Virol. (Apr. 2015); 89 (8): 4517-4526. Epub Feb. 4, 2015.
Dziubianau, M., et al., "TCR repertoire analysis by next generation sequencing allows complex differential diagnosis of T cell-related pathology." Am J Transplant (Nov. 2013); 13(11): 2842-2854. doi: 10.1111/ajt.12431. Epub Sep. 10, 2013.
Efron and Thisted, "Estimating the number of unseen species: How many words did Shakespeare know?" Biometrika (1976); 63(3): 435-447.
European Patent Application No. 16756268.5, Extended European Search Report dated Oct. 22, 2018, 20 pages.
European Patent Application No. 16756268.5, Partial Supplementary European Search Report dated Jun. 19, 2018, 21 pages.
European Patent Application No. 16774304.6, Extended European Search Report dated Oct. 15, 2018, 9 pages.
European Patent Application No. 18153536.0, Extended European Search Report dated Jun. 6, 2018, 7 pages.
European Patent Application No. 18184843.3, Extended European Search Report dated Aug. 13, 2018, 10 pages.
European Patent Application No. 18211168.2, Extended European Search Report dated Jan. 31, 2019, 6 pages.
Fanning, et al., "Development of the immunoglobulin repertoire." Clin Immunol Immunopathol. (Apr. 1996); 79(1): 1-14.
Feldhaus, et al., "Flow-cytometric isolation of human antibodies from a nonimmune *Saccharomyces cerevisiae* surface display library." Nat Biotechnol. (Feb. 2003); 21(2): 163-70. Epub Jan. 21, 2003.
Han, et al., "Linking T-cell receptor sequence to functional phenotype at the single-cell level." Nat Biotechnol. (2014); 32 (7): 684-692. Epub Jun. 22, 2014.
Hanes and Plückthun, "In vitro selection and evolution of functional proteins by using ribosome display." Proc Natl Acad Sci U S A. (May 1997); 94(10): 4937-4942.
Hedegaard and Klemm, "Type 1 fimbriae of *Escherichia coli* as carriers of heterologous antigenic sequences." Gene (Dec. 1989); 85(1): 115-124.
Hesse, et al., "V(D)J recombination: a functional definition of the joining signals." Genes Dev. (Jul. 1989); 3(7): 1053-1061.
Hofnung, M., "Chapter 4 Expression of Foreign Polypeptides at the *Escherichia coli* Cell Surface." Methods in Cell Biology (1991); 34: 77-105.
Holmes and Al-Rubeai, "Improved cell line development by a high throughput affinity capture surface display technique to select for high secretors." J Immunol Methods. (Nov. 1999); 230(1-2): 141-147.
Kanagawa, T., "Bias and artifacts in multitemplate polymerase chain reactions (PCR)." J Biosci Bioeng. (2003); 96(4): 317-323.
Klauser, et al., "Extracellular transport of cholera toxin B subunit using Neisseria IgA protease beta-domain: conformation-dependent outer membrane translocation." The EMBO Journal (Jun. 1990); 9(6): 1991-1999.
Larijani, et al., "The role of components of recombination signal sequences in immunoglobulin gene segment usage: a V81x model." Nucleic Acids Research (Jan. 1999); 27(11): 2304-2309.
Lee, et al., "A Functional Analysis of the Spacer of V(D)J Recombination Signal Sequences." PLoS Biology (2003); 1(1): e1, pp. 056-059.
Linnemann, et al., "High-throughput identification of antigen-specific TCRs by TCR gene capture." Nature Medicine (Nov. 2013); 19 (11): 1534-1541. Epub Oct. 13, 2013.
Linnemann, et al., "TCR repertoires of intratumoral T-cell subsets." Immunological Reviews (2014); 257 (1): 72-82.
López-Pérez, R., et al., "Gene scanning of VDJH-amplified segments is a clinically relevant technique to detect contaminating tumor cells in the apheresis products of multiple myeloma patients undergoing autologous peripheral blood stem cell transplantation." Bone Marrow Transplantation (2001); 28(7): 665-72.
Lossius, et al., "High-throughput sequencing of TCR repertoires in multiple sclerosis reveals intrathecal enrichment of EBV-reactive CD8+ T cells." European Journal of Immunology (Nov. 2014); 44 (11): 3439-3452. Epub Sep. 16, 2014.
Lu, et al., "Expression of thioredoxin random peptide libraries on the *Escherichia coli* cell surface as functional fusions to flagellin: a system designed for exploring protein-protein interactions." Biotechnology (N Y). (Apr. 1995); 13(4): 366-372.
McCafferty, et al., "Phage antibodies: filamentous phage displaying antibody variable domains." Nature (Dec. 1990); 348(6301): 552-554.

(56) References Cited

OTHER PUBLICATIONS

Miqueu, P., et al., "Analysis of the peripheral T-cell repertoire in kidney transplant patients." Eur J Immunol. (Nov. 2010); 40(11): 3280-3290. Epub Oct. 27, 2010.
Müller, et al., "Random peptide libraries displayed on adeno-associated virus to select for targeted gene therapy vectors." Nat Biotechnol. (Sep. 2003); 21(9): 1040-1046. Epub Aug. 3, 2003.
Nadel, et al., "Decreased Frequency of Rearrangement due to the Synergistic Effect of Nucleotide Changes in the Heptamer and Nonamer of the Recombination Signal Sequence of the Vκ Gene A2b, Which Is Associated with Increased Susceptibility of Navajos to Haemophilus influenzae Type b Disease." The Journal of Immunology (1998); 161(11): 6068-6073.
Nadel, et al., "Sequence of the Spacer in the Recombination Signal Sequence Affects V(D)J Rearrangement Frequency and Correlates with Nonrandom Vκ Usage In Vivo." Jornal of Experimental Medicine (1998); 187 (9): 1495-1503.
Nakajima, et al., "Expression of random peptide fused to invasin on bacterial cell surface for selection of cell-targeting peptides." Gene (Dec. 2000); 260 (1-2): 121-131.
Newton, et al., "Immune response to cholera toxin epitope inserted in *Salmonella flagellin*." Science (Apr. 1989); 244(4900): 70-72.
Ogino and Wilson., "Quantification of PCR Bias Caused by a Single Nucleotide Polymorphism in SMN Gene Dosage Analysis." The Journal of Molecular Diagnostics (Nov. 2002); 4(4): 185-190.
Qu, et al., "Efficient frequency-based de novo short-read clustering for error trimming in next-generation sequencing." Genome Research (2009), 19(7): 1309-1315.
Ramsden, et al., "Conservation of sequence in recombination signal sequence spacers." Nucleic Acids Res. (May 1994); 22(10): 1785-1796.
Roh, et al., "Comparing microarrays and next-generation sequencing technologies for microbial ecology research." Trends Biotechnol. (Jun. 2010); 28(6): 291-299. Epub Apr. 8, 2010.
Seder and Ahmed, "Similarities and differences in CD4+ and CD8+effector and memory T cell generation." Nat Immunol. (2003); 4 (9): 835-842.
Smith, G.P., "Filamentous fusion phage: novel expression vectors that display cloned antigens on the virion surface." Science (Jun. 1985); 228(4705): 1315-1317.
Spellman, et al., "Advances in the selection of HLA-compatible donors: refinements in HLA typing and matching over the first 20 years of the National Marrow Donor Program Registry." Biol Blood Marrow Transplant (2008); (9 Suppl): 37-44. Epub Jun. 20, 2008.
Theberge, et al., "Microdroplets in Microfluidics: An Evolving Platform for Discoveries in Chemistry and Biology." Angew Chem Int Ed Engl. (Aug. 9, 2010); 49(34): 5846-5868.
Wilson, et al., "The use of mRNA display to select high-affinity protein-binding peptides." PNAS (Mar. 2001); 98 (7): 3750-3755.
Wittrup, "Protein engineering by cell-surface display." Current Opinion in Biotechnology (Aug. 2001); 12(4): 395-399.
Yonezawa, et al., "DNA display for in vitro selection of diverse peptide libraries." Nucleic Acids Res. (Oct. 2003); 31(19): e118.
Zeng, et al., "Electrical Control of Individual Droplet Breaking and Droplet Contents Extraction." Anal. Chem. (2011); 83 (6): 2083-2089.
Zwick, et al., "Identification and Characterization of a Peptide That Specifically Binds the Human, Broadly Neutralizing Anti-Human Immunodeficiency Virus Type 1 Antibody b12." Journal of Virology (Jul. 2001); 75(14): 6692-6699.
US 8,642,750, 02/2014, Faham et al. (withdrawn).
Abbott, et al. "Design and use of signature primers to detect carry-over of amplified material", J Virol Methods, 46(1):51-59, Abstract Only (1994).
Ahmadzadeh et al. "FOXP3 expression accurately defines the population of intratumoral regulatory T cells that selectively accumulate in metastatic melanoma lesions", *Blood*, 112(13): 4953-4960 (2008).

Akatsuka, Y. et al., "Rapid screening of T-cell receptor (TCR) variable gene usage by multiplex PCR: Application for assessment of clonal composition", *Tissue Antigens*, 53(2):122-134 (1999).
Alatrakchi et al. "T-cell clonal expansion in patients with B-cell lymphoproliferative disorders", *Journal of Immunotherapy*, 21(5): 363-370 (1998).
Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.
Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.
Altman, et al. "Phenotypic analysis of antigen-specific T lymphocytes", The *Journal of Immunology*, 187(1):7-9 (2011).
Andreasson, et al. "The human IgE-encoding transcriptome to assess antibody repertoires and repertoire evolution", *J Mol Biol.*, 362(2):212-227 (2006). Epub Aug. 14, 2006.
Armand, P. et al., "Detection of circulating tumour DNA in patients with aggressive B-cell non-Hodgkin lymphoma", *Brit. J. Haematol.*, vol. 163, pp. 123-126 (2013).
Arstila, T.P., et al., "A direct estimate of the human αβ T cell receptor diversity," Science, 286(5441): 958-961 (1999).
Aslanzadeh. "Preventing PCR amplification carryover contamination in a clinical laboratory", *Ann Clin Lab Sci.*, 34(4): 389-396 (2004).
Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).
Babrzadeh et al. "Development on High-throughput Sequencing Technology: emPCR Titration and Barcode Design", *Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Barker, et al. "A second type II restriction endonuclease from Thermus aquaticus with an unusual sequence specificity", *Nucleic Acids Res.*, 12(14): 5567-5581 (1984).
Baum and McCune et al. "Direct measurement of T-cell receptor repertoire diversity with AmpliCot", *Nat Methods*, 3(11): 895-901 (2006).
Becton-Dickinson T-Cell Research Tools, "Novel multicolor flow cytometry tools for the study of CD4+ T-cell differentiation and plasticity", 16 pages (2009).
Becton-Dickinson, CD marker handbook. bdbiosciences.com/go/mousecdmarkers, p. 1-47 (2010).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).
Béné and Kaeda, "How and why minimal residual disease studies are necessary in leukemia: a review from WP10 and WP12 of the European LeukaemiaNet", *Haematologica*, 94(8):1135-1150 (2009).
Benichou, J. et al., "The restricted DH gene reading frame usage in the expressed human antibody repertoire is selected based upon its amino acid content", J Immunol., 190(11): 5567-77, 29 pages (2013).
Benichou, J. et al., "Rep-Seq: uncovering the immunological repertoire through next-generation sequencing", *Immunology*, 135(3): 183-191 (2011).
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.

(56) References Cited

OTHER PUBLICATIONS

Bernard et al. "Color multiplexing hybridization probes using the apolipoprotein E locus as a model system for genotyping", Anal Biochem., 273(2):221-228 (1999).
Bernardin, F. et al., "Estimate of the total No. of CD8+ clonal expansions In healthy adults using a new DNA heteroduplex-tracking assay for CDR3 repertoire analysis", Journal of Immunological Methods, 274(1-2):159-175 (2003).
Bertness, et al. "T-Cell Receptor Gene Rearrangements as Clinical Markers of Human T-Cell Lymphomas", The New England Journal of Medicine, 313:534-538 (1985).
Biggerstaff, et al. "Enumeration of leukocyte infiltration in solid tumors by confocal laser scanning microscopy", BMC Immunol., 7:16, 13 pages (2006).
Bolotin, D.A. et al., "Next generation sequencing for TCR repertoire profiling: Platform-specific features and correction algorithms", Eur. J. Immunol., 42:3073-3083 (2012).
Bonarius, H.P.J. et al. "Monitoring the T-Cell Receptor Repertoire at Single-Clone Resolution", PLOS One, 1(e55):1-10 (2006).
Boria, et al. "Primer sets for cloning the human repertoire of T cell receptor variable regions", BMC Immunology, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.
Boudinot et al. "New perspectives for large-scale repertoire analysis of immune receptors", Molecular Immunology, 45: 2437-2445 (2008).
Boyce, et al. "Human regulatory T-cell isolation and measurement of function", BD Biosciences, pp. 1-20 (2010).
Boyd, S.D. et al., "Individual Variation in the Germline Ig Gene Repertoire Inferred from Variable Region Gene Rearrangements", The Journal of immunology, 184(12): 6986-6992 (2010). Epub 2010.
Boyd, S.D. et al., "Measurement and Clinical Monitoring of Human Lymphocyte Clonality by Massively Parallel V-D-J Pyrosequencing," Science Translational Medicine, 1:12ra23, 40 pages, including Supplementary Materials (2009).
Bradfield, et al. "Graft-versus-leukemia effect in acute lymphoblastic leukemia: the importance of tumor burden and early detection", Leukemia, 18(6): 1156-1158 (2004).
Brehm-Stecher and Johnson. "Single-cell microbiology: tools, technologies, and applications", Microbiology and Molecular Biology Reviews, 68(3):538-559 (2004).
Brenan, C. et al., "High throughput, nanoliter quantitative PCR," Drug Discovery Today: Technologies, 2(3):247-253 (2005).
Brennan et al. "Predictable αβ T-cell receptor selection toward an HLA-B*3501—restricted human cytomegalovirus epitope", J. Virol., 81(13): 7269-7273 (2007).
Brisco, et al. "Determining the repertoire of IGH gene rearrangements to develop molecular markers for minimal residual disease in B-lineage acute lymphoblastic leukemia", J Mol Diagn., 11(3):194-200 (2009).
Brisco, et al. "Outcome prediction in childhood acute lymphoblastic leukaemia by molecular quantification of residual disease at the end of induction", Lancet, 343:196-200 (1994).
Brochet et al. "IMGT/V-QUEST: the highly customized and integrated system for IG and TR standardized V-J and V-D-J sequence analysis", Nucleic Acids Research, vol. 36, Web Server issue W503-W508 (2008).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", Journal of Clinical Oncology, ASCO Annual Meeting Abstracts Part 1, Suppl; abstr 2509: vol. 29, No. 15, 1 page (2011).

Brüggemann, et al. "Clinical significance of minimal residual disease quantification in adult patients with standard-risk acute lymphoblastic leukemia", Blood, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", Leukemia, 18(4): 709-719 (2004).
Brüggemann, et al. "Standardized MRD quantification in European ALL trials: proceedings of the Second International Symposium on MRD assessment in Kiel, Germany, Sep. 18-20, 2008", Leukemia, 24(3):521-535 (2010). doi: 10.1038/leu.2009.268. Epub Dec. 24, 2009.
Buccisano, et al. "Monitoring of minimal residual disease in acute myeloid leukemia", Curr OpinOncol., 21(6):582-588, Abstract Only (2009). doi: 10.1097/CCO.0b013e3283311856.
Buccisano, et al. "Prognostic and therapeutic implications of minimal residual disease detection in acute myeloid leukemia", Blood, 119(2): 332-341 (2012). doi: 10.1182/blood-2011-08-363291. Epub Oct. 28, 2011.
Butkus, B. "Hutch Team Uses ddPCR to Quantify T-Cell Response in Tumors; Adaptive Biotech Eyes Market", PCR Insider, Dec. 12, 2013, 3 pages http://www.genomeweb.com/print/1323296.
Bystrykh. "Generalized DNA Barcode Design Based on Hamming Codes", PLoS ONE, 7(5): e36852, 1-8 (2012).
Campana, et al. "Role of minimal residual disease monitoring in adult and pediatric acute lymphoblastic leukemia", Hemato/ Oncol Clin North Am., 23(5): 1083-1098 (2009). doi: 10.1016/j.hoc.2009.07.010.
Campana. "Minimal residual disease in acute lymphoblastic leukemia", Semin Hematol., 46(1):100-106 (2009).
Campbell et al. "Subclonal phylogenetic structures in cancer revealed by ultra-deep sequencing," PNAS, 105(35):13081-13086 (2008).
Caporaso, J.G. et al. "Global patterns of 16S rRNA diversity at a depth of millions of sequences per sample", PNAS, 108(Suppl. 1):4516-4522 (2010).
Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.
Carlson et al. "Profiling the repertoire of TCRB usage in induced and natural Treg cells", The Journal of Immunology, 186: 62.5, Abstract (2011).
Carlson, C.S et al. "Using synthetic templates to design an unbiased multiplex PCR assay", Nature Communications, 4:2680, pp. 1-9 (2013).
Carlson, et al. "Deep sequencing of the human TCRγ and TCRβ repertoires provides evidence that TCRβ rearranges after αβ, γδT cell commitment". Presented at the ASHG 2011 Conference. Oct. 2011. Poster. 1 page.
Casali, et al. "Human monoclonals from antigen-specific selection of B lymphocytes and transformation by EBV", Science, 234(4775): 476-479, Abstract Only (1986).
Casbon et al. "A method for counting PCR template molecules with application to next-generation sequencing", Nucleic Acids Research, 39(12): e81, 8 pages (2011).
Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).
Cha et al., "Improved Survival with T Cell Clonotype Stability After Anti-CTLA-4 Treatment in Cancer Patients." Sci Transl Med (2014); 6(238): 238ra70.
Chan et al. "Evaluation of Nanofluidics Technology for High-Throughput SNP Genotyping in a Clinical Setting", The Journal of Molecular Diagnostics, 13(3): 305-312 (2011).
Chen et al. "A novel approach for the analysis of T-cell reconstitution by using a T-cell receptor β-based oligonucleotide microarray in hematopoietic stem cell transplantation", Exp Hematol., 35(5):831-841 (2007).

(56) References Cited

OTHER PUBLICATIONS

Chen, et al. "Microfluidic cell sorter with integrated piezoelectric actuator", *Biomed Microdevices*, 11(6): 1223-1231 (2009). doi: 10.1007/s10544-009-9341-5.
Chen, Y. et al., "T-cell receptor gene expression in tumour-infiltrating lymphocytes and peripheral blood lymphocytes of patients with nasopharyngeal carcinoma", *British Journal of Cancer*, 72(1): 117-22 (1995).
Chinese Application No. 201380042163.X, Search Report dated Apr. 12, 2016 (English translation), 2 pages.
Chinese Patent Application No. 2014800254909, Search Report and English translation, dated May 25, 2017, mailed by the Chinese Patent Office on Jun. 6, 2017, 5 pages.
Chinese Patent Application No. 201510054401.X, Search Report dated Jul. 14, 2016, 2 pages.
Chiu, et al. "Non-invasive prenatal assessment of trisomy 21 by multiplexed maternal plasma DNA sequencing: large scale validity study", *BMJ*, 342:c7401, 9 pages (2011). doi: 10.1136/bmj.c7401.
Choi, et al. "Clonal evolution in B-lineage acute lymphoblastic leukemia by contemporaneous $V_H$-$V_H$ gene replacements and $V_H$-$DJ_H$ gene rearrangements", *Blood*, 87(6):2506-2512 (1996).
Choi, et al. "Relapse in children with acute lymphoblastic leukemia involving selection of a preexisting drug-resistant subclone", *Blood*, 110(2): 632-639 (2007).
Chothia, C. et al. "Canonical structures for the hypervariable regions of immunoglobulins," *J. Mol. Biol.*, 196:901-917, Abstract only (1987).
Chothia, C. et al. "Conformations of immunoglobulin hypervariable regions," *Nature*, 342: 877-883 (1989).
Churchill and Waterman. "The Accuracy of DNA Sequences: Estimating Sequence Quality", *Genomics*, 14:89-98 (1992).
Chute, et al. "Detection of immunoglobulin heavy chain gene rearrangements in classic Hodgkin lymphoma using commercially available BIOMED-2 primers", *Diagn Mol Pathol.*, 17(2): 65-72 (2008).
Citri et al. "Comprehensive qPCR profiling of gene expression in single neuronal cells", *Nature Protocols*, 7(1): 118-127 (2012).
Cleary, et al. "Production of complex nucleic acid libraries using highly parallel in situ oligonucleotide synthesis", *Nat Methods*, 1(3): 241-248 (2004). Epub Nov. 18, 2004.
Clemente, et al. "Deep sequencing of the T -cell receptor repertoire in CD8+ T-large granular lymphocyte leukemia identifies signature landscapes", Blood, 122(25): 4077-85 (2013). doi: 10.1182/blood-2013-05-506386. Epub Oct. 22, 2013.
Craig et al. "Identification of genetic variants using bar-coded multiplex sequencing", *Nature Methods*, 5(10): 887-893 (2008) and Supplemental Materials.
Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.
Cronn et al. "Multiplex sequencing of plant chloroplast genomes using Solexa sequencing-by-synthesis technology", *Nucleic Acids Research*, 36(19):e122, 1-11 (2008).
Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", *The Journal of Immunology*, 172:1935-1944 (2004).
Curran-Everett, D., "Multiple comparisons: philosophies and illustrations", *Am J Physiol Regulatory Integrative Comp Physiol.*, 279:R1-R8 (2000).
Currier and Robinson. "Spectratype/immunoscope analysis of the expressed TCR repertoire", *Current Protocols in Immunology*, Supplement 38:10.28.1-10.28.24 (2000).
Dash, P. et al., "Paired analysis of TCR[alpha] and TCR[beta] chains at the single-cell level in mice", *Journal of Clinical Investigation*, 121(1): 288-295 (2011).
Davi, et al. "Lymphocytic progenitor cell origin and clonal evolution of human B-lineage acute lymphoblastic leukemia", *Blood*, 88(2): 609-621 (1996).
Davis, et al. "Interrogating the repertoire: broadening the scope of peptide-MHC multimer analysis", *Nat Rev Immunol.*, 11(8): 551-558 (2011). doi: 10.1038/nri3020.
Davis, et al. "Staining of cell surface human CD4 with 2'-F-pyrimidine-containing RNA aptamers for flow cytometry", *Nucleic Acids Research*, 26(17):3915-3924 (1998).
Dean, et al. "Rapid amplification of plasmid and phage DNA using Phi 29 DNA polymerase and multiply-primed rolling circle amplification", *Genome Res.*, 11(6): 1095-1099 (2001).
Dedhia, et al. "Evaluation of DNA extraction methods and real time PCR optimization on formalin-fixed paraffin-embedded tissues", *Asian Pac J Cancer Prev.*, 8(1): 55-59 (2007).
Dekosky et al. "High-throughput sequencing of the paired human immunoglobulin heavy and light chain repertoire", *Nature Biotechnology*, 31(2): 166-169 (2013).
Deng et al. "Gene profiling involved in immature CD4+ T lymphocyte responsible for systemic lupus erythematosus", *Molecular Immunology*, 43:1497-1507 (2006).
Deschoolmeester, et al. "Tumor infiltrating lymphocytes: an intriguing player in the survival of colorectal cancer patients", *BMC Immunology*, 11:19, 12 pages (2010).
Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).
Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.
Dictor et al. "Resolving T-cell receptor clonality in two and genotype in four multiplex polymerase chain reactions", *Haematologica*, 90(11): 1524-1532 (2005).
Diederichsen, et al. "Prognostic value of the CD4+/CD8+ ratio of tumour infiltrating lymphocytes in colorectal cancer and HLA-DR expression on tumour cells", *Cancer Immunol Immunother.*, 52(7):423-428 (2003). Epub Apr. 15, 2003.
Diehl, et al. "BEAMing: single-molecule PCR on microparticles in water-in-oil emulsions", *Nat Methods*, 3(7):551-559, Abstract Only (2006).
Ding, et al. "Clonal evolution in relapsed acute myeloid leukaemia revealed by whole-genome sequencing", *Nature*, 481(7382):506-510 (2012).
Diviacco, et al. "A novel procedure for quantitative polymerase chain reaction by coamplification of competitive templates", *Gene*, 122(2):313-320 (1992).
Dobosy, J. et al. "RNase H-dependent PCR (rhPCR): improved specificity and single nucleotide polymorphism detection using blocked cleavable primers", *BMC Biotechnology*, 11(80):1-18 (2011).
Dohm, et al. "Substantial biases in ultra-short read data sets from high throughput DNA sequencing", *Nucleic Acids Research*, 36:e105, 10 pages (2008).
Dou, et al. "Analysis of T cell receptor $V_\beta$ gene usage during the course of disease in patients with chronic hepatitis B", *Journal of Biomedical Science*, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", *Science*, 327(5961):78-81 (2010). Epub Nov. 5, 2009.
Droege, et al. "The Genome Sequencer FLX System—longer reads, more applications, straight forward bioinformatics and more complete data sets", *J Biotechnol.*, 136(1-2):3-10 (2008). doi: 10.1016/j.jbiotec.2008.03.021. Epub Jun. 21, 2008.
Droese, J., et al. "Validation of BIOMED-2 multiplex PCR tubes for detection of TCRB gene rearrangements in T-cell malignancies," *Leukemia*, 18:1531-1538 (2004).

(56) References Cited

OTHER PUBLICATIONS

Du et al. "TCR spectratyping revealed T lymphocytes associated with graft-versus-host disease after allogeneic hematopoietic stem cell transplantation", *Leukemia & Lymphoma*, 48(8):1618-1627 (2007).
Dueñas, M., et al. "In vitro immunization of naive human B cells yields high affinity immunoglobulin G antibodies as illustrated by phage display." Immunology (1996); 89.1: 1-7.
Dunn, et al. "Focus on TILs: Prognostic significance of tumor infiltrating lymphocytes in human glioma", *Cancer Immun.*, 7:12, 16 pages (2007).
Eason et al. "Characterization of synthetic DNA bar codes in *Saccharomyces cerevisiae* gene-deletion strains," PNAS, 101(30): 11046-11051 (2004).
Edd et al. "Controlled encapsulation of single cells into monodisperse picoliter drops", *Lab Chip*, 8(8):1262-1264 (2008).
Efron and Thisted, "Estimating the No. of unseen species: How many words did Shakespeare know?" Biometrika (1976); 63(3): 435-447.
Eichler, et al. "Haplotype and interspersion analysis of the FMR1 CGG repeat identifies two different mutational pathways for the origin of the fragile X syndrome", *Hum Mol Genet.*, 5(3):319-330 (1996).
Eichler, et al. "Length of uninterrupted CGG repeats determines instability in the FMR1 gene", *Nat Genet.*, 8(1):88-94, Abstract Only (1994).
Eid et al. "Real-time DNA sequencing from single polymerase molecules", *Science*, 323(5910):133-138 (2009). Epub Nov. 20, 2008.
Eis, et al. "An invasive cleavage assay for direct quantitation of specific RNAs", *Nat Biotechnol.*, 19(7):673-676, Abstract Only (2001).
Eisenstein. "Personalized, sequencing-based immune profiling spurs startups", Nat Biotechnol., 31(3):184-186 (2013). doi: 10.1038/nbt0313-184b.
Elkord et al. "T regulatory cells in cancer: recent advances and therapeutic potential", *Expert Opinion on Biological Therapy*, 10(11): 1573-1586 (2010).
Emerson et al. "Defining the Alloreactive T Cell Repertoire Using High-Throughput Sequencing of Mixed Lymphocyte Reaction Culture", *PLoS One*, 9(11): e111943 (2014).
Emerson, et al. "CD4+ and CD8+ T cell β antigen receptors have different and predictable V and J gene usage and CDR3 lengths", Presented at the Annual Meeting of the American Association of Immunologists 2012 in Boston, MA, May 2012. Poster.
Emerson, et al. "Correlation of TCR diversity with immune reconstitution after cord blood transplant", Presented at the American Society of Clinical Oncology's annual meeting. May 2012. Poster. 1 page.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Emerson, R.O. et al. "High-throughput sequencing of T-cell receptors reveals a homogeneous repertoire of tumour-infiltrating lymphocytes in ovarian cancer", *Journal of Pathology*, 231: 433-440 (2013).
Esendagli et al. "Malignant and non-malignant lung tissue areas are differentially populated by natural killer cells and regulatory T cells in non-small cell lung cancer", *Lung Cancer*, 59(1): 32-40 (2008).
Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.1300622. Epub Oct. 25, 2013.
European Application No. 09764927.1, European Opposition dated Oct. 15, 2014 (in French only).
European Application No. 09764927.1, Notice of Opposition dated Oct. 14, 2014.
European Application No. 10732172.1, Extended European Search Report dated May 29, 2012, 5 pages.
European Application No. 16162568.6, Extended European Search Report dated Jul. 20, 2016, 6 pages.
European Patent Application No. 09764927.1, EPO's Communication of Notices of Opposition, dated Nov. 21, 2014.
European Application No. 09764927.1, Opponent's Response to Submission of the Patentee dated Nov. 23, 2015.
European Application No. 09764927.1, Patentee's Observations/Response dated May 27, 2015.
European Application No. 11777704.5, European Search Report dated Jul. 26, 2013, 6 pages.
European Application No. 13195379.6, Extended European Search Report and Opinion dated Mar. 13, 2014, 6 pages.
European Application No. 13757482.8, Extended European Search Report dated Jun. 6, 2016, 5 pages.
European Application No. 13775514.6, Extended European Search Report dated Dec. 1, 2015, 12 pages.
European Application No. 13804085.2, Extended European Search Report dated Nov. 16, 2015, 10 pages.
European Application No. 13828563.0, Extended European Search Report dated Feb. 12, 2016, 10 pages.
European Application No. 14819680.1, Extended European Search Report dated Feb. 10, 2017, 10 pages.
European Application No. 15758762.7, Extended European Search Report dated Sep. 22, 2017, 12 pages.
European Application No. 15772627.4, Extended European Search Report dated Jul. 19, 2017, 8 pages.
European Application No. 15779750.7, Extended European Search Report dated Aug. 9, 2017, 9 pages.
European Application No. 15854358.7, Extended European Search Report dated Mar. 12, 2018, 12 pages.
European Application No. 16165939.6, Extended European Search Report dated Oct. 7, 2016, 9 pages.
European Application No. 16183402.3, Extended European Search Report dated Feb. 21, 2017, 8 pages.
European Application No. 16756268.5, Extended European Search Report dated Oct. 22, 2018, 20 pages.
European Application No. 16756268.5, Partial Supplementary European Search Report dated Jun. 19, 2018, 21 pages.
European Application No. 16774304.6, Extended European Search Report dated Oct. 15, 2018, 9 pages.
European Application No. 18153536.0, Extended European Search Report dated Jun. 6, 2018, 7 pages.
European Application No. 18184843.3, Extended European Search Report dated Aug. 13, 2018, 10 pages.
European Application No. 18211168.2, Extended European Search Report dated Jan. 31, 2019, 6 pages.
Faham, M. et al. "Deep-sequencing approach for minimal residual disease detection in acute lymphoblastic leukemia", *Blood*, 120(26): 5173-5180 (2012).
Ferradini et al. "Analysis of T Cell Receptor Variability in Tumor-infiltrating Lymphocytes from a Human Regressive Melanoma", *J. Clin. Invest.*, 91(3): 1183-1190 (1993).
Ferrero, et al. "Multiple myeloma shows No. intra-disease clustering of immunoglobulin heavy chain genes", *Haematologica*, 97(6): 849-853 (2012). doi: 10.3324/haematol.2011.052852. Epub Dec. 29, 2011.
Flaherty et al. "Ultrasensitive detection of rare mutations using next-generation targeted resequencing", *Nucleic Acids Research*, 40(1): e2, 12 pages (2012).
Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", *Leukemia*, 22:771-782 (2008).
Födinger et al., "Multiplex PCR for rapid detection of T-cell receptor-gamma chain gene rearrangements in patients with lymphoproliferative diseases." British Journal of Haematology (1996); 94(1): 136-139.
Frank. "Barcrawl and BARTAB: software tools for the design and implementation of barcoded primers for highly multiplexed DNA sequencing," *BMC Bioinformatics*, 10: 362 (2009).

(56) References Cited

OTHER PUBLICATIONS

Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", *Biotechniques*, 6(1): 112-125 (1999).
Freeman, J.D., et al. "Profiling the T-Cell Receptor Beta-Chain Repertoire by Massively Parallel Sequencing", *Genome Research*, 19(10): 1817-1824 (2009). Epub Jun. 18, 2009.
Fridman, et al. "Prognostic and predictive impact of intra- and peritumoral immune infiltrates", *Cancer Research*, 71(17): 5601-5605 (2011). Epub Aug. 16, 2011.
Fritz et al. "Alterations in the spinal cord T cell repertoire during relapsing experimental autoimmune encephalomyelitis," *J Immunol*, 164:6662-6668 (2000).
Fu et al. "Counting individual DNA molecules by the stochastic attachment of diverse labels", *PNAS*, 108(22): 9026-9031 and Supporting Materials, 8 pages (2011).
Fuller, et al. "The challenges of sequencing by synthesis", *Nat Biotechnol.*, 7(11): 1013-1023 (2009) (Abstract only). Epub Nov. 6, 2009.
García-Castillo and Nunez, et al. "Detection of clonal immunoglobulin and T-cell receptor gene recombination in hematological malignancies: monitoring minimal residual disease", *Cardiovascular & Haematological Disorders-Drug Targets*, 9:124-135 (2009).
Gauss, et al. "Mechanistic constraints on diversity in human V(D)J recombination", *Mol Cell Biol.*, 16(1):258-269 (1996).
Gawad, et al. "Massive evolution of the immunoglobulin heavy chain locus in children with B precursor acute lymphoblastic leukemia", *Blood*, 120(22):4407-4417 (2012). Epub Aug. 28, 2012.
Georgiou, G., et al., "The promise and challenge of high-throughput sequencing of the antibody repertoire." Nat Biotechnol (2014); 32(2): 158-168.
Gerlinger and Swanton. "How Darwinian models inform therapeutic failure initiated by clonal heterogeneity in cancer medicine", *British Journal of Cancer*, 103(8):1139-1143 (2010). Epub Sep. 28, 2010.
Gerlinger, M. et al. "Ultra deep T cell receptor sequencing reveals the complexity and intratumour heterogeneity of T cell clones in renal cell carcinomas", *Journal of Pathology*, 231:424-432 (2013).
Germano, et al. "Clonality profile in relapsed precursor-B-ALL children by GeneScan and sequencing analyses. Consequences on minimal residual disease monitoring", *Leukemia*, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-1054 (2013). Epub Feb. 5, 2013.
Gilbert, et al. "The isolation of nucleic acids from fixed, paraffin-embedded tissues-which methods are useful when?", *PLoS One*, 2(6): e537, 12 pages (2007).
Giuggio, et al. "Evolution of the intrahepatic T cell repertoire during chronic hepatitis C virus infection", *Viral Immunology*, 18(1):179-189 (2005).
Gloor et al. "Microbiome profiling by Illumina sequencing of combinatorial sequence-tagged PCR products," *PLoS ONE*, 5(10): e15406, 15 pages (2010).
Godelaine, et al. "Polyclonal CTL responses observed in melanoma patients vaccinated with dendritic cells pulsed with a MAGE-3.A1 peptide", *J Immunol.*, 171(9):4893-4897 (2003).
Golembowski, et al. "Clonal evolution in a primary cutaneous follicle center B cell lymphoma revealed by single cell analysis in sequential biopsies", *Immunobiology*, 201(5):631-644 (2000).
Gonzalez et al., "Incomplete DJH rearrangements as a novel tumor target for minimal residual disease quantitation in multiple myeloma using real-time PCR", Leukemia, 17:1051-1057 (2003).
Gonzalez, et al. "Incomplete DJH rearrangements of the IgH gene are frequent in multiple myeloma patients: immunobiological characteristics and clinical implications", *Leukemia*, 17:1398-1403 (2003).
Gonzalez, S.F., et al. "Trafficking of B Cell Antigen in Lymph Nodes", *Ann. Rev. Immunol.*, 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", *J Immunol.*, 152(10):5109-5119 (1994).
Gottenberg, et al. "Markers of B-lymphocyte activation are elevated in patients with early rheumatoid arthritis and correlated with disease activity in the ESPOIR cohort", *Arthritis Res Ther.*, 11(4): R114 (2009). Epub Jul. 23, 2009.
Gratama and Kern. "Flow cytometric enumeration of antigen-specific T lymphocytes", *Cytometry A*, 58(1): 79-86 (2004).
Gratama, et al. "Measuring antigen-specific immune responses", 2008 update. *Cytometry A.*, 73(11): 971-974 (2008).
Green, et al. "Clonal diversity of Ig and T-cell-receptor gene rearrangements identifies a subset of childhood B-precursor acute lymphoblastic leukemia with increased risk of relapse", *Blood*, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", *Nature*, 446(7132): 153-158 (2007).
Grupp, et al. "Chimeric antigen receptor-modified T cells for acute lymphoid leukemia", N Engl J Med., 368(16):1509-1518 (2013). Epub Mar. 25, 2013.
Gulliksen, et al. "Real-time nucleic acid sequence-based amplification in nanoliter volumes", *Anal Chem.*, 76(1): 9-14, Abstract Only (2004).
Gunderson et al. "Decoding Randomly Ordered DNA Arrays", *Genome Research*, 14: 870-877 (2004).
Guo, et al. "Sequence changes at the V-D junction of the $V_H1$ heavy chain of anti-phosphocholine antibodies alter binding to and protection against *Streptococcus pneumoniae*", *Int Immunol.*, 9(5):665-677 (1997).
Gurrieri, et al. "Chronic lymphocytic leukemia B cells can undergo somatic hypermutation and intraclonal immunoglobulin $V_HDJ_H$ gene diversification", *J Exp Med.*, 196(5):629-639 (2002).
Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", *Leukemia & Lymphoma*, 48(7): 1338-1343 (2007).
Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Hanahan, et al. "Hallmarks of cancer: the next generation", *Cell*, 144(5): 646-674 (2011). doi: 10.1016/j.cell.2011.02.013.
Harismendy et al. "Evaluation of next generation sequencing platforms for population targeted sequencing studies", *Genome Biology*, 10:R32, 13 pages (2009).
Hawkins, et al. "Whole genome amplification—applications and advances", *Curr Opin Biotechnol.*, 13(1): 65-67 (2002).
He, et al. "IgH gene rearrangements as plasma biomarkers in Non-Hodgkin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798 &hq_I=10&hq_v=2357e2f0b3. Accessed Apr. 6, 2011.

(56) References Cited

OTHER PUBLICATIONS

Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", Science, 269(5222): 400-403 (1995).
Hill, et al. "Using ecological diversity measures with bacterial communities", FEMS Microbiol Ecol., 43(1):1-11 (2003). doi: 10.1111/j.1574-6941.2003.tb01040.x.
Hirohata, et al. "Regulation of human B cell function by sulfasalazine and its metabolites", Int Immunopharmacol., 2(5): 631-640, Abstract Only (2002).
Hodges, E. et al. "Diagnostic role of tests for T cell receptor (TCR) genes", J Clin Pathol., 56(1): 1-11 (2003).
Holt and Jones. "The new paradigm of flow cell sequencing", Genome Research, 18:839-846 (2008).
Holt. "Q &A: BC cancer agency's Robert Holt on sequencing the immune repertoire in immune reconstitution," Genome Web (www.genomeweb.com) Jun. 30, 2009.
Hoogenboom, et al. "Multi-subunit proteins on the surface of filamentous phage: methodologies for displaying antibody (Fab) heavy and light chains", Nucleic Acids Res., 19(15): 4133-4137 (1991).
Hoogendoorn, et al. "Primary allogeneic T-cell responses against mantle cell lymphoma antigen-presenting cells for adoptive immunotherapy after stem cell transplantation", Clin Cancer Res., 11(14): 5310-5318 (2005).
Hoos, et al. "Improved endpoints for cancer immunotherapy trials", J Natl Cancer Inst., 102(18): 1388-1397 (2010). Epub Sep. 8, 2010.
Hosono, et al. "Unbiased whole-genome amplification directly from clinical samples", Genome Res., 13(5): 954-964 (2003). Epub Apr. 14, 2003.
Hoven, et al. "Detection and isolation of antigen-specific B cells by the fluorescence activated cell sorter (FACS)", J Immunol Methods, 117(2): 275-284, Abstract Only, 2 pages (1989).
Howe, et al. "T cell receptor clonotype analysis of T cell responses: Diagnostic application of a clonotypic database", Blood (2003); 102 (11): Abstract 3918, p. 54b, 1 page.
Howie, et al., "High throughput pairing of T cell receptor a and B sequences." Science Translational Medicine (2015); 7(301): 301ra131, and supplementary materials, 19 pages.
Huh, et al. "Microfluidics for flow cytometric analysis of cells and particles", Physiol Meas., 26(3): R73-98, Abstract Only (2005). Epub Feb. 1, 2005.
Huijsmans, et al. "Comparative analysis of four methods to extract DNA from paraffin-embedded tissues: effect on downstream molecular applications", BMC Res Notes, 3:239, 9 pages (2010).
Huse, et al. "Generation of a large combinatorial library of the immunoglobulin repertoire in phage lambda", Science, 246(4935): 1275-1281, Abstract Only (1989).
Hwang, H.Y et al. "Identification of a Commonly used CDR3 Region of Infiltrating T Cells Expressing Vβ13 and Vβ15 Derived from Psoriasis Patients", The Journal of Investigative Dermatology, 120(3): 359-364 (2003).
Iancu, et al. "Profile of a serial killer: cellular and molecular approaches to study individual cytotoxic T- cells following therapeutic vaccination", J Biomed Biotechnol., 2011: 452606 (2011). doi: 10.1155/2011/452606. Epub Nov. 14, 2010.
Ilakovac, V., "Statistical hypothesis testing and some pitfalls." Biochemia Medica (2009); 19(1): 10-16, 4 pages. [online]. [Retrieved on 2016.04.12]. Retrieved from the Internet: <URL:http://www.biochemia-medica.com/contentlstatistical-hypothesis-testing-and-some-pitfalls>PDF.
Illumina Systems & Software, Technology Spotlight, DNA Sequencing with Solexa® Technology, Illumina, Inc., Pub. No. 770-2007-002, 4 pages (2007).
Illumina. "Technical Note: Systems and Software. Calling sequencing SNPs", 3 pages (2010).
Illumina. Data Sheet, "TruSeg™ exome enrichment kit", 5 pages (2011).
Illumina. Data Sheet: Sequencing. Genomic Sequencing. Pub. No. 770.2008-016 Reference states: "Current as of Jan. 30, 2009", 6 pages, Copyright 2010.
Illumina. TruSeq Sample Preparation Kit and Data Sheet. Illumina, Inc., San Diego, CA, 4 pages (2011).
Ishii et al. "Isolation and expression profiling of genes upregulated in the peripheral blood cells of systemic lupus erythematosus patients," DNA Research, 12:429-439 (2005).
Jabara et al. "Accurate sampling and deep sequencing of the HIV-1 protease gene using a Primer ID", PNAS, 108(50): 20166-20171 (2011).
Jacobi et al. "Activated memory B cell subsets correlate with disease activity in systemic lupus erythematosus: delineation by expression of CD27, IgD, and CD95", Arthritis & Rheumatism, 58(6):1762-1773 (2008).
Jacobi et al. "Correlation between circulating $CD27^{high}$ plasma cells and disease activity in patients with systemic lupus erythematosus" Arthritis & Rheumatism, 48(5):1332-1342 (2003).
Jaffe, et al. "Classification of lymphoid neoplasms: the microscope as a tool for disease discovery", Blood, 112(12): 4384-4399 (2008). doi: 10.1182/blood-2008-07-077982.
Jalla, et al. "Enumeration of lymphocyte subsets using flow cytometry: Effect of storage before and after staining in a developing country setting", Indian J Clin Biochem., 19(2): 95-99 (2004). doi: 10.1007/BF02894264.
Jena, et al. "Amplification of genes, single transcripts and cDNA libraries from one cell and direct sequence analysis of amplified products derived from one molecule", J. Immunol. Methods, 190:199-213 (1996).
Jochems and Schlom. "Tumor-infiltrating immune cells and prognosis: the potential link between conventional cancer therapy and immunity", Exp Biol Med (Maywood), 236(5): 567-579 (2011). Epub Apr. 12, 2011.
Jung, et al. "Unraveling V(D)J recombination; insights into gene regulation", Cell, 116(2): 299-311 (2004).
Jurkat, Clone 6-1 (ATCC TIB-152) Webpage retrievable from the ATCC under http://www.lgcstandards-atcc.org/Products/ All MB-152.aspx#characteristics. Accessed Oct. 14, 2014.
Kanda, et al. "Immune recovery in adult patients after myeloablative dual umbilical cord blood, matched sibling, and matched unrelated donor hematopoietic cell transplantation", Biol Blood Marrow Transplant, 18(11):1664-1676 (2012). doi: 10.1016/j.bbmt. 2012.06.005. Epub Jun. 12, 2012.
Kato et al. "Analysis of accumulated T cell clonotypes in patients with systemic lupus erythematosus," Arthritis & Rheumatism, 43(12):2712-2721 (2000).
Katz, S.C. et al. "T Cell Infiltrate Predicts Long-Term Survival Following Resection of Colorectal Cancer Liver Metastases," Ann. Surg. Oncol., 16:2524-2530 (2009).
Kedzierska, et al. "Tracking phenotypically and functionally distinct T cell subsets via T cell repertoire diversity", Mol Immunol., 45(3): 607-618 (2008). Epub Aug. 24, 2007.
Kiianitsa, et al., "Development of Tools for T-Cell Repertoire Analysis (TCRB Spectratyping) for the Canine Model of Hematopoietic Cell Transplantation", Blood, ASH-Annual Meeting Abstracts, 110 (11): Abstract 4873, 2 pages (2007).
Kim, et al. "An efficient and reliable DNA extraction method for preimplantation genetic diagnosis: a comparison of allele drop out and amplification rates using different single cell lysis methods", Fertility and Sterility, 92: 814-818 (2009).
Kim, et al. "Polony multiplex analysis of gene expression (PMAGE) in mouse hypertrophic cardiomyopathy", Science, 316(5830):1481-1484 (2007).
Kinde et al. "Detection and quantification of rare mutations with massively parallel sequencing," PNAS, 108(23): 9530-9535 and Supporting Information, 16 pages (2011).
Kircher, et al. "Improved base calling for the Illumina Genome Analyzer using machine learning strategies", Genome Biol., 10(8): R83, 9 pages (2009). doi: 10.1186/GB-2009-10-8-r83. Epub Aug. 14, 2009.
Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.

(56) References Cited

OTHER PUBLICATIONS

Kita, et al. "T cell receptor clonotypes in skin lesions from patients with systemic lupus erythematosus", *Journal of Investigative Dermatology*, 110(1): 41-46 (1988).
Kivioja et al. "Counting absolute numbers of molecules using unique molecular identifiers," *Nature Methods*, 9(1): 72-76 (2012).
Klarenbeek, P.L. et al. "Deep sequencing of antiviral T-cell responses to HCMV and EBV in humans reveals a stable repertoire that is maintained for many years." PLoS Pathogens (2012); 8.9: e1002889.
Klarenbeek, P.L. et al. "Human T-cell memory consists mainly of unexpanded clones", *Immunology Letters*, 133: 42-48 (2010).
Klenerman, et al. "Tracking T cells with tetramers: new tales from new tools", *Nat Rev Immunol.*, 2(4):263-272 (2002).
Klinger et al. "Combining next-generation sequencing and immune assays: a novel method for identification of antigen-specific T cells", PLoS One, 8(9): e74231, 1-9 (2013).
Kneba, et al. "Characterization of clone-specific rearrangement T-cell receptor gamma-chain genes in lymphomas and leukemias by the polymerase chain reaction and DNA sequencing", *Blood*, 84(2):574-581 (1994).
Kneba, M., et al. "Analysis of Rearranged T-cell Receptor β-Chain Genes by Polymerase Chain Reaction (PCR) DNA Sequencing and Automated High Resolution PCR Fragment Analysis", *Blood*, 86:3930-3937 (1995).
Kobari, et al. "T cells accumulating in the inflamed joints of a spontaneous murine model of rheumatoid arthritis become restricted to common clonotypes during disease progression", *Int Immunol.*, 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," *Ann Surg.*, 244(6): 986-992; discussion 992-993 (2006).
Kohlmann, et al. "Integration of next-generation sequencing into clinical practice: are we there yet?", *Semin Oncol.*, 39(1): 26-36, Abstract Only (2012).
Kojima et al. "PCR amplification from single DNA molecules on magnetic beads in emulsion: application for high-throughput screening of transcription factor targets", *Nucleic Acids Research*, 33: 17, e150, 9 pages (2005).
Krause et al. "Epitope-Specific Human Influenza Antibody Repertoires Diversify by B Cell Intraclonal Sequence Divergence and Interclonal Convergence", *The Journal of Immunology*, 187: 3704-3711 (2011).
Krueger, et al. "Large scale loss of data in low-diversity illumina sequencing libraries can be recovered by deferred cluster calling", *PLoS One*, 6(1): e16607, 7 pages (2011).
Ku, et al. "Exome sequencing: dual role as a discovery and diagnostic tool", *Ann Neurol.*, 71(1):5-14, Abstract Only (2012). doi: 10.1002/ana.22647.
Kumar, et al. "PEG-labeled nucleotides and nanopore detection for single molecule DNA sequencing by synthesis", *Sci Rep.*, 2:684, 8 pages (2012). Epub Sep. 21, 2012.
Kwak, et al. "Induction of immune responses in patients with B-cell lymphoma against the surface-immunoglobulin idiotype expressed by their tumors", *N Engl J Med.*, 327(17):1209-1215 (1992).
Kyu et al. "Frequencies of human influenza-specific antibody secreting cells or plasmablasts post vaccination from fresh and frozen peripheral blood mononuclear cells", *Journal of Immunological Methods*, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", *Blood*, vol. 120, No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", *Experimental Hematology*, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", *American Society for Blood and Marrow Transplantation*, 6(3):241-253 (2000).
Langerak, et al. "Immunoglobulin/T-cell receptor clonality diagnostics", *Expert Opin. Med. Diagn.*, 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).
Laplaud et al. "Blood T-cell receptor β chain transcriptome in multiple sclerosis. Characterization of the T cells with altered CDR3 length distribution", *Brain*, 127:981-995 (2004).
Laplaud et al. "Serial blood T cell repertoire alterations in multiple sclerosis patients; correlation with clinical and MRI parameters", *Journal of Neuroimmunology*, 177(1-2):151-160 (2006).
Larimore, K., et al. "Shaping of Human Germline IgH Repertoires Revealed by Deep Sequencing", *The Journal of Immunology*, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", *J Mol Diagn.*, 7(5): 582-591 (2005).
Lee, et al. "Characterization of circulating T cells specific for tumor-associated antigens in melanoma patients", *Nat Med.*, 5(6): 677-685, Abstract Only (1999).
Lee, et al. "Prognostic implications of type and density of tumour-infiltrating lymphocytes in gastric cancer", *Br J Cancer*, 99(10): 1704-1711 (2008). Epub Oct. 21, 2008.
Lefranc. "IMGT, the international ImMunoGeneTics database", *Nucleic Acids Res.*, 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", *PLoS One*, 3(2):e1678, 11 pages (2008).
Leone, et al. "Molecular beacon probes combined with amplification by NASBA enable homogeneous, real-time detection of RNA", *Nucleic Acids Research*, 26(9): 2150-2155 (1998).
Leproust, et al. "Synthesis of high-quality libraries of long (150mer) oligonucleotides by a novel depurination controlled process", *Nucleic Acids Res.*, 38(8): 2522-2540 (2010). Epub Mar. 22, 2010.
Lessin, et al. "Molecular diagnosis of cutaneous T-cell lymphoma: polymerase chain reaction amplification of T-cell antigen receptor beta-chain gene rearrangements", *J Invest Dermatol.*, 96(3): 299-302 (1991).
Li, et al. "An improved one-tube RT-PCR protocol for analyzing single-cell gene expression in individual mammalian cells", *Anal. Bioanal. Chem.*, 397: 1853-1859 (2010).
Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).
Li, et al. "Detailed clonality analysis of relapsing precursor B acute lymphoblastic leukemia: implications for minimal residual disease detection", *Leukemia Research*, 25:1033-1045 (2001).
Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).
Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).
Li, et al. "β cell-specific CD4+ T cell clonotypes in peripheral blood and the pancreatic islets are distinct", *J Immunol.*, 183(11): 7585-7591 (2009). Epub Nov. 16, 2009.
Liedtke, et al. "A comparison of methods for RNA extraction from lymphocytes for RT-PCR", *PCR Methods and Applications*, 4(3): 185-187 (1994).
Lin, et al. "Multiplex genotype determination at a large number of gene loci", *Proc Natl Acad Sci USA*, 93(6): 2582-2587 (1996).

(56) References Cited

OTHER PUBLICATIONS

Liu, et al. "CD127 expression inversely correlates with FoxP3 and suppressive function of human CD4+ T reg cells", *J Exp Med.*, 203(7): 1701-1711 (2006). Epub Jul. 3, 2006.
Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.
Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).
Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).
Lorimer, I. A., and Pastan, Ira. "Random recombination of antibody single chain Fv sequences after fragmentation with DNaseI in the presence of Mn2+." Nucleic Acids Research (1995); 23.15: 3067-3068.
Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.
Lovisa, et al. "IGH and IGK gene rearrangements as PCR targets for pediatric Burkitt's lymphoma and mature B-ALL MRD analysis", *Lab Invest.*, 89(10):1182-1186 (2009).
Lowe, T., et al. "A computer program for selection of oligonucleotide primers for polymerase chain reactions," Nucleic Acids Research (1990); 18(7):1757-1761.
Lowman, et al. "Monovalent phage display: a method for selecting variant proteins from random libraries", *Methods: A Companion to Methods in Enzymology*, 3: 205-216, Abstract Only (1991).
Lúcio, P. et al. "Flow cytometric analysis of normal B cell differentiation: a frame of reference for the detection of minimal residual disease in precursor-B-ALL", *Leukemia*, 13:419-427 (1999).
Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).
Lyamichev, et al. "Polymorphism identification and quantitative detection of genomic DNA by invasive cleavage of oligonucleotide probes", *Nat Biotechnol.*, 17(3): 292-396 (1999).
Mackay, et al. "Real-time PCR in virology", *Nucleic Acids Res.*, 30(6): 1292-1305 (2002).
Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.
Manion et al., "Reducing Error in Next Generation Sequencing Data with NextGENe Software's Condensation Tool™", Mar. 2009, pp. 1-3.
Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.
Mar et al. "Inferring steady state single-cell gene expression distributions from analysis of mesoscopic samples", *Genome Biology*, 7(12): R119, 12 pages (2006).
Mardis. "Next-generation DNA sequencing methods", *Annu. Rev. Genomics Hum. Genet.*, 9:387-402 (2008).
Margulies, et al. "Genome sequencing in microfabricated high-density picolitre reactors", *Nature*, 437(7057): 376-380 (2005). Epub Jul. 31, 2005.
Mariani, S. et al., "Comprehensive assessment of the TCRBV repertoire in small T-cell samples by means of an improved and convenient multiplex PCR method," *Experimental Hematology*, 37(6): 728-738 (2009).
Markoulatos, P. et al., "Multiplex Polymerase Chain Reaction: A Practical Approach", Journal of Clinical Laboratory Analysis, 16: 47-51 (2002).

Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).
Mary et al. "Analysis of gene expression at the single-cell level using microdroplet-based microfluidic technology", *Biomicrofluidics*, 5: 024109-1-024109-10 (2011).
Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).
Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).
Mato et al. "Correlation of clonal T cell expansion with disease activity in systemic lupus erythematosus", *Int Immunol.*, 9(4):547-554 (1997).
Matolcsy, et al. "Clonal evolution of B cells in transformation from low- to high-grade lymphoma", *Eur. J. Immunol.*, 29(4):1253-1264 (1999).
Matsumoto et al. "CDR3 spectratyping analysis of the TCR repertoire in Myasthenia Gravis", *The Journal of Immunology*, 176:5100-5107 (2006).
Matsumoto et al. "Complementarity-determining region 3 spectratyping analysis of the TCR repertoire in multiple sclerosis", *The Journal of Immunology*, 170:4846-4853 (2003).
Mazor et al. "Antibody internalization studied using a novel IgG binding toxin fusion", *Journal of Immunological Methods*, 321: 41-59 (2007).
Mazumder, et al., "Detection of multiple myeloma cells in peripheral blood using high-throughput sequencing assay" *Blood*, vol. 120, No. 21, Abstract 321 (Conference Abstract), Entire Abstract (2012).
McCloskey et al. "Encoding PCR products with batch-stamps and barcodes," *Biochem. Genet.*, 45: 761-767 (2007).
McLean et al. "Recognition of human cytomegalovirus by human primary immunoglobulins identifies an innate foundation to an adaptive immune response", J. Immunol., 174(8): 4768-4778 (2005).
Mei et al. "Blood-borne human plasma cells in steady state are derived from mucosal immune responses", *Blood*, 113(11): 2461-2469 (2009).
Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).
Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.
Meier, et al. "The influence of different stimulation conditions on the assessment of antigen-induced CD154 expression on CD4+ T cells", *Cytometry A.*, (11):1035-1042 (2008). doi: 10.1002/cyto.a.20640.
Meijer et al. "Isolation of Human Antibody Repertoires with Preservation of the Natural Heavy and Light Chain Pairing", *J. Mol. Biol.*, 358: 764-772 (2006).
Meleshko, et al. "Rearrangements of IgH, TCRD and TCRG genes as clonality marker of childhood acute lymphoblastic leukemia", *Experimental Oncology*, 27(4):319-324 (2005).
Menezes et al. "A public T cell clonotype within a heterogeneous autoreactive repertoire is dominant in driving EAE", *J Clin Invest*, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", Nature Reviews, Genetics, 11:31-46 (2010).
Meyer et al. "Targeted high-throughput sequencing of tagged nucleic acid samples", *Nucleic Acids Research*, 35(15): e97, 5 pages (2007).

(56) References Cited

OTHER PUBLICATIONS

Miceli and Parnes. "The roles of CD4 and CD8 in T cell activation", *Seminars in Immunology*, 3(3): 133-141 (1991). Abstract only.

Michálek, et al. "Detection and long-term in vivo monitoring of individual tumor-specific T cell clones in patients with metastatic melanoma", *J Immunol.*, 178(11):6789-6795 (2007).

Michálek, et al. "Identification and monitoring of graft-versus-host specific T-cell clone in stem cell transplantation", *The Lancet*, 361(9364): 1183-1185 (2003).

Miller, et al., "Assembly algorithms for next-generation sequencing data", Genomics, 95(6): 315-327 (2010).

Miltenyi, et al. "High gradient magnetic cell separation with MACS", *Cytometry*, 11(2): 231-238 (1990).

Miner et al. "Molecular barcodes detect redundancy and contamination in hairpin-bisulfite PCR", *Nucleic Acids Research*, 32(17): e135, 4 pages (2004).

Miqueu, P. et al. "Statistical analysis of CDR3 length distributions for the assessment of T and B cell repertoire biases", *Molecular Immunology*, 44:1057-1064 (2007).

Mitra, et al. "Fluorescent in situ sequencing on polymerase colonies", *Anal Biochem.*, 320(1): 55-65, Abstract Only (2003).

Miyashita, et al. "N-Methyl substituted 2',4'- BNANC: a highly nuclease-resistant nucleic acid analogue with high-affinity RNA selective hybridization", *Chem Commun* (Camb), (36): 3765-3767, Abstract Only (2007). Epub Jul. 9, 2007.

Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).

Molloy, et al. "Soluble T cell receptors: novel immunotherapies", *Curr Opin Pharmacol.*, 5(4): 438-443 (2005) (Abstract Only).

Monod, M.Y. et al. "IMGT/JunctionAnalysis: the first tool for the analysis of the immunoglobulin and T cell receptor complex V-J and V-D-J JUNCTIONs", *Bioinformatics*, 20(Suppl 1):I379-385 (2004).

Moody, et al. "Antigen-specific B cell detection reagents: use and quality control", *Cytometry A.*, 73(11): 1086-1092 (2008). doi: 10.1002/cyto.a.20599.

Morgan, et al. "Cancer regression in patients after transfer of genetically engineered lymphocytes", *Science*, 314(5796): 126-129 (2006). Epub Aug. 31, 2006.

Morozova et al. "Applications of New Sequencing Technologies for Transcriptome Analysis", *Annu. Rev. Genomics Hum. Genet.*, 10: 135-151 (2009).

Morrissy et al. "Next-generation tag sequencing for cancer gene expression profiling", *Genome Research*, 19: 1825-1835 (2009).

Moss, et al. "The human T cell receptor in health and disease", *Annu. Rev. Immunol.*, 10:71-96 (1992).

Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.

Muraro et al. "Molecular tracking of antigen-specific T cell clones in neurological immune-mediated disorders", *Brain*, 126(Pt 1):20-31 (2003).

Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.

Naito, et al. "CD8+ T cells infiltrated within cancer cell nests as a prognostic factor in human colorectal cancer", *Cancer Research*, 58(16): 3491-3494 (1998).

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Nelson. "CD20+ B cells: the other tumor-infiltrating lymphocytes", *The Journal of Immunology*, 185(9): 4977-4982 (2010). doi: 10.4049/jimmunol.1001323.

Newman, et al. "Identification of an antigen-specific B cell population", *J Immunol Methods*, 272(1-2): 177-187, Abstract Only (2003).

Nguyen et al. "Identification of errors introduced during high throughput sequencing of the T cell receptor repertoire" *BMC Genomics*, 12: 106, 13 pages (2011).

Nielsen, et al. "Peptide nucleic acid (PNA). A DNA mimic with a pseudopeptide backbone", *Chem. Soc. Rev.*, 26:73-78, Abstract Only (1997).

Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Oble, et al. "Focus on TILs: prognostic significance of tumor infiltrating lymphocytes in human melanoma", *Cancer Immunity*, 9: 3, 20 pages (2009).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogle, et al. "Direct measurement of lymphocyte receptor diversity", *Nucleic Acids Research*, 31(22): e139, 6 pages (2003).

Ohlin, Mats, et al. "Light chain shuffling of a high affinity antibody results in a drift in epitope recognition." Molecular Immunology (1996); 33.1: 47-56.

Ohtani. "Focus on TILs: prognostic significance of tumor infiltrating lymphocytes in human colorectal cancer", *Cancer Immunity*, 7: 4, 9 pages (2007).

Okajima et al. "Analysis of T cell receptor Vβ diversity in peripheral CD4+ and CD8+ T lymphocytes in patients with autoimmune thyroid diseases", *Clinical & Experimental Immunology*, 155:166-172 (2008).

Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.

Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

Packer and Muraro. "Optimized clonotypic analysis of T-cell receptor repertoire in immune reconstitution", *Experimental Hematology*, 35(3):516-521 (2007).

Palmowski, et al. "The use of HLA class I tetramers to design a vaccination strategy for melanoma patients", *Immunol Rev.*, 188: 155-163 (2002) (Abstract Only).

Pan, et al. "A new FACS approach isolates hESC derived endoderm using transcription factors", *PLoS One*, 6(3): e17536, 9 pages (2011). doi: 10.1371/journal.pone.0017536.

Panzara, et al., "Analysis of the T cell repertoire using the PCR and specific oligonucleotide primers." Biotechniques (1992); 12(5): 728-735.

Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).

Parameswaran et al. "A pyrosequencing-tailored nucleotide barcode design unveils opportunities for large-scale sample multiplexing", *Nucleic Acids Research*, 35(19): e130, 9 pages (2007).

(56) References Cited

OTHER PUBLICATIONS

Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
PCT/US2009/006053, International Preliminary Report on Patentability dated May 10, 2011, 5 pages.
PCT/US2009/006053, International Search Report dated Jun. 15, 2010, 6 pages.
PCT/US2009/006053, Written Opinion dated Jun. 15, 2010, 4 pages.
PCT/US2010/021264, International Preliminary Report on Patentability mailed Jul. 19, 2011, 5 pages.
PCT/US2010/021264, International Search Report and Written Opinion mailed Apr. 14, 2010, 7 pages.
PCT/US2010/037477, International Preliminary Report on Patentability dated Jan. 4, 2012, 7 pages.
PCT/US2010/037477, International Search Report and Written Opinion mailed Sep. 24, 2010, 10 pages.
PCT/US2011/000791, International Preliminary Report on Patentability dated Nov. 6, 2012, 10 pages.
PCT/US2011/000791, International Search Report and Written Opinion dated Sep. 22, 2011, 13 pages.
PCT/US2011/049012, International Preliminary Report on Patentability dated Feb. 26, 2013, 5 pages.
PCT/US2011/049012, International Search Report and Written Opinion mailed Apr. 10, 2012, 9 pages.
PCT/US2013/028942, International Preliminary Report on Patentability dated May 5, 2015, 9 pages.
PCT/US2013/028942, International Search Report and Written Opinion dated May 9, 2013, 10 pages.
PCT/US2013/035857, International Preliminary Report on Patentability dated Oct. 14, 2014, 8 pages.
PCT/US2013/035857, International Search Report and Written Opinion dated Aug. 7, 2013, 10 pages.
PCT/US2013/040221, International Preliminary Report on Patentability dated Apr. 24, 2014, 41 pages.
PCT/US2013/040221, International Search Report and Written Opinion mailed Sep. 23, 2013, 15 pages.
PCT/US2013/045276, International Preliminary Report on Patentability dated Dec. 16, 2014, 2014, 7 pages.
PCT/US2013/045276, International Search Report and Written Opinion dated Jan. 29, 2014, 11 pages.
PCT/US2013/045994, International Preliminary Report on Patentability dated Dec. 16, 2014, 10 pages.
PCT/US2013/045994, International Search Report and Written Opinion mailed Oct. 25, 2013, 15 pages.
PCT/US2013/051539, International Preliminary Report on Patentability dated Jan. 27, 2015, 7 pages.
PCT/US2013/051539, International Search Report and Written Opinion dated Nov. 27, 2013, 9 pages.
PCT/US2013/054189, International Preliminary Report on Patentability dated Feb. 10, 2015, 7 pages.
PCT/US2013/054189, International Search Report and Written Opinion dated Oct. 21, 2013, 10 pages.
PCT/US2014/030859, International Preliminary Report on Patentability mailed Sep. 15, 2015, 8 pages.
PCT/US2014/030859, International Search Report and Written Opinion mailed Jul. 18, 2014, 14 pages.
PCT/US2014/044971, International Preliminary Examination Report dated Jan. 6, 2016, 12 pages.
PCT/US2014/044971, International Search Report and Written Opinion dated Oct. 30, 2014, 14 pages.
PCT/US2015/018967, International Preliminary Report on Patentability dated Oct. 18, 2016, 11 pages.
PCT/US2015/018967, International Search Report and Written Opinion mailed Jul. 30, 2015, 17 pages.
PCT/US2015/019029, International Preliminary Report on Patentability mailed Sep. 6, 2016, 14 pages.
PCT/US2015/019029, International Search Report and Written Opinion mailed Sep. 15, 2015, 19 pages.
PCT/US2015/023915, International Preliminary Report on Patentability dated Oct. 4, 2016, 7 pages.
PCT/US2015/023915, International Search Report and Written Opinion dated Aug. 26, 2015, 11 pages.
PCT/US2015/058035, International Preliminary Report on Patentability dated May 2, 2017, 8 pages.
PCT/US2015/058035, International Search Report and Written Opinion mailed Jan. 29, 2016, 14 pages.
PCT/US2016/019343, International Preliminary Report on Patentability dated Aug. 29, 2017, 14 pages.
PCT/US2016/019343, International Search Report and Written Opinion mailed Jul. 22, 2016, 23 pages.
PCT/US2016/025535, International Preliminary Report on Patentability dated Oct. 3, 2017, 7 pages.
PCT/US2016/025535, International Search Report and Written Opinion mailed Jul. 11, 2016, 9 pages.
Peet. "The Measurement of Species Diversity", *Annual Review of Ecology and Systematics*, 5: 285-307, Abstract Only (1974).
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Petrosino, et al. "Metagenomic pyrosequencing and microbial identification", *Clin Chem.*, 55(5): 856-866 (2009). doi: 10.1373/clinchem.2008.107565. Epub Mar. 5, 2009.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. and Shih. "Principle and applications of digital PCR", *Expert Rev. Mol. Diagn.*, 4(1):41-47 (2004).
Polz and Cavanaugh. "Bias in Template-to-Product Ratios in Multitemplate PCR", *Applied and Environmental Microbiology*, 64(10): 3724-3730 (1998).
Pop and Salzberg. "Bioinformatics challenges of new sequencing technology", *NIH, Trends Genet.*, 24(3): 142-149 (2008).
Porter, et al. "Chimeric antigen receptor-modified T cells in chronic lymphoid leukemia", *N Engl J Med.*, 365(8):725-33 (2011). doi: 10.1056/NEJMoa1103849. Epub Aug. 10, 2011.
Pourmand, et al. "Direct electrical detection of DNA synthesis", *PNAS*, 103(17): 6466-6470 (2006). Epub Apr. 13, 2006.
Prabakaran et al. "454 antibody sequencing—error characterization and correction", *BMC Research Notes*, 4: 404 (2011).
Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].

(56) References Cited

OTHER PUBLICATIONS

Ramsden, et al. "V(D)J recombination: Born to be wild", *Semin Cancer Biol.*, 20(4): 254-260 (2010). doi: 10.1016/j.semcancer.2010. 06.002. Epub Jul. 1, 2010.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy and Georgiou. "Systems analysis of adaptive immunity by utilization of high-throughput technologies", *Current Opinion in Biotechnology*, 22(4): 584-589 (2011).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reinartz et al. "Massively parallel signature sequencing (MPSS) as a tool for in-depth quantitative gene expression profiling in all organisms", *Brief Funct Genomic Proteomic.*, 1(1): 95-104 (2002).
Reischl and Kochanowski. "Quantitative PCR. A Survey of the Present Technology", Molecular Biotechnology, 3:55-71 (1995).
Ria, et al. "Collagen-specific T-cell repertoire in blood and synovial fluid varies with disease activity in early rheumatoid arthritis", *Arthritis Res Ther.*, 10(6): R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins et al. "Detecting and monitoring lymphoma with high-throughput sequencing" *Oncotarget*, 2:287- 288 (2011).
Robins, et al. "CD4+ and CD8+ T cell β antigen receptors have different and predictable V and J gene usage and CDR3 lengths", *J. Immunol.*, 188: 115.10, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). Epub Oct. 16, 2013.
Robins, et al. "Overlap of the human CD8+ T cell receptor repertoire." Oct. 2010. Poster. 1 page.
Robins, et al. "Effects of aging on the human adaptive immune system revealed by high-throughput DNA sequencing of T cell receptors", *J Immunol.*, 188: 47.16, Abstract (2012).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "The Computational Detection of Functional Nucleotide Sequence Motifs in the Coding Regions of Organisms", *Exp Biol Med*, 233(6): 665-673 (2008).

Robins, H. et al. "Ultra-sensitive detection of rare T cell clones", *Journal of Immunological Methods*, 375(1-2): 14-19 (2012). Epub Sep. 10, 2011.
Robins, H. et al. "Comprehensive assessment of T-cell receptor β-chain diversity in αβ T cells", *Blood*, 114(19):4099-4107 (and Supplemental Materials) (2009).
Robins, H. et al. "Overlap and Effective Size of the Human CD8+ T Cell Receptor Repertoire", *Science Transitional Medicine*, 2(47, 47ra64); and Supplemental Materials, 17 pages (2010).
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Rothberg, et al. "An integrated semiconductor device enabling non-optical genome sequencing", *Nature*, 475(7356): 348-352 (2011). doi: 10.1038/nature10242.
Rougemont, et al. "Probabilistic base calling of Solexa sequencing data", *BMC Bioinformatics*, 9:431, 12 pages (2008).
Ryan et al. "Clonal evolution of lymphoblastoid cell lines", *Laboratory Investigation*, 86(11): 1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).
Schlissel, M.S. et al. "Leukemia and lymphoma: a cost of doing business for adaptive immunity", *Genes Dev.*, 20(12): 1539-1544 (2006).
Schloss, PD et al. Reducing The Effects of PCR Amplification and Sequencing Artifacts on 16S Rrna-Based Studies. PLoS One. Dec. 14, 2011, vol. 6, No. 12; e27310; DOI: 10.1371/journal.pone. 002731 0.
Schmitt et al. "Detection of ultra-rare mutations by next-generation sequencing," *PNAS*, 109(36): 14508-14513 and Supporting Information, 9 pages (2012).
SchØller et al. "Analysis of T cell receptor αβ variability in lymphocytes infiltrating melanoma primary tumours and metastatic lesions", *Cancer Immunol Immunother.* 39(4):239-248 (1994).
Schrappe, M. et al. "Late MRD response determines relapse risk overall and in subsets of childhood T-cell ALL: results of the AIEOP-BFM-ALL 2000 study", *Blood*, 118(8): 2077-2084 (2011).

(56) References Cited

OTHER PUBLICATIONS

Schreiber et al. "Cancer immunoediting: integrating immunity's roles in cancer suppression and promotion", Science, 331(6024): 1565-1570 (2011). doi: 10.1126/science.1203486.
Schwab et al. "CD8+ T-cell clones dominate brain infiltrates in Rasmussen encephalitis and persist in the periphery", Brain, 132:1236-1246 (2009).
Schwartzman, Armin. "Empirical null and false discovery rate inference for exponential families." The Annals of Applied Statistics (2008); 2(4): 1332-1359.
Schweiger et al. "Genome-wide massively parallel sequencing of formaldehyde fixed-paraffin embedded (FFPE) tumor tissues for copy-number and mutation-analysis", PLoS One, 4(5): e5548, 7 pages (2009). doi: 10.1371/journal.pone.0005548. Epub May 14, 2009.
Sebastian, E. et al., "Molecular Characterization of immunoglobulin gene rearrangements in diffuse large B-cell lymphoma", Am. J. Pathol., 181: 1879-1888, Abstract (2012). (Epub: Sep. 28, 2012).
Sehouli et al. "Epigenetic quantification of tumor-infiltrating T-lymphocytes" Epigenetics, 6(2): 236-246 (2011). Epub Feb. 1, 2011.
Seitz, et al. "Reconstitution of paired T cell receptor α- and β-chains from microdissected single cells of human inflammatory tissues", PNAS, 103: 12057-12062 (2006).
Seo, et al. "Four-color DNA sequencing by synthesis on a chip using photocleavable fluorescent nucleotides", PNAS, 102(17): 5926-5931 (2005). Epub Apr. 13, 2005.
Sfanos et al. "Human Prostate-Infiltrating CD8+ T Lymphocytes are Oligoclonal and PD-1+", The Prostate, 69(15): 1694-1703 (2009).
Sfanos et al. "Phenotypic analysis of prostate-infiltrating lymphocytes reveals TH17 and Treg skewing", Clinical Cancer Research, 14(11):3254-3261 (2008). doi: 10.1158/1078-0432.CCR-07-5164.
Shen et al. "Comparing platforms for C. elegans mutant identification using high-throughput whole-genome sequencing", PLoS One, 3(12):e4012, 6 pages (2008).
Shendure and Ji. "Next-generation DNA sequencing", Nature Biotechnology, 26(10):1135-1145 (2008).
Shendure, et al. "Advanced sequencing technologies: methods and goals", Nat Rev Genet., 5(5): 335-344 (2004).
Sherwood, A. et al. "Deep Sequencing of the Human TCRγ and TCRβ Repertoires Suggests that TCR β Rearranges After αβ and γδT Cell Commitment", Science Translational Medicine, Sci. Transl. Med., 3(90): 1-7 (2011).
Sherwood, et al. "New Technologies for Measurements of Tumor Infiltrating Lymphocytes", Presented Nov. 7, 2012 Moscone Center, Exhibit Halls ABC.
Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.
Shino, et al. "Usefulness of immune monitoring in lung transplantation using adenosine triphosphate production in activated lymphocytes", The Journal of Heart and Lung Transplant, 31: 996-1002 (2012).
Shiroguchi et al. "Digital RNA sequencing minimizes sequence-dependent bias and amplification noise with optimized single-molecule barcodes", PNAS, 109(4): 1347-1352 (2012).
Shoemaker et al. "Quantitative phenotypic analysis of yeast deletion mutants using a highly parallel molecular bar-coding strategy," Nature Genetics, 14(4): 450-456 (1996).
Shumaker, et al. "Mutation detection by solid phase primer extension", Hum Mutat., 7(4): 346-354, Abstract Only (1996).
Sia, et al. "Microfluidic devices fabricated in poly(dimethylsiloxane) for biological studies", Electrophoresis, 24(21): 3563-3576, Abstract Only (2003).
Sims, et al. "Fluorogenic DNA sequencing in PDMS microreactors", Nat Methods, 8(7): 575-580 (2011). doi: 10.1038/nmeth.1629.
Sims, et al. "MHC-peptide tetramers for the analysis of antigen-specific T cells", Expert Rev Vaccines, 9(7): 765-774 (2010). doi: 10.1586/erv.10.66.
Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", Hepatology, 33(5):1288-1298 (2001).
Singapore Application No. 11201407888R, Written Opinion mailed Aug. 14, 2015, 12 pages.
Sint, D., et al. "Advances in multiplex PCR: balancing primer efficiencies and improving detection success", Methods in Ecology and Evolution, 3(5): 898-905 (2012).
Skulina et al. "Multiple Sclerosis: Brain-infiltrating CD8+ T cells persist as clonal expansions in the cerebrospinal fluid and blood", PNAS, 101(8):2428-2433 (2004).
Smith et al. "Rapid generation of fully human monoclonal antibodies specific to a vaccinating antigen", Nature Protocols, 4(3): 372-384 and Corrigenda (2009).
Smith et al. "Rapid whole-genome mutational profiling using next-generation sequencing technologies", Genome Research, 18: 1638-1642 (2008).
Smith, et al. "Comparison of biosequences", Advances in Applied Mathematics, 2: 482-489 (1981).
Sobrino, et al. "SNPs in forensic genetics: a review on SNP typing methodologies", Forensic Sci Int., 154(2-3): 181-194, Abstract Only (2005). Epub Jan. 11, 2005.
Sotomayor, et al., "Conversion of tumor-specific CD4+ T-cell tolerance to T-cell priming through in vivo ligation of CD40." Nature Medicine (Jul. 1999); 5(7): 780-787.
Spreafico, et al. "A circulating reservoir of pathogenic-like CD4+ T cells shares a genetic and phenotypic signature with the inflamed synovial micro-environment", Ann Rheum Dis., 0: 1-7 (2014). doi: 10.1136/annrheumdis-2014-206226. [Epub ahead of print].
Sramkova, et al. "Detectable minimal residual disease before allogeneic hematopoietic stem cell transplantation predicts extremely poor prognosis in children with acute lymphoblastic leukemia", Pediatr. Blood Cancer, 48(1):93-100 (2007).
Srinivasan et al. "Effect of fixatives and tissue processing on the content and integrity of nucleic acids", Am J Pathol., 161(6): 1961-1971 (2002).
Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.
Steenbergen, et al. "Distinct ongoing Ig heavy chain rearrangement processes in childhood B-precursor acute lymphoblastic leukemia", Blood, 82(2):581-589 (1993).
Steenbergen, et al. "Frequent ongoing T-cell receptor rearrangements in childhood B-precursor acute lymphoblastic leukemia: implications for monitoring minimal residual disease", Blood, 86(2): 692-702, Abstract Only (1995).
Stemmer, et al. "Single-step assembly of a gene and entire plasmid from large numbers of oligodeoxyribonucleotides", Gene, 164(1): 49-53 (1995).
Steward et al. "A polymerase chain reaction study of the stability of Ig heavy-chain and T-cell receptor delta gene rearrangements between presentation and relapse of childhood B-lineage acute lymphoblastic leukemia", Blood, 83(5):1355-1362 (1994).
Stewart and Schwartz. "Immunoglobulin V regions and the B cell", Blood, 83(7): 1717-1730 (1994).
Stickler, et al. "An in vitro human cell-based assay to rank the relative immunogenicity of proteins", Toxicol Sci., 77(2): 280-289 (2004). Epub Dec. 22, 2003.
Stiller et al. "Direct multiplex sequencing (DMPS)—a novel method for targeted high-throughput sequencing of ancient and highly degraded DNA", Genome Research, 19: 1843-849 (2009).
Straten, Per thor, et al. "T-cell clonotypes in cancer", Journal of Translational Medicine, 2(1): 11, 10 pages (2004).
Stratton. "Exploring the genomes of cancer cells: progress and promise", Science, 331(6024): 1553-1558 (2011). doi: 10.1126/science.1204040.
Striebich, et al. "Selective Accumulation of Related CD41 T Cell Clones in the Synovial Fluid of Patients with Rheumatoid Arthritis", J Immunol., 161(8): 4428-4436 (1998).
Struyk et al. "T cell receptors in rheumatoid arthritis", Arthritis & Rheumatism, 38(5):577-589 (1995).

(56) References Cited

OTHER PUBLICATIONS

Sumida et al. "T cell receptor repertoire of infiltrating T cells in lips of Sjögren's syndrome patients", *J Clin Invest.*, 89:681-685 (1992).
Sumida et al. "T cell receptor Vα repertoire of infiltrating T cells in labial salivary glands from patients with Sjögren's syndrome", *J Rheumatol.*, 21:1655-1661 (1994).
Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.
Szczepanski et al. "Why and how to quantify minimal residual disease in acute lymphoblastic leukemia?", *Leukemia*, 21(4):622-626 (2007). Epub Feb. 15, 2007.
Szczepanski et al., "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).
Szczepanski, T. et al. "Minimal residual disease in leukemia patients", *Lancet Oncology*, 2:409-417 (2001).
Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.
Tackenberg et al. "Clonal expansions of CD4+ β helper T cells in autoimmune myasthenia gravis", *European Journal of Immunology*, 37(3):849-863 (2007).
Tajiri et al. "Cell-microarray analysis of antigen-specific B-cells: single cell analysis of antigen receptor expression and specificity", *Cytometry Part A*, 71A: 961-967 (2007).
Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).
Tam, James P. "Synthetic peptide vaccine design: synthesis and properties of a high-density multiple antigenic peptide system." Proceedings of the National Academy of Sciences (1988); 85.15: 5409-5413.
Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).
Taubenheim et al. "High Rate of Antibody Secretion Is not Integral to Plasma Cell Differentiation as Revealed by XBP-1 Deficiency", *The Journal of Immunology*, 189: 3328-3338 (2012).
Tautz, et al. "Cryptic simplicity in DNA is a major source of genetic variation", *Nature*, 322(6080): 652-656 (1986).
Tawfik, et al. "Man-made cell-like compartments for molecular evolution", *Nat Biotechnol.*, 16(7): 652-656, Abstract Only (1998).
Ten Bosch et al. "Keeping Up With the Next Generation Massively Parallel Sequencing in Clinical Diagnostics", *Journal of Molecular Diagnostics*, 10(6): 484-492 (2008).
Tewhey, R. et al. "Corrigendum: Microdroplet-based PCR enrichment for large-scale targeted sequencing", *Nature Biotechnology*, 28(2):178, 1 page (2010).
Thiel, et al. "Antigen-specific cytometry—new tools arrived!", *Clin Immunol.*, 111(2): 155-161, Abstract Only (2004).
Thornhill et al. "A comparison of different lysis buffers to assess allele dropout from single cells for preimplantation genetic diagnosis", *Prenatal Diagnosis*, 21:490-497 (2001).
Tokimitsu et al. "Single lymphocyte analysis with a microwell array chip", *Cytometry Part A*, 71A:1003-1010 (2007).
Toriello et al. "Integrated microfluidic bioprocessor for single-cell gene expression analysis", *PNAS*, 105(51): 20173-20178 (2008).
Triebel, F. et al. "A Unique V-J-C-Rearranged Gene Encodes A γ Protein Expressed on the Majority of CD3+ T Cell Receptor -a/fr Circulating Lymphocytes", *J. Exp. Med.*, 167:694-699 (1988).

Tsai et al. "Discovery of rare mutations in populations: TILLING by sequencing", Plant Physiology, 156(3): 1257-1268 (and Supplemental Data) (2011).
Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.
Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).
Turcotte and Rosenberg. "Immunotherapy for metastatic solid cancers", *Adv Surg.*, 45: 341-360 (2011).
UK combined search and examination report dated Mar. 20, 2013 for GB 1300533.5.
UK Combined Search Report and Office action dated May 27, 2011 for UK application No. GB1105068.9.
UK Combined Search Report and Office action dated Jun. 29, 2012 for UK application No. GB1209668.1.
UK Search Report and office action dated Jan. 13, 2012 for UK application No. GB1120209.0.
UK Search Report and office action dated Jul. 7, 2010 for UK application No. GB1009641.0.
Umibe et al. "Clonal expansion of T cells infiltrating in the airways of non-atopic asthmatics", *Clinical & Experimental Immunology*, 119(3):390-397 (2000).
Unrau and Deugau. "Non-cloning amplification of specific DNA fragments from whole genomic DNA digests using DNA 'indexers'", *Gene.*, 145(2): 163-169, Abstract Only, 2 pages (1994).
Uppaluri et al. "Focus on TILs: prognostic significance of tumor infiltrating lymphocytes in head and neck cancers", *Cancer Immunity*, 8:16, 10 pages (2008).
Urban, et al. "A systematic and quantitative analysis of PCR template contamination", *J Forensic Sci.*, 45(6): 1307-1311 (2000).
Van Der Velden, V.H.J., et al. "Analysis of minimal residual disease by Ig/TCR gene rearrangements: guidelines for interpretation of real-time quantitative PCR data," *Leukemia*, 21:604-611 (2007).
Van Der Velden, V.H.J., et al. "Detection of minimal residual disease in hematologic malignancies by realtime quantitative PCR: principles, approaches, and laboratory aspects," *Leukemia*, 17:1013-1034 (2003).
Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).
Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMH4-CT98-3936", *Leukemia*, 17:2257-2317 (2003).
Van Dongen, J.J.M. et al. "Prognostic value of minimal residual disease in acute lymphoblastic leukaemia in childhood", *The Lancet*, 352:1731-1738 (1998).
Van Heijst, J.W.J., et al., "Quantitative assessment of T-cell repertoire recovery after hematopoietic stem cell transplantation." Nat Med. (2013); 19(3): 372-377.
Varley and Mitra. "Nested patch PCR enables highly multiplexed mutation discovery in candidate genes", *Genome Research*, 18: 1844-1850 (2008).
Venturi, et al. "A mechanism for TCR sharing between T cell subsets and individuals revealed by pyrosequencing", *J Immunol.*, 186(7): 4285-4294 (2011). doi: 10.4049/jimmunol.1003898. Epub Mar. 7, 2011.
Venturi, V. et al. "TCR β-Chain Sharing in Human CD8+ T Cell Responses to Cytomegalovirus and EBV[1]", *The Journal of Immunology*, 181:7853-7862 (2008).
Vester, et al. "LNA (locked nucleic acid): high-affinity targeting of complementary RNA and DNA", *Biochemistry*, 43(42): 13233-13241, Abstract Only (2004).
Vlassov, et al. "Circulating nucleic acids as a potential source for cancer biomarkers", *Curr Mol Med.*, 10(2): 142-165 (2010).

(56) References Cited

OTHER PUBLICATIONS

Vogelstein et al. "Cancer genome landscapes", *Science*, 339(6127): 1546-1558 (2013). doi: 10.1126/science.1235122.
Wälchli, et al. "A practical approach to T-cell receptor cloning and expression", *PLoS One*, 6(11): e27930, 11 pages (2011). doi: 10.1371/journal.pone.0027930. Epub Nov. 21, 2011.
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, et al. "Balanced-PCR amplification allows unbiased identification of genomic copy changes in minute cell and tissue samples", *Nucleic Acids Research*, 32(9): e76, 10 pages (2004).
Wang, et al. "High throughput sequencing reveals a complex pattern of dynamic interrelationships among human T cell subsets", *PNAS*, 107(4): 1518-1528 (2010).
Wang, X. et al. "Quantitative Measurement of Pathogen Specific Human Memory T Cell Repertoire Diversity using a CDR3 B-Specific Microarray", *BMC Genomics*, 8(329): 1-13 (2007).
Warren et al. "Exhaustive T-cell repertoire sequencing of human peripheral blood samples reveals signatures of antigen selection and a directly measured repertoire size of at least 1 million clonotypes", *Genome Res.*, 21(5): 790-797 (2011). Epub Feb. 24, 2011.
Warren et al. "Profiling model T-cell metagenomes with short reads", *Bioinformatics*, 25(4):458-464 (2009).
Weiss et al. "Clonal Rearrangements of T-Cell Receptor Genes in Mycosis Fungoides and Dermatopathic Lymphadenopathy", *The New England Journal of Medicine*, 313(9):539-544 (1985).
Welch and Link. "Genomics of AML: clinical applications of next-generation sequencing", *American Society of Hematology*, 2011: 30-35 (2011). doi: 10.1182/asheducation-2011.1.30.
Wells, et al. "Rapid evolution of peptide and protein binding properties in vitro", *Curr Opin Biotechnol.*, 3(4): 355-362, Abstract Only (1992).
Wells, et al. "Strategies for preimplantation genetic diagnosis of single gene disorders by DNA amplification", *Prenatal Diagnosis*, 18(13): 1389-1401 (1998).
Weng, et al. "Minimal residual disease monitoring with high-throughput sequencing of T cell receptors in cutaneous T cell lymphoma", Sci Transl Med., 5(214):214ra171 (2013).
Westermann and Pabst. "Distribution of lymphocyte subsets and natural killer cells in the human body", *Clin Investig.*, 70(7): 539-544 (1992).
Wetmur and Chen. "An emulsion polymerase chain reaction-based method for molecular haplotyping", *Methods in Molecular Biology*, 410: 351-361 (1996).
Wetmur and Chen. "Linking emulsion PCR haplotype analysis", chapter 11, Park, D.J. (ed.), *PCR Protocols, Methods in Molecular Biology*, 687: 165-175 (2011).
Wetmur et al. "Molecular haplotyping by linking emulsion PCR: analysis of paraoxonase 1 haplotypes and phenotypes", *Nucleic Acids Research*, 33(8):2615-2619 (2005).
Weusten, et al. "Principles of quantitation of viral loads using nucleic acid sequence-based amplification in combination with homogeneous detection using molecular beacons", Nucleic Acids Res., 30(6): e26, 7 pages (2002).
White et al. "High-throughput microfluidic single-cell RT-qPCR", *PNAS*, 108(34): 13999-14004 (2011).
Whiteford, et al. "Swift: primary data analysis for the Illumina Solexa sequencing platform", *Bioinformatics*, 25(17): 2194-2199 (2009). doi: 10.1093/bioinformatics/btp383. Epub Jun. 23, 2009.
Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (May 2001); 158(5): 1851-1857.
Wilson-Lingardo et al., "Deconvolution of Combinatorial Libraries for Drug Discovery: Experimental Comparison of Pooling Strategies." J. Med. Chem., (1996); 39 (14): 2720-2726.

Wlodarski et al. "Molecular strategies for detection and quantitation of clonal cytotoxic T-cell responses in aplastic anemia and myelodysplastic syndrome", *Blood*, 108(8):2632-2641 (2006).
Wlodarski et al. "Pathologic clonal cytotoxic T-cell responses: nonrandom nature of the T-cell-receptor restriction in large granular lymphocyte leukemia", *Blood*, 106:2769-2779 (2005).
Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.
Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", *Nucleic Acids Research*, 38(14): e151, 11 pages (2010). doi: 10.1093/nar/gkq510. Epub Jun. 4, 2010.
Woodsworth, Daniel J., et al., "Sequence analysis of T-cell repertoires in health and disease." Genome Medicine (2013); 5: 98, 13 pages.
Wrammert et al. "Rapid cloning of high-affinity human monoclonal antibodies against influenza virus", Nature, 453: 667-672 (2008).
Wu et al. "Focused Evolution of HIV-1 Neutralizing Antibodies Revealed by Structures and Deep Sequencing", *Science*, 333: 1593-1602 (2011).
Wu, et al. "High-throughput sequencing detects minimal residual disease in acute T lymphoblastic leukemia", Sci Transl Med., 4 (134): 151-157, 134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, H.D. et al. "The Lymphocytic Infiltration in Calcific Aortic Stenosis Predominantly Consists of Clonally Expanded T Cells", *The Journal of Immunology*, 178(8): 5329-5339 (2007).
Wu, Y-C. et al. "High-throughput immunoglobulin repertoire analysis distinguishes between human IgM memory and switched memory B-cell populations", *Blood Journal*, 116(7): 1070-1078, 22 pages (2010).
Xie, Yang, et al., "A note on using permutation-based false discovery rate estimates to compare different analysis methods for microarray data." Bioinformatics (2005); 21.23: 4280-4288.
Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.
Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.
Xu, W. et al. "A Novel Universal Primer-Multiplex-PCR Method with Sequencing Gel Electrophoresis Analysis", *PLoS One*, 7(1): e22900, 10 pages (2012).
Yagi, et al., "Detection of clonotypic IGH and TCR rearrangements in the neonatal blood spots of infants and children with B-cell precursor acute lymphoblastic leukemia." Blood (2000); 96(1): 264-268.
Yao, et al. "Analysis of the CDR3 length repertoire and the diversity of TCRα chain in human peripheral blood T Lymphocytes", Cell Mol Immunol., 4(3): 215-220 (2007).
Yassai, M.B. et al. "A clonotype nomenclature for T cell receptors", *Immunogenetics*, 61:493-502 (2009).
Yeh, et al. "Regulating DNA translocation through functionalized soft nanopores", *Nanoscale*, 4(8): 2685-4693, Abstract Only (2012). doi: 10.1039/c2nr30102d. Epub Mar. 15, 2012.
Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).
Yon and Fried. "Precise gene fusion by PCR", *Nucleic Acids Research*, 17(12):4895, 1 page (1989).

(56) References Cited

OTHER PUBLICATIONS

York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.

Yu and Fu. "Tumor-infiltrating T lymphocytes: friends or foes?", *Lab Invest.*, 86(3): 231-245 (2006).

Zagnoni, et al. "Droplet Microfluidics for High-throughput Analysis of Cells and Particles", *Methods in Cell Biology*, Chapter 2, 102: 23-48 (2011).

Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).

Zehentner et al. "Minimal Disease Detection and Confirmation in Hematologic Malignancies: Combining Cell Sorting with Clonality Profiling", *Clinical Chemistry*, 52(3): 430-437 (2006).

Zeng et al. "High-performance single cell genetic analysis using microfluidic emulsion generator arrays", *Anal. Chem.*, 82(8):3183-3190 (2010).

Zhong, Q. et al. "Multiplex digital PCR: breaking the one target per color barrier of quantitative PCR", Lab Chip, 11:2167-2174 (2011).

Zhou et al. "High throughput analysis of TCR-β rearrangement and gene expression in single cells", *Laboratory Investigation*, 86: 314-321 (2006).

Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.

Zimmerman and Mannhalter. "Technical aspects of quantitative competitive PCR", *Biotechniques*, 21: 268-279 (1996).

* cited by examiner

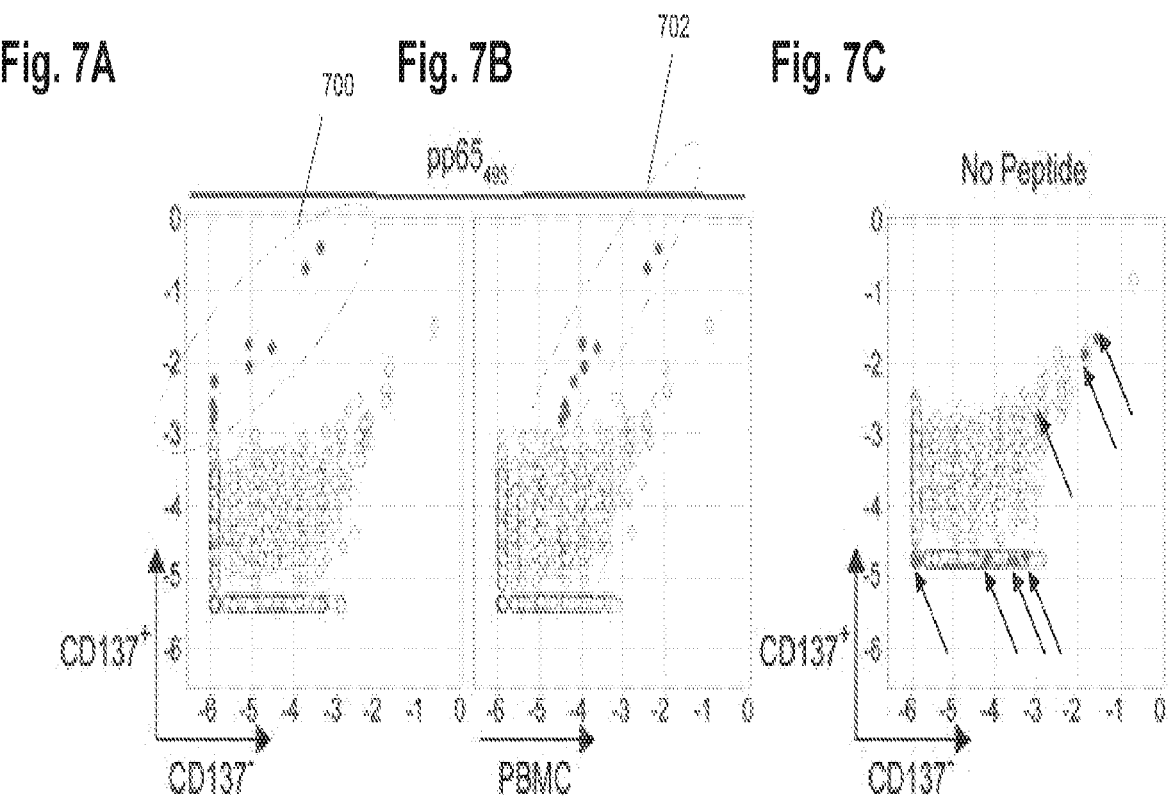

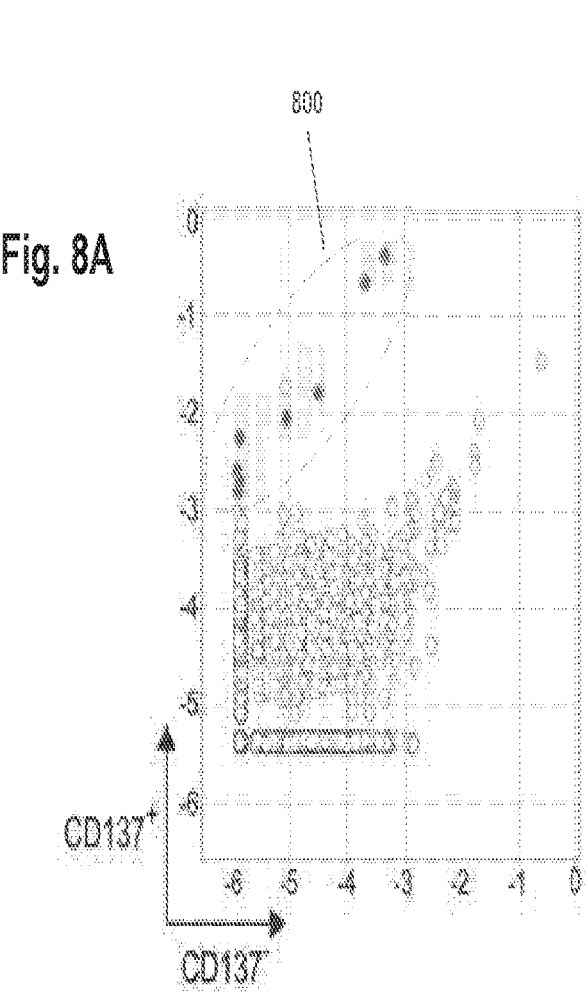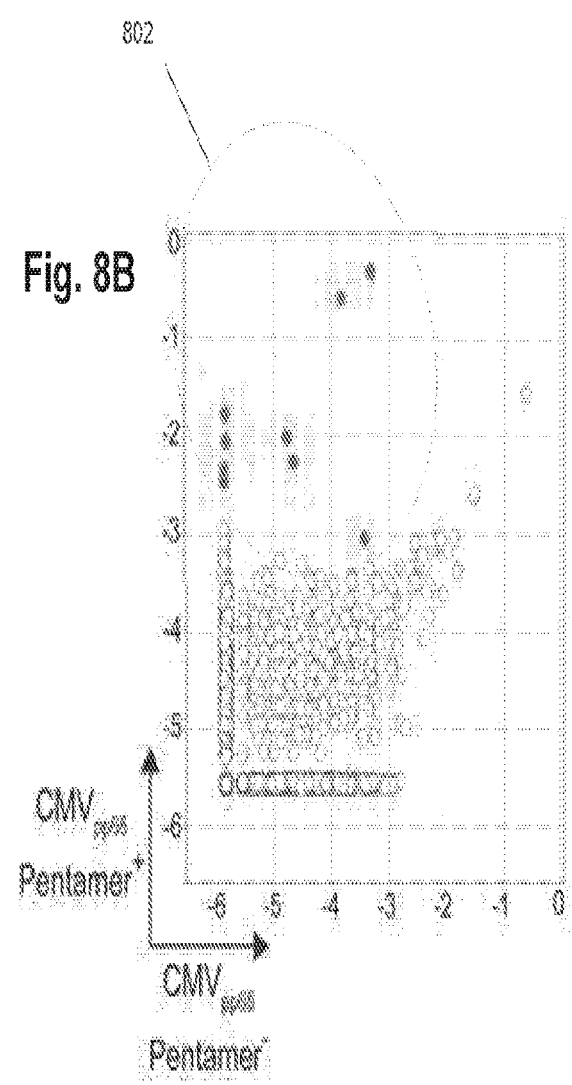

DETERMINING ANTIGEN-SPECIFIC T-CELLS

CROSS-REFERENCE TO RELATED APPLICATIONS

This application is a divisional of and claims priority to U.S. patent application Ser. No. 14/242,520, filed Apr. 1, 2014, which is hereby incorporated by reference in its entirety.

BACKGROUND OF THE INVENTION

Many crucial immune functions are mediated by T cell receptors (TCRs), which comprise a and R subunits that together bind to a complex consisting of an antigenic peptide and major histocompatibility complex (MHC) molecules. It is believed that several important diseases arise from aberrant T cell function: For example, cancers are thought to arise from a failure of immune surveillance, that is, the T cell function of detecting and destroying clones of transformed cells before they grow into tumors; and autoimmune diseases are thought to arise from an over active or aberrant response of T cells to self antigens, Abbas et al, Cellular and Molecular Immunology, Fourth Edition (W.B. Saunders Company, 2000). Consequently, there has been interest both in identifying and tracking antigen-specific T cells and in harnessing T cell functions in several therapeutic approaches for the treatment both cancer and autoimmune diseases, e.g. Molloy et al, Current Opinion in Pharmacology, 5: 438-443 (2005); Morgan et al, Science, 314: 126-129 (2006); Turcotte and Rosenberg, Adv. Surg., 45: 341-360 (2011). Several challenges are posed by these interests: Current techniques for identifying and tracking antigen-specific T cells, especially on a large scale, are difficult and expensive, and likewise, current techniques for identifying and isolating paired TCRα and TCRβ subunits that form a functional receptor are difficult and expensive. In regard to detecting antigen-specific T cells, the use of direct multimer staining requires laborious development of specific HLA-restricted reagents, and other assays, such as ELISPOT, intracellular cytokine staining, and proliferation assays, enumerate antigen-specific T cells based on detection of activation following stimulation of the T cells in vitro with antigen, e.g. Gratama et al, Cytometry A, 73A: 971-974 (2008). In regard to isolating functional pairs of TCR chains, typically a T cell of interest is identified and clonally expanded to enable isolation and analysis of nucleic acids encoding each subunit. Even for a common disease antigen, such as MART-1 in melanoma, the process of single cell analysis, cloning and receptor isolation must be repeated for each patient.

Recently, diagnostic and prognostic applications have been proposed that use large-scale DNA sequencing as the per-base cost of DNA sequencing has dropped and sequencing techniques have become more convenient, e.g. Welch et al, Hematology Am. Soc. Hematol. Educ. Program, 2011: 30-35; Cronin et al, Biomark Med., 5: 293-305 (2011); Palomaki et al, Genetics in Medicine (online publication 2 Feb. 2012). In particular, profiles of nucleic acids encoding immune molecules, such as T cell or B cell receptors, or their components, contain a wealth of information on the state of health or disease of an organism, so that diagnostic and prognostic indicators based on the use of such profiles are being developed for a wide variety of conditions, Faham and Willis, U.S. patent publication 2010/0151471; Freeman et al, Genome Research, 19: 1817-1824 (2009); Boyd et al, Sci. Transl. Med., 1(12): 12ra23 (2009); He et al, Oncotarget (Mar. 8, 2011). Current sequence-based profiles of immune repertoires consist of nucleic acids encoding only single receptor chains; thus, potentially useful information from correctly paired TCRα and TCRβ chains chains is not available.

In view of the above, it would be highly useful for cancer, infectious disease and autoimmune disease treatment if there were available convenient methods for determining functional immune receptors from nucleic acids encoding subunits that have been separately extracted and sequenced.

SUMMARY OF THE INVENTION

The present invention is drawn to methods for determining T cell receptors from subunits selected from separate libraries, particularly antigen-specific T cell receptors. The invention is exemplified in a number of implementations and applications, some of which are summarized below and throughout the specification.

In one aspect, the invention includes methods for determining antigen-specific T cells in a tissue sample comprise steps of (a) reacting under activation conditions in a reaction mixture a tissue sample comprising T cells to an antigen; (b) sorting T cells from the reaction mixture into a subset of antigen-specific T cells and/or activated T cells and a subset of non-antigen-specific T cells and/or unactivated T cells; (c) sequencing recombined nucleic acids encoding a T-cell receptor chain or a portion thereof from a sample of T cells from the antigen-specific T cells and/or activated T cells to provide sequence reads from which clonotypes are determined; (d) sequencing recombined nucleic acids encoding a T-cell receptor chain or a portion thereof from a sample of T cells from the non-antigen-specific T cells and/or unactivated T cells to provide sequence reads from which clonotypes are determined; and (e) determining antigen-specific T cells in the tissue sample as T cells whose clonotype frequencies increase in the subset of sorted antigen-specific and/or activated T cells relative to the frequencies of the same clonotypes in the reaction mixture or the subset of sorted non-antigen-specific and/or unactivated T cells.

In another aspect, the invention includes methods of determining receptors of antigen-specific T cells in a tissue sample comprising the following steps: (a) forming a plurality of subsets from a tissue sample containing T cells; (b) reacting under activation conditions the T cells of each subset to an antigen; (c) isolating the antigen-specific T cells of each subset; (d) sequencing recombined nucleic acids encoding T-cell receptor α chains in each subset to provide sequence reads from which α chain clonotypes are determined; (c) sequencing recombined nucleic acids encoding T-cell receptor R chains in each subset to provide sequence reads from which β chain clonotypes are determined; and (f) identifying as antigen-specific T-cell receptors with those pairs of α chain clonotypes and β chain clonotypes that for every subset (i) either both the α chain clonotype and β chain clonotype are present in a subset or neither are present in a subset, and (ii) both the α chain clonotype and β chain clonotype are present in at least one subset and the α chain clonotype and β chain clonotype are not present in at least one subset.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 6A shows clonotype frequencies from CMV pp65495 pentamer+ versus pentamer-CD8+ T cells from a characterized CMV responder.

The 8 dots (enclosed in dashed elipse 600) indicate clonotypes greater than 10-fold enriched and exceeding a 20-cell equivalent minimum frequency threshold in the sorted (pentamer+) population. FIG. 6B shows that all 8 clonotypes identified in FIG. 6A are enriched in (unsorted) PBMCs from the same individual. The dots enclosed by the dashed ellipse (602) indicate clonotypes identified in FIG. 6A.

FIG. 7A-FIG. 7C show data for identification of CMV pp65495-specific T cell clonotypes from sorted responding cells following peptide incubation. Clonotype frequencies from sorted responding CD37+ cells following CMV pp65$_{495}$ peptide incubation versus either sorted non-responding CD137– cells (FIG. 7A) or unsorted PBMCs (FIG. 7B). The 9 data points enclosed by dashed ellipse (700) in panel A indicate clonotypes greater than 10-fold enriched and exceeding a 20-cell equivalent minimum frequency threshold in the sorted (CD137+) population. Data points enclosed in dashed ellipse (702) in panel B indicate those clonotypes identified in panel A. Clonotypes identified in panel A are not enriched in sorted CD137+ cells versus CD137– T cells (FIG. 7C arrows indicating data points corresponding to those enclosed by ellipse in FIG. 7A and FIG. 7B) following incubation without peptide.

FIG. 8A-FIG. 8B illustrate the overlap between clonotypes identified in pentamer-based and CD137-based assays. In FIG. 8A, the plot shows clonotype frequencies of the 8 clonotypes (enclosed by dashed ellipse 800) identified in the pentamer analyses in the clonotype profiles of CD137+ responding cells following CMV pp65$_{495}$ peptide incubation versus sorted non-responding CD137– cells. In FIG. 8B, the plot shows clonotype frequencies of the 9 clonotypes (enclosed by dashed ellipse 802) identified in the CD137 assay analyses in the clonotype profiles of sorted CMV pp65$_{495}$ pentamer+ cells versus pentamer– cells. 8/9 of these clonotypes are overlapping with those identified in FIG. 8A.

In FIG. 9A, clonotype frequencies from sorted proliferating CD8+ T cells following CMV pp65$_{495}$ peptide incubation at day 6 versus fresh unsorted PBMCs. The 16 data points (enclosed by dashed elipse 900) indicate clonotypes greater than 10-fold enriched and exceeding 1/10,000 minimum frequency threshold in the sorted proliferating cells. FIG. 9B shows data of clonotype frequencies from sorted proliferating CD8+ T cells following incubation without peptide at day 6 versus fresh unsorted PBMCs. Clonotypes (represented by data points enclosed by dashed elipses (902) are those identified in FIG. 9A. FIG. 9C shows data of clonotype frequencies from CMV pp65495 pentamer+ versus pentamer– CD8+ T cells. Dashed elipses (904) and arrow (906) indicate the 16 clonotypes identified in the proliferation assay whose results are represented in FIG. 9A with those clonotypes identified in the CMV pp65$_{495}$ pentamer+ versus pentamer– CD8+ T cell comparison. FIG. 9D shows data of clonotype frequencies from CMV pp65$_{495}$ pentamer+ versus pentamer– CDK+ cells. Data points enclosed by dashed elipses (908) and designated by arrows (910) indicate the 25 clonotypes identified in a variant of the proliferation assay described above with those clonotypes identified in the CMV pp65$_{495}$ pentamer+ versus pentamer– CD8-4 T cell comparison. In this assay a pool of 138 overlapping peptides from pp65 was used instead of the single pp65$_{495}$ peptide.

DETAILED DESCRIPTION OF THE INVENTION

Figure 1A:
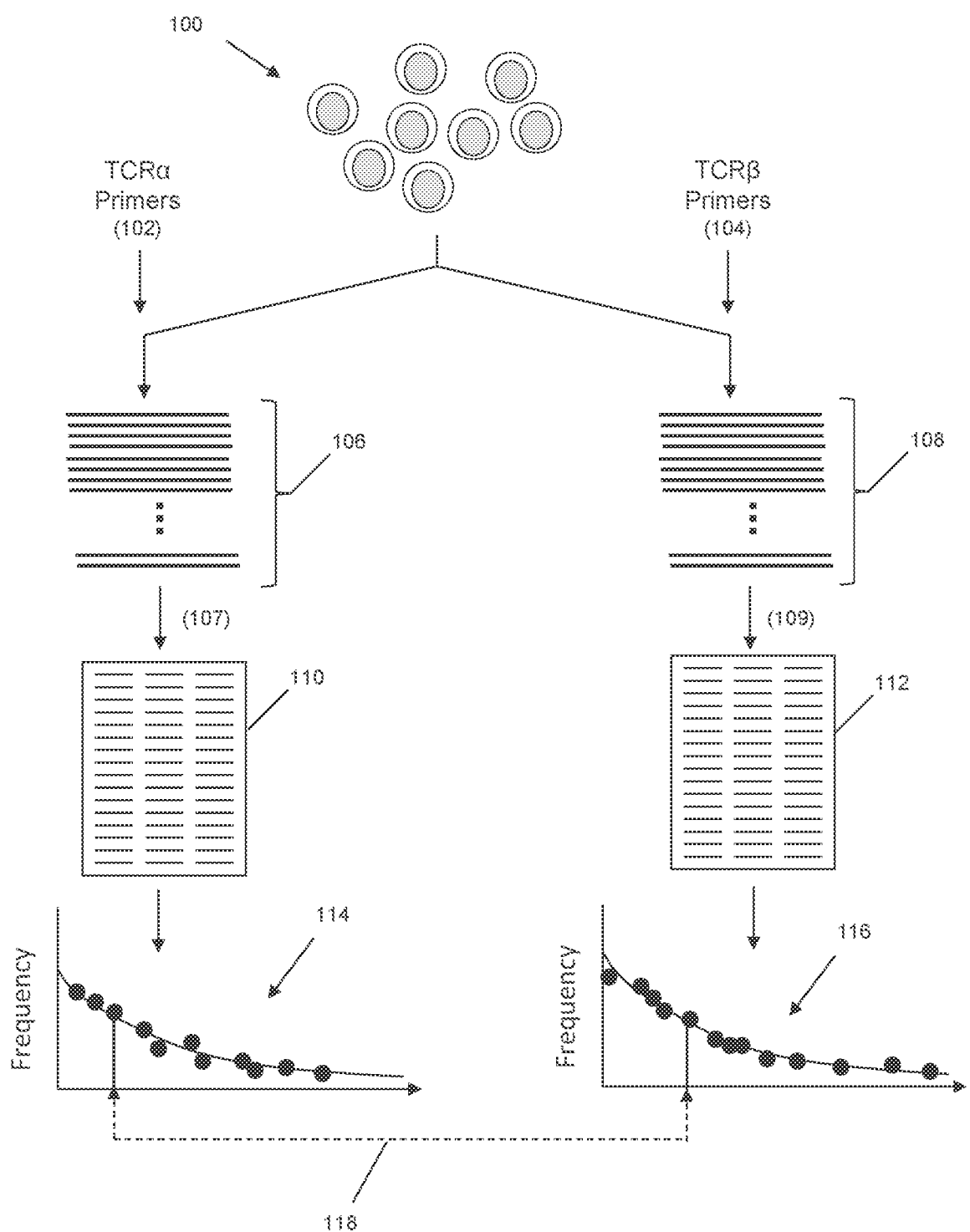
FIG. 1A illustrates diagrammatically steps of one embodiment of the invention for matching TCRα and TCRβ chains from separately sequenced molecules.

The practice of the present invention may employ, unless otherwise indicated, conventional techniques and descriptions of molecular biology (including recombinant techniques), bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals.

Identifying Paired T-Cell Receptor Chains without Antigen-Specific Selection In one aspect, the invention provides methods for matching pairs of immune receptor chains from populations of their encoding nucleic acids that have been sequenced. In accordance with one embodiment of the invention, nucleic acid populations encoding repertoires of heavy chain variable regions and light chain variable regions are sequenced so that two separate lists of sequences are formed without any correspondence between members of each list. This may be achieved by carrying out separate sequencing operations, or runs, for each chain, or it may be accomplished by carrying out a single sequence run with the nucleic acids tagged according to the identity of the type of chain it encodes. In accordance with another embodiment of the invention, nucleic acid populations encoding repertoires of T cell receptor alpha (TCRα) chains and T cell receptor beta (TCRβ) chains are sequenced, so that two separate lists of sequences are formed without any correspondence between members of each list. In accordance with another embodiment of the invention, nucleic acid populations encoding repertoires of T cell receptor gamma (TCRγ) chains and T cell receptor delta (TCRδ) chains are sequenced, so that two separate lists of sequences are formed without any correspondence between members of each list. As above, this may be achieved by carrying out separate sequencing runs for each chain, or it may be accomplished by carrying out a single sequence run with the nucleic acids tagged according to the identity of the type of chain it encodes (that is, either TCRα and TCRβ, or TCRγ and TCRδ, respectively). In the latter embodiments, two approaches may be followed for matching or pairing TCRα and TCRβ (or TCRγ and TCRδ) chains into chains that are functional, for example, because they originate from the same T cell. In a first approach, the frequencies of each encoding nucleic acid are determined and TCRα chains and TCRβ chains whose encoding nucleotide sequences have the same frequencies are paired to form a functional, or reconstituted, TCR. TCRγ and TCRδ chains may be matched by the same process. In a second approach, which is applicable to matching all three types of immune receptor pairs, a lymphocyte population is repeatedly divided into a plurality of subsets. Such subsets may be obtained by aliquoting a tissue sample into separate reaction vessels or chambers. Separately from each of a portion, or subpopulation, of the subsets, nucleic acids encoding the two different immune receptor chains are extracted and sequenced, so that two separate lists of sequences are formed without any correspondence between members of each list. As described above, this may be achieved by carrying out separate sequencing runs for each chain, or it may be accomplished by carrying out a single sequence run with the nucleic acids tagged according to the identity of the type of chain it encodes. To illustrate by an example, if a sample containing T cells or B cells is aliquotted into 100 sub-samples, so that on average each aliquot contains a subset consisting of about 1/100 of the total number of T cells or B cells in the original sample, then 20 such subsets may be randomly selected as a portion of the total number of subsets. (Such portion could be any number greater than one and less than 100, although as described more fully below, a number in the range of from 10 to 20 is a good trade off between amount of sequencing required and likelihood of identifying receptor pairs present at a frequency of interest). In one embodiment, a plurality of subsets is in the range of from 20 to 2000 and a portion of subsets thereof is in the range of from 10 to 50. In another embodiment, a portion of subsets is in the range of from 10 to 20. Examples of the above embodiments are illustrated in FIGS. 1A and 1B.

Figure 1B:
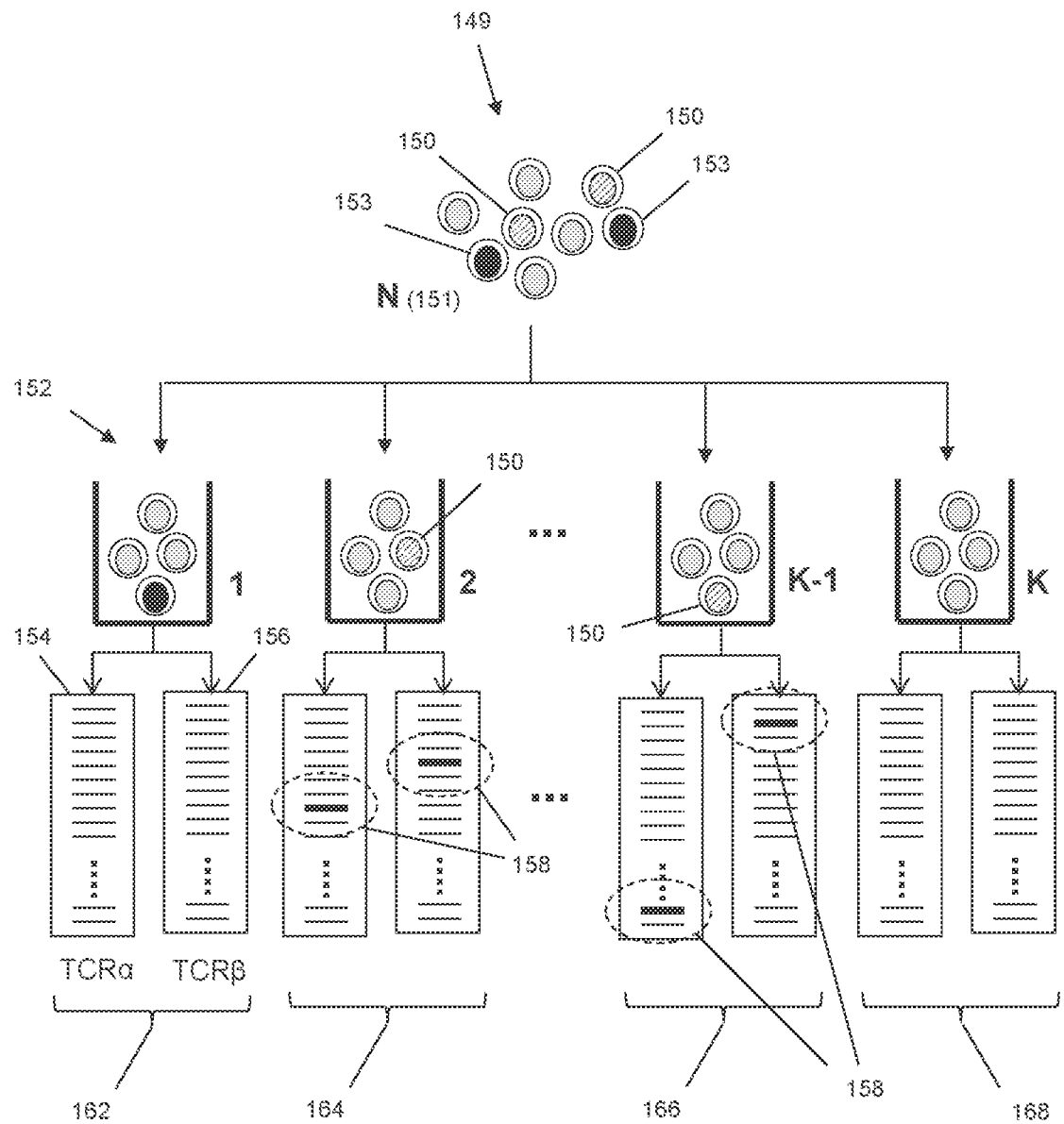
FIG. 1B illustrates diagrammatically steps of another embodiment of the invention for determining either TCRα or TCRβ chains that originate from the same T cell or heavy and light chain immunoglobulins that originate from the same B cell.

As illustrated in FIG. 1A, nucleic acid (which may be DNA or RNA) is extracted from a sample containing T cells (100), after which in separate reaction volumes, primers (102) specific for a nucleic acids encoding TCRα's (or a portion thereof) and primers (104) specific for nucleic acids encoding TCRβ's (or a portion thereof) are combined under conditions that allow the respective nucleic acid populations to be amplified, e.g. by a two-stage polymerase chain reaction (PCR), such as disclosed by Faham and Willis (cited above). Guidance and disclosures for selecting such primers and carrying out such reactions are described extensively in the molecular immunology literature and below (for TCRβ and IgH) and in references such as, Yao et al, Cellular and Molecular Immunology, 4: 215-220 (2007)(for TCRα), the latter reference being incorporated herein by reference. In one embodiment, amplicons (106) and (108) produced by a two-stage PCR are ready for sequence analysis using a commercially available next generation sequencer, such as MiSeq Personal Sequencer (Illumnina, San Diego, Calif.). After nucleotide sequences have been determined (107) and (109), databases or tables (110 and 112, respectively) are obtained. Like sequences may be counted and frequency versus sequence plots (114 and 116) are constructed. Reconstituted TCRs may be determined by matching (118) TCRα's and TCRβ's with identical frequencies or with frequencies having the same rank ordering. Clearly, this embodiment of the method works most efficiently when frequencies of different TCRα's and TCRβ's are not too close together, i.e. are distinct, even taking into account experimental error.

Once a pair of clonotype sequences having equal (or equally ranked) frequencies are identified full length sequences encoding each chain may be reconstructed from the known constant and variable regions using conventional techniques for genetic manipulation and expression, e.g. Walchli et al, PLosOne, 6(11): e27930 (2011); or the like.

Figure 2A:
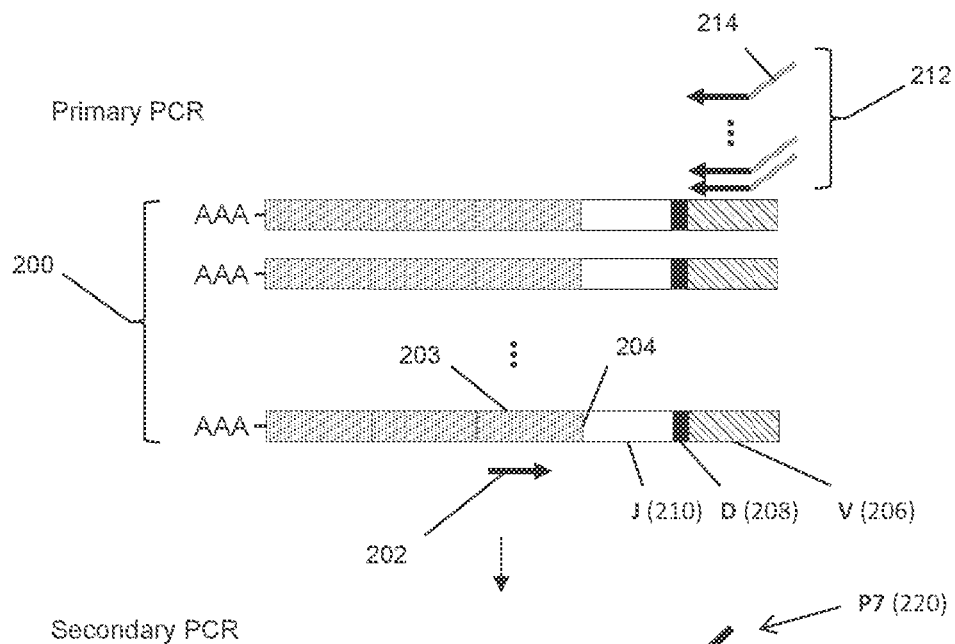
FIG. 2A-FIG. 2C show a two-staged PCR scheme for amplifying TCRβ genes.
Figure 2B:
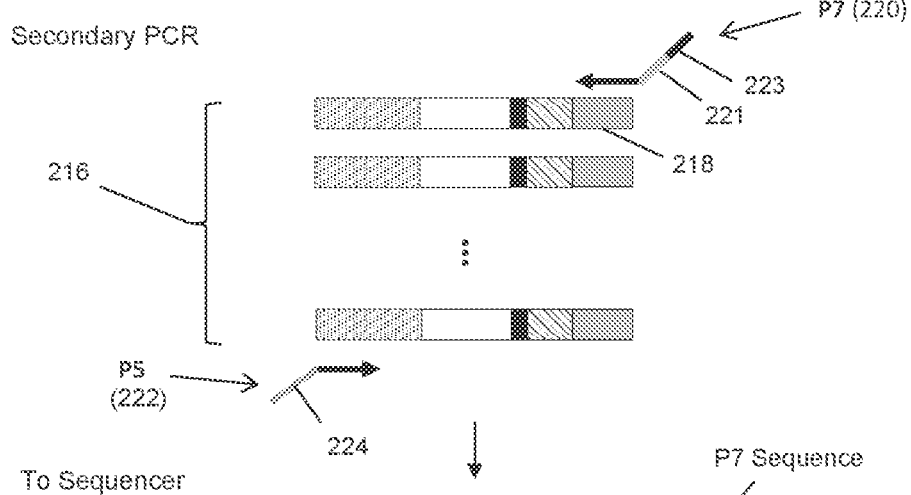

Greater accuracy in the determination of receptor chain frequencies may be obtained in a variation of the above embodiment, which may be seen in reference to FIGS. 2A and 2B where RNA encoding TCRβ is amplified in a two-staged PCR. As described more fully below, primer (202) and primer set (212) are used in a first stage amplification to attach common primer binding site (214) to all the nucleic acids encoding TCRβs. FIG. 2B illustrates the components of a second stage amplification for generating more material and for attaching primer binding sites P5 (222) and P7 (220) which are used in cluster formation (via bridge PCR) in the Solexa-based sequencing protocol. Primer P7 (220) may also include sample tag (221) for multiplexing up to 96 samples for concurrent sequencing in the same run, e.g. Illumina application note 770-2008-011 (2008). A different type of tag in the same primer may be used to increase the accuracy of the determination of receptor chain frequencies. In this embodiment, primer P7 is modified to include a highly diverse tag set, so that instead of 96 tags, primer P7 is engineered to have 10,000 distinct tags, or more. In other words, primer P7 is a mixture of 10,000 or more distinct oligonucleotides each having an identical template binding region, a distinct tag sequence, and an identical 5' tail portion (e.g., (223) in FIG. 2B). With this arrangement, any subset of nucleic acids encoding the same receptor chain (e.g. less than 100) will receive a different tag with high probability. Such a process of pairing members of a small set of nucleic acids with a much larger set of tags for counting, labeling, sorting purposes is well known and is disclosed in various forms in the following references that are incorporated by reference, Brenner, U.S. Pat. No. 6,172,214; Brenner et al, U.S. Pat. No. 7,537,897; and Macevicz, Internation patent publication WO US2005/111242; Brenner et al, Proc. Natl. Acad. Sci., 97: 1665-1670

(2000); Casbon et al, Nucleic Acids Research, 39(12): e81 (2011); Fu et al, Proc. Natl. Acad. Sci., 108: 9026-9031 (2011). Construction of sets of minimally cross-hybridizing oligonucleotide tag, or tags with other useful properties, is disclosed in the following exemplary references, which are incorporated by reference: Brenner, U.S. Pat. No. 6,172,214; Morris et al, U.S. patent publication 2004/0146901; Mao et al, U.S. patent publication 2005/0260570; and the like. Preferably, the tag set should be at least 100 times (or more) the size of the set of nucleic acids to be labeled if all nucleic acids are to receive a unique tag with high probability. For immune receptor chains, in one embodiment, the number of distinct tags is in the range of from 10,000 to 100,000; in another embodiment, the number of distinct tags is in the range of from 10,000 to 50,000; and in another embodiment, the number of distinct tags is in the range of from 10,000 to 20,000. As disclosed in Brenner, U.S. Pat. No. 6,172,214, such large mixtures of oligonucleotide tags may be synthesized by combinatorial methods; alternatively, primers containing unique tags may be synthesized individually by non-combinatorial methods, such as disclosed by Cleary et al, Nature Methods, 1: 241-248 (2004); York et al, Nucleic Acids Research, 40(1): e4 (2012); LeProust et al, Nucleic Acids Research, 38(8): 2522-2540 (2010); and the like.

In one aspect, the above embodiment may be carried out by the following steps: (a) obtaining a sample containing T cells; (b) determining nucleotide sequences of TCRα chains of T cells from the sample, each TCRα chain having a frequency of occurrence in the sample; (c) determining nucleotide sequences of TCRβ chains of T cells from the sample, each TCRβ chain having a frequency of occurrence in the sample; and (d) identifying paired TCRα chains and TCRβ chains as those having the same frequency within the sample. Frequencies of the respective TCRα chains and TCRβ chains may be determined from the tabulations of encoding nucleic acids, or clonotypes. Alternatively, frequencies of the respective TCRα chains and TCRO chains may be determined from the tabulations of polypeptides encoded by the clonotypes. As mentioned above, clonotype frequencies may be determined by counting clonotypes directly or indirectly by using a tagging scheme as described above.

FIG. 1B illustrates another embodiment for identifying matching receptor subunits which may be applied to either TCRs or BCRs and which may be used even when receptor frequencies among subunit chains are close or indistinguishable, whether because of experimental error or otherwise. Starting with a sample containing lymphocytes (149), which may be either T cells or B cells, subsets are formed by separating or partitioning the sample into a plurality of subsets (152), 1 through K (in the figure). In some embodiments, only a portion of the K subset are analyzed; thus, it is not necessary to actually form all K subsets. One may form subsets of only the portion that are actually analyzed. For example, if the sample has a volume of 100 μL and K=100, but only a portion consisting of 20 subset is to be analyzed, then only twenty 1 μL subsets need be formed. From each subset (152) nucleic acids encoding each different immune receptor chain (TCRα and TCRβ being shown under subset 1) are sequenced, thereby forming pairs of lists, for example, (162), (164), (166) and (168) for subsets 1, 2 . . . K-1, K, respectively. Each pair of such lists contains a first list of nucleotide sequences of a first immune receptor chain, e.g. list (154) for TCRα of subset 1, and a second list of nucleotide sequences of a second immune receptor chain, e.g. list (156) for TCRβ of subset 1. In one embodiment, the number of subsets, K, is a number in the range of from 5 to 500; in another embodiment, K is a number in the range of from 10 to 100; in another embodiment, K is a number in the range of from 20 to 50. In some embodiments, a portion of subsets analyzed is 10 or fewer subsets; in other embodiments, a portion of subsets analyzed is 20 or fewer subsets; in other embodiments, a portion of subsets analyzed is at least five percent of the subsets; in other embodiments, a portion of subsets analyzed is at least ten percent of the subsets; in other embodiments, a portion of subsets analyzed is at least twenty percent of the subsets.

Each kind of lymphocyte in sample, e.g. lymphocyte (150), is present in the sample at a particular frequency. The distribution of lymphocytes into the subsets is readily approximated by a bionomial model; thus, for an arbitrary lymphocyte (for example (150)) having a particular clonotype, (a) its frequency in the sample, (b) the total number of lymphocytes in the sample, and (c) the number of subsets may be related to the expectation of finding at least one of the particular lymphocyte in a predetermined fraction of subsets. This relationship may be expressed as follows: $r=(1-f)^{(N/K)}$, where r is the fraction of subsets containing at least one of the particular lymphocyte, f is the frequency of the particular lymphocyte in the sample, N is the total number of lymphocytes in the sample, and K is the number of subsets. Thus, if one sets r=½ and takes N as a constant, then one may select successive values of K so that lymphocytes of different frequencies are present in about half of the subsets. Other values of r could be selected, but r=½ provides results with the highest statistical power, thus the value r ½ is preferred. Once such lists are obtained they are examined to identify pairs of first and second nucleotide sequences that either occur in a subset together or are both absent from a subset. By way of example, the members of pair (158) appear in lists (164) of subset 2 and in lists (166) of subset K-1, but neither member of the pair appears in lists (162) or (168) of subsets 1 and K, either alone or together. This of course reflects the presence or absence of the particular lymphocyte that is in subsets 2 and K-1, but is absent from subsets 1 and K, such as lymphocyte (150). Such a pattern confirms that the members of pair (158) go together and correspond to the chains of a functional immune receptor. Other lymphocytes in sample (149) may be present in approximately the same frequency, such as lymphocyte (153). However, the probability that at least one of lymphocyte (153) will occur in exactly the same subsets as lymphocyte (150) is extremely low, especially if r is approximately one half and the portion of the K subsets analyzed is in the range of from 10 to 20, or more.

In one aspect of the invention, matched first and second chains of lymphocytes from a succession of frequency classes may be determined by carrying out the above process repeatedly for different values of K. For example, a 1 mL sample of peripheral blood of a normal individual contains about 1-4.8×10$^6$ lymphocytes of which about 10-15 percent are B cells, about 70-85 percent are T cells and about 10 percent are NK cells; thus, the 1 mL sample may contain from about 7×10$^5$ to about 4×10$^6$ T cells. If the number of T lymphocytes in a 1 mL sample is N=10$^6$, then matching TCR chains of T cells of the following frequencies are matched by identifying those that appear together in fifty percent of the subsets and not at all in the other fifty percent of subsets:

| Frequency | Number of Subsets | Volume (μL) |
| --- | --- | --- |
| .001 | 1443 | 0.7 |
| .0005 | 722 | 1.4 |

-continued

| Frequency | Number of Subsets | Volume (μL) |
|---|---|---|
| .0001 | 144 | 6.9 |
| .00005 | 72 | 13.9 |

As mentioned above, not all the subsets at a particular frequency need be analyzed. If there are a large number of lymphocytes that have frequencies at or close to a selected frequency, e.g. f=0.001, they may all be resolved by taking a larger and larger portion of the total number of subsets until every pair that appears together in fifty percent of the subsets can be distinguished from every other pair at the same frequency. This is because the probability of two different lymphocytes occurring in exactly the same subsets of the fifty percent becomes infinitesimal as the portion of subsets is increased.

Identifying Paired and Unpaired T-Cell Receptor Chains with Antigen-Specific Selection In some embodiments, the invention is directed to identifying antigen-specific T cells by one or a pair of immune receptor chains, such as TCRα, or TCRβ, or TCRα and TCRβ together; or TCRδ, or TCRγ, or TCRδ and TCRγ together. In some embodiments, the nucleotide sequence encoding a single immune receptor chain, such as TCRβ, is used to identify antigen-specific T cells. Sometimes such nucleotide sequences are referred to herein as a "clonotype," although clonotypes also may be ordered pairs of nucleotide sequences specific to a particular T cell, such as the nucleotide sequences encoding the T cell's TCRα and TCRβ chains, which may be represented (for example) as $(S_\alpha, S_\beta)$, or like notation, where Sa is a sequence of a segment of TCRα and $S_\beta$ is a sequence of a segment of TCRβ, and as a pair they are a clonotype of the cell they originate from.

Figure 1C:
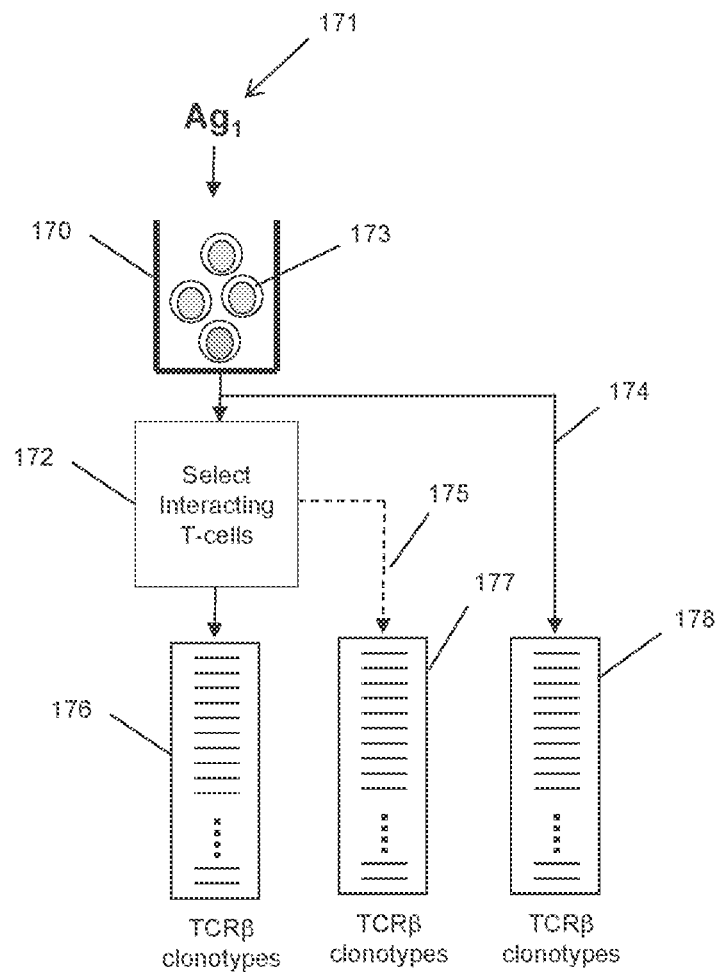
FIG. 1C illustrates diagrammatically an embodiment of the invention for identifying antigen-specific T cells that interact with a single antigen.

Features of some embodiments of the invention are illustrated in FIG. 1C. To a tissue sample (170) comprising T cells (173) is added antigen (171) under interaction conditions so that T cells specific for antigen (171) may interact with antigen (171). Such interaction may be direct or indirect. Direct interactions include binding of antigen (171) to antigen-specific T cells, binding of antigen peptide-multimer conjugates to antigen-specific T cells, and the like. Peptide-multimer conjugates, such as tetramers, are well-known reagents to those of ordinary skill, e.g. Bousso, Microbes Infect. 2(4): 425-429 (2000); Klenerman et al, Nature Reviews Immunol., 2(4): 263-272 (2002); and the like. Indirect interactions include presentation of antigen or antigen peptides to antigen-specific T cells by antigen presenting cells, such as, dendritic cells, artificial APCs, and the like. In some interactions, antigen-specific T cells may become activated T cells that may proliferate and/or develop or express activation markers both of which provide means for selecting and/or enriching antigen-specific T cells using conventional techniques. Antigen (171) may comprise a wide variety of compounds or compositions as discussed more fully below. Proteins and peptides derived from one or more proteins are of special interest, particularly when the proteins are associated with cancers or infectious diseases, such as bacterial or virus infections. Antigen (171) may be combined with, exposed to, or added to, tissue sample (170) in a variety of ways known in the art, e.g. Berzofsky et al, J. Clin. Investigation, 113: 1515-1525 (2004). After combining antigen (171) with tissue sample (170) in a reaction mixture, antigen-specific T cells (173) and non-antigen-specific T cells alike are exposed to antigen (171) with which they interact either directly or indirectly.

In some embodiments, antigen-specific T cells (173) are activated, possibly after a period of incubation with antigen (171). A period of incubation may vary widely. In some embodiments, incubation may be for an interval of from a few minutes (for example, 10 minutes) to an hour or more; in other embodiments, incubation may be for an interval of a few hours (for example, 2 hours) to 8 or more hours. In other embodiments, antigen-specific T cells (173) interact with antigen by binding to or forming complexes with antigen or antigen reagents, such as antigen peptide-multimer conjugates, such that activation may not take place. A step of exposing may include the step of incubating a tissue sample with an antigen. For example, in the case of a protein antigen and a tissue sample that comprises PBMCs, a step of exposing may include combining the tissue sample with peptides derived from the protein antigen such that dendritic cells in the tissue sample present the peptides to antigen-specific T cells in the tissue sample which, in turn, interact with the antigen-presenting dendritic cells and are activated. After exposing T cells (173) to antigen so that antigen-specific T cells interact with antigen, antigen-specific T cells may be selected (172) and/or enriched based on some feature resulting from the interaction, such as antigen peptide-multimer binding, activation markers induced, proliferation of the T cells, or the like. As mentioned above, the step of selecting (172) antigen-specific T cells may be alternatively a step of enriching antigen-specific T cells from the reaction mixture, and/or a step of separating antigen-specific T cells from the reaction mixture, and/or a step of isolating antigen-specific T cells from the reaction mixture. After antigen-specific T cells are enriched, separated, and/or isolated (172) their clonotypes are determined by sequencing a predetermined segment of a recombined nucleic acid that encodes a portion of an immune receptor, such as TCRβ and/or TCRα.

A predetermined segment chosen may vary widely; in some embodiments, it encompasses all or a portion of a V(D)J region, so that clonotypes based thereon have maximal diversity for unique identification oft cell clones. Determination of clonotypes is described more fully below, but briefly, recombined nucleic acids encoding one or more selected immune receptors (such as TCRβ as shown in FIG. 1C) are sequenced (for example, by spatially isolating molecules thereof, amplifying such molecules, and carrying out sequencing steps by a high-throughput sequencing chemistry, such as available with commercial next-generation DNA sequencers). As a result of these sequencing steps, sequence reads (176) are produced which are used to determine clonotypes and clonotype frequencies of antigen-specific T cells. Clonotypes and clonotype frequencies are also determined either for T cells of the tissue sample (174) from sequence reads (178) or for non-antigen-specific T cells (175) from sequence reads (177). Non-antigen-specific T cells may be obtained from a two-way sorting procedure (for example, using FACS or MACS) based on T cells labeled according to an interaction, such as, an interaction of antigen-specific T cells with fluorescently labeled antigen peptide multimers. These data may then be analyzed to identify clonotypes associated with antigen-specific T cells, for example, as described in the Example below and FIGS. 6-9. Briefly, in some embodiments, antigen-specific T cells may be associated with clonotype frequencies that increase in the selected population of T cells relative to frequencies of the same clonotype in populations of non-antigen specific T cells or in the population of T cells in tissue sample (170).

Exemplary steps for implementing this embodiment of the invention (i.e., for determining clonotypes associated with antigen-specific T cells in a tissue sample) may include the following: (a) exposing the T cells of the sample to an antigen so that T cells specific for the antigen interact with the antigen; (b) sequencing recombed nucleic acids encoding a T-cell receptor chain or a portion thereof from a sample of T cells from the tissue sample to provide sequence reads from which clonotypes are determined; (c) isolating anigen-specific T cells from the tissue sample based on their interaction with the antigen; (d) sequencing recombined nucleic acids encoding a T-cell receptor chain or a portion thereof from a sample of the isolated antigen-specific T cells to provide sequence reads from which clonotypes are determined; and (e) determining antigen-specific T cells in the tissue sample as T cells whose clonotype frequencies increase in the sample of isolated T cells relative to the frequencies of the same clonotypes in a sample of T cells in the tissue sample. In some embodiments, a step of exposing may be carried out by reacting under interaction conditions an antigen with a tissue sample; in still other embodiments, a step of exposing may be carried out by reaction under activation conditions an antigen with a tissue sample. As mentioned above the step of exposing for this and other embodiments may vary widely, and its implementation may depend on the nature of the tissue sample and the nature of the antigen, as well as other factors. For example, if a tissue sample includes antigen-presenting cells, such as dendritic cells, then exposing may include either addition of an antigen, such as a protein, directly to the tissue sample, or it may include producing antigenic material from an antigen of interest followed by addition of the antigenic material. More efficient T cell activation to a protein antigen, for example, may be accomplished by exposing a tissue sample to a set of overlapping peptides derived from the protein antigen of interest, using conventional techniques. Alternatively, artificial antigen-presenting compositions may be used in the exposing step or its equivalent, e.g. Oelke et al, Nature Medicine, 9(5): 619-624 (2003). The step of exposing T cells in a tissue sample may include exposing such T cells to whole cells containing antigen, to gene-modified cells expressing antigen, to whole protein, to peptides derived from a protein antigen, to viral vectors expressing an antigen, to antigen-modified, or loaded, dendritic cells. In some embodiments, a tissue sample is a blood sample; in other embodiments, a tissue sample is a sample of peripheral blood mononuclear cells (PBMCs) derived from peripheral blood using conventional techniques. In some embodiments the step of exposing may be carried out by reacting under activation conditions a tissue sample comprising T cells with an antigen, where various activation conditions are described above. In view of the wide variety of tissue samples and antigens, the step of exposing may be alternatively carried out by a step of reacting under activation conditions a tissue sample comprising T cells with an antigen.

Further exemplary steps for implementing the above method may comprise: (a) reacting under activation conditions a tissue sample comprising T cells to an antigen; (b) sorting from the tissue sample activated T cells and unactivated T cells; (b) sequencing recombined nucleic acids encoding a T-cell receptor chain or a portion thereof from a sample of T cells from the activated T cells to provide sequence reads from which clonotypes are determined; (c) sequencing recombined nucleic acids encoding a T-cell receptor chain or a portion thereof from a sample of T cells from the unactivated T cells to provide sequence reads from which clonotypes are determined; and (d) determining antigen-specific T cells in the tissue sample as T cells whose clonotype frequencies increase in the sample of activated T cells relative to the frequencies of the same clonotypes in the tissue sample or in a sample of unactivated T cells. Likewise, exemplary steps for implementing the above method may comprise: (a) reacting under interaction conditions a tissue sample comprising T cells with an antigen; (b) sorting T cells of the tissue sample into a first subset of T cells that form complexes with the antigen or antigen reagents thereof and into a second subset of T cells that do not form complexes with the antigen or antigen reagents thereof; (b) sequencing recombined nucleic acids encoding a T-cell receptor chain or a portion thereof from a sample of the first subset to provide sequence reads from which clonotypes are determined; (c) sequencing recombined nucleic acids encoding a T-cell receptor chain or a portion thereof from a sample of T cells from the tissue sample or the second subset to provide sequence reads from which clonotypes are determined; and (d) determining antigen-specific T cells in the tissue sample as T cells whose clonotype frequencies increase in the sample of T cells of the first subset relative to the frequencies of the same clonotypes in the tissue sample or in a sample of T cells from the second subset. As used herein, the term "antigen reagents" means reagents derived from an antigen designed to bind to, or form complexes with, T cells whose TCRs are specific for the antigen. Exemplary antigen reagents include, but are not limited to, multimers conjugated with peptides derived from an antigen.

In some embodiments, the above method of determining antigen-specific T cells in a tissue sample may be carried out by steps comprising: (a) reacting under activation conditions in a reaction mixture a tissue sample comprising T cells to an antigen or antigen reagents thereof; (b) sequencing recombined nucleic acids encoding a T-cell receptor chain or a portion thereof from a sample of T cells from the reaction mixture prior to addition of the antigen to the reaction mixture to provide sequence reads from which clonotypes are determined; (c) incubating the reaction mixture after addition of the antigen or antigen reagent thereof for a predetermined interval; (d) sequencing recombined nucleic acids encoding a T-cell receptor chain or a portion thereof from a sample of T cells from the incubated reaction mixture to provide sequence reads from which clonotypes are determined; (d) determining antigen-specific T cells in the tissue sample as T cells whose clonotype frequencies increase in the incubated reaction mixture relative to the frequencies of the same clonotypes in the reaction mixture prior to the addition of antigen. In some embodiments, a predetermined interval for incubation is usually greater than eight hours; in other embodiments, a predetermined interval may be greater than 24 hours; in further embodiments, a predetermined interval may be within a range of from 8 hours to 72 hours.

In some embodiments, step of isolating antigen-specific T cells may be substituted with either a step of separating a sample of antigen-specific T cells from the tissue sample after exposure to an antigen of interest or a step of recovering antigen-specific T cells from the tissue sample after exposure to an antigen of interest. In some embodiments, such step of isolating may be carried out by sorting antigen-interacting and/or activated T cells from a tissue sample; likewise, in some embodiments, non-antigen-specific T cells and/or unactivated T cells may be sorted from a tissue sample. Such steps of the various embodiments may be carried out by a variety of methods including, but not limited to, (i) peptide-MHC multimer staining reagents (such as, tetramers, pentamers, or the like), followed by sorting, panning, or otherwise capturing complexes between such reagents and antigen-specific T cells, (ii) sorting or panning or capturing based on activation markers, such as CD137, CD154, or others (described more fully below), or (iii) proliferation (and therefore, for example, an increase in frequency) of antigen-specific T cells over antigen-non-specific T cells. Thus, in some embodiments, said step of isolating may comprise a step isolating activated T cells; or a step of separating activated T cells from the tissue sample. In some of such embodiments, T cell activation markers, as noted above, may be used to sort, pan or otherwise capture activated T cells, using conventional techniques. Generally, a step is taken for obtaining a sample of T cells from a pool of T cells derived from the tissue sample, which pool is enriched in antigen-specific T cells and/or activated T cells. In some embodiments, T cells with an activation marker may be sorted or isolated using a binding compound, such as an antibody, which specifically binds to the activation marker and which can be directly or indirectly labeled in accordance with conventional methods, e.g. FACS, magnetic bead-based separation, or like techniques.

In another application of the above embodiment, T cell immunogenicity may be measured in the following steps: (a) reacting under activation conditions a tissue sample comprising T cells with an antigen or an antigen reagent thereof; (b) sequencing recombined nucleic acids encoding a T-cell receptor chain or a portion thereof from a sample of T cells from the tissue sample exposed to antigen or antigen reagents thereof to provide sequence reads from which clonotypes are determined; (c) isolating activated T cells from the tissue sample; (d) sequencing recombined nucleic acids encoding a T-cell receptor chain or a portion thereof from a sample of the activated T cells isolated from the tissue sample to provide sequence reads from which clonotypes are determined; and (e) quantifying immunogenicity of the antigen as a function of increases in frequencies of clonotypes in the sample of isolated T cells exposed to antigen with respect to frequencies of the same clonotypes in the tissue sample prior to said step of isolating. Exemplary functions of increases in frequencies of clonotypes include an average of increases among the isolated antigen-specific T cells; another exemplary function of increases includes an average distance of data points of clonotypes registering increases in frequency from the diagonal in plots such as those of FIG. 6, 7 or 8. Still another measure of T cell immunogenicity includes any of several similarity measures of a clonotype profile of T cells of the exposed tissue sample prior to isolating and a clonotype profile of T cells of a sample of T cells isolated (or separated) from the tissue sample, such as described in Faham et al, International Patent Publication No. WO 2013/036459, which is incorporated herein by reference. In this embodiment, antigens of particular interest are therapeutic proteins, such as therapeutic antibodies.

In one aspect, a similarity measure for use with these embodiments of the invention is a monotonically varying function that maps (or is capable of mapping by a simple transformation) at least two sets of clonotype frequency measurements (e.g. two sequence-based clonotype profiles) to the unit interval [0,1]. Simple transformations include, but are not limited to, any linear transformation of dependent variables, logarithmic transformations, such as $y_{ij}=\ln(n_{ij}+1)$ (where $n_{ij}$ is the number of clonotype i in sample j), or the like. A value of zero means no similarity between clonotype profiles and a value of one means two clonotype profiles are statistically identical. Exemplary similarity measures that may be implemented in these embodiments are described in Legendre and Legendre, Numerical Ecology (Elsevier, 1998); Magurran, Measurement of Biological Diversity (Wiley-Blackwell, 2003); Wolda, Occologia (Berl), 50: 296-302 (1981); and like references, which are incorporated by reference. Such similarity measures include, but are not limited to, Czekanowski's index, Dice's coefficient, Horn's information theory index, Canberra metric, Morisita's index, Kaczynski's similarity index, Sorensen's index, Jacquard's index, Bray-Curtis index, and the like. In one aspect, similarity measures are similarity metrics; or in other words, the similarity measures employed have properties of a distance measure, such as, (i) the value of the measure is always non-negative, (ii) the measure is zero if and only if the clonotype profile measurements are identical, (iii) the value of the measure is invariant with respect to the ordering of the clonotype profile measurements (sometimes expressed as $d(x,y)=d(y,x)$), (iv) the triangle inequality holds with respect to three different clonotype profile measurements. In another aspect, similarity measures may be correlation coefficients (subject to a simple transformation, e.g. taking its absolute value, squaring its value, or the like, so that its value is restricted to the unit interval). Exemplary correlation coefficients include, but are not limited to, Pearson product-moment correlation coefficient and rank correlations, such as Spearman's rank correlation coefficient, Kendall's tau rank correlation coefficient, and the like. In one embodiment a Morisita-Horn index ($C_{13}$) (including Morisita-Horn index with a logarithmic transformation), as disclosed in Wolda (cited above), is employed with the embodiments.

Figure 1D:
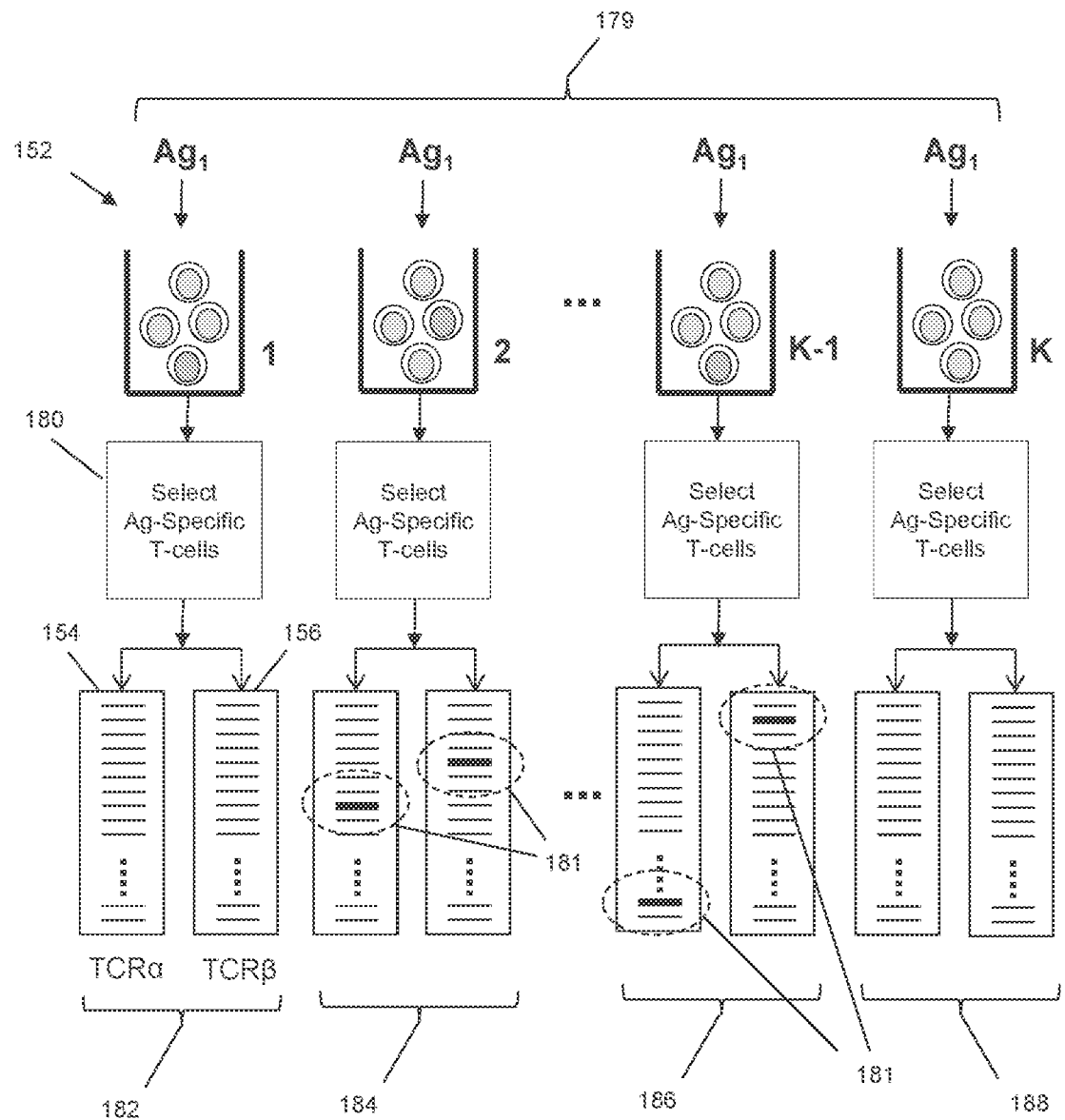
FIG. 1D illustrates diagrammatically an embodiment of the invention for identifying antigen-specific T cells that interact with a plurality of antigens.

Another embodiment for identifying pairs of immune receptor chains of antigen-specific T cells is illustrated in FIG. 1D, where T cell containing reaction mixtures are exposed to a single antigen. Similarly to the embodiment of FIG. 1B, a tissue sample is partitioned into subsets (152) from 1 to K and a portion of the subsets may be selected for analysis. Ranges in the values of K and the portion selected may be the same as for the embodiment of FIG. 1B. In one embodiment, as above, the partitions may be aliquots of the tissue sample, in which approximately equal amounts of tissue sample are provided to each subset, for example, by distributing equal amounts of tissue sample to each of K reaction mixtures, which may be contained by vessels or reactors, such as wells in a multi-well plate. Tissue samples may also be distributed to a plurality of K separate chambers of a microfluidics device in connection with this and/or the embodiments described above. T cells of each subset are exposed to antigen (179) after which reaction mixtures in the K vessels are incubated for a time (for example, a predetermined interval) sufficient for T cells to respond to, or interact with, the antigen, either directly or in a processed form (for example, as an antigen reagent). Such response may include forming a stable complex with antigen or a processed form thereof, or may include the development and/or expression of activation markers by T cells, or may include proliferation by T cells specific for the antigen. Antigen-interacting or antigen-responding T cells are then selected (180) and isolated (for example, sorted) from each of the K chambers, after which recombined nucleic acids encoding predetermined portions of one or both TCR chains are sequenced to provide sequence reads from which clonotypes and clonotype profiles (for example, 154 and 156) are formed. As above with the embodiment of FIG. 1B, once such profiles are obtained they are examined to identify pairs of first and second nucleotide sequences that either occur in a subset together or are both absent from a subset. By way of example, the members of pair (181) appear in lists (184)

of subset 2 and in lists (186) of subset K−1, but neither member of the pair appears in lists (182) or (188) of subsets 1 and K, either alone or together. As above, this reflects the presence or absence of a particular lymphocyte, which in this illustration is in subsets 2 and K−1, but is absent from subsets 1 and K. Such a pattern confirms that the members of pair (181) go together and correspond to the chains of a functional immune receptor that is specific for antigen, $Ag_1$ (179).

In some embodiments, the above method of determining receptors of antigen-specific T cells in a tissue sample may comprise the following steps: (a) partitioning a tissue sample containing T cells into a plurality of subsets; (b) exposing the T cells of each of a portion of subsets to an antigen so that T cells specific for the antigen are activated; (c) isolating the activated T cells of each subset of the portion; (d) sequencing recombined nucleic acids encoding T-cell receptor α chains in each subset of the portion to provide sequence reads from which α chain clonotypes are determined; (e) sequencing recombined nucleic acids encoding T-cell receptor β chains in each subset of the portion to provide sequence reads from which β chain clonotypes are determined; and (f) identifying as antigen-specific T cell receptors with those pairs of α chain clonotypes and β chain clonotypes that for every subset of the portion (i) either both the α chain clonotype and β chain clonotype are present in a subset or neither are present in a subset, and (ii) both the α chain clonotype and β chain clonotype are present in at least one subset of the portion and the α chain clonotype and β chain clonotype are not present in at least one subset of the portion.

Alternatively, in some embodiments, the above method of determining receptors of antigen-specific T cells in a tissue sample may comprise the following steps: (a) forming a plurality of subsets from a tissue sample containing T cells; (b) reacting under activation conditions the T cells of each subset to an antigen; (c) isolating the antigen-specific T cells of each subset; (d) sequencing recombined nucleic acids encoding T-cell receptor α chains in each subset to provide sequence reads from which α chain clonotypes are determined; (e) sequencing recombined nucleic acids encoding T-cell receptor β chains in each subset to provide sequence reads from which β chain clonotypes are determined; (d) identifying as antigen-specific T cell receptors with those pairs of α chain clonotypes and β chain clonotypes that for every subset (i) either both the α chain clonotype and β chain clonotype are present in a subset or neither are present in a subset, and (ii) both the α chain clonotype and β chain clonotype are present in at least one subset and the α chain clonotype and β chain clonotype are not present in at least one subset. In some of these latter embodiments, the plurality of subsets formed may correspond to a portion of the plurality into which a tissue sample is partitioned in the former embodiments. In some embodiments, the step of forming a plurality of subsets may comprise aliquoting portions of a tissue sample into separate reaction vessels. In some embodiments, such portions are equal portions.

Figure 5A:
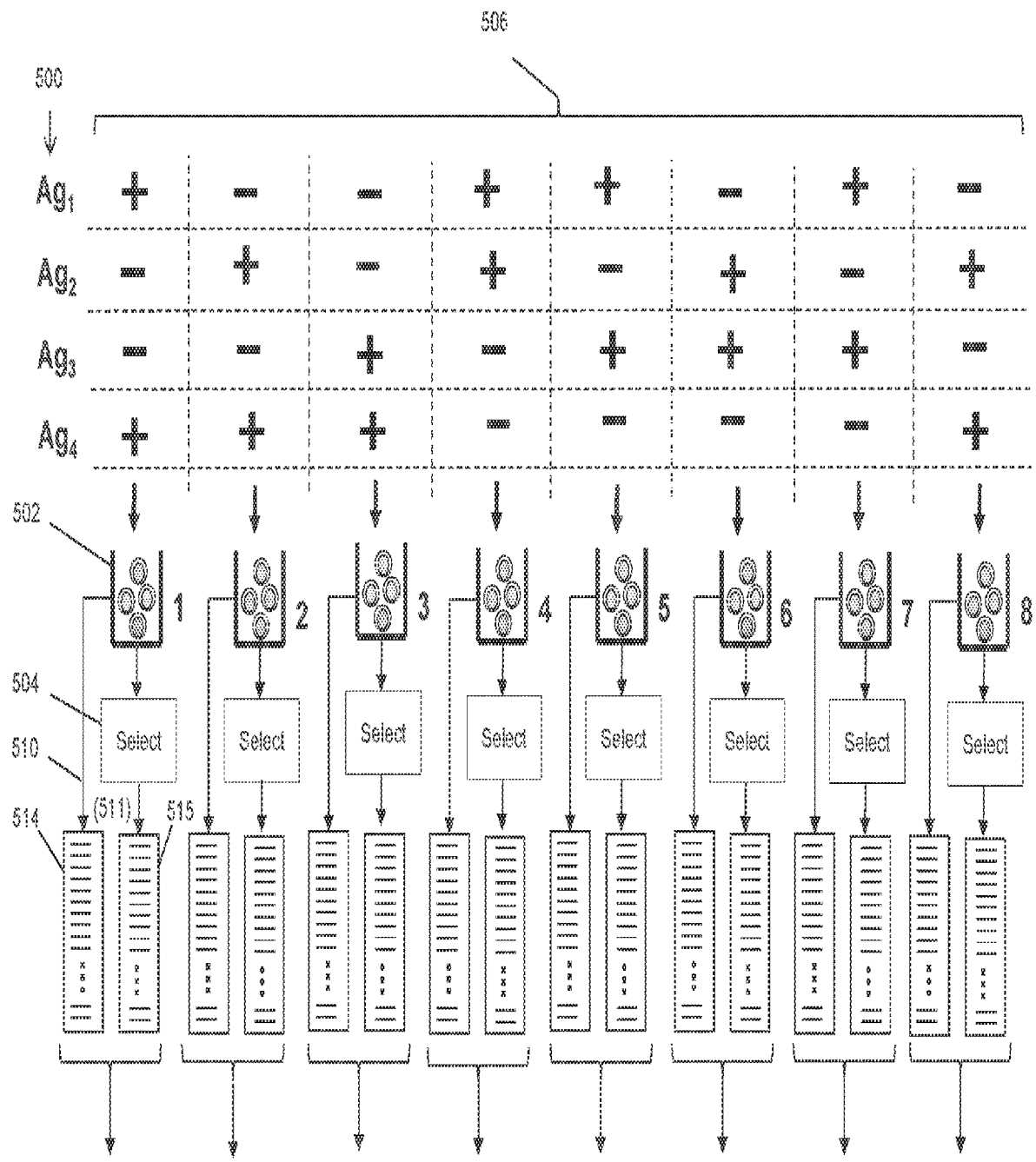
FIG. 5A-FIG. 5B illustrate an embodiment of the invention for determining T-cells and TCRs specific for a plurality of antigens.
Figure 5B:
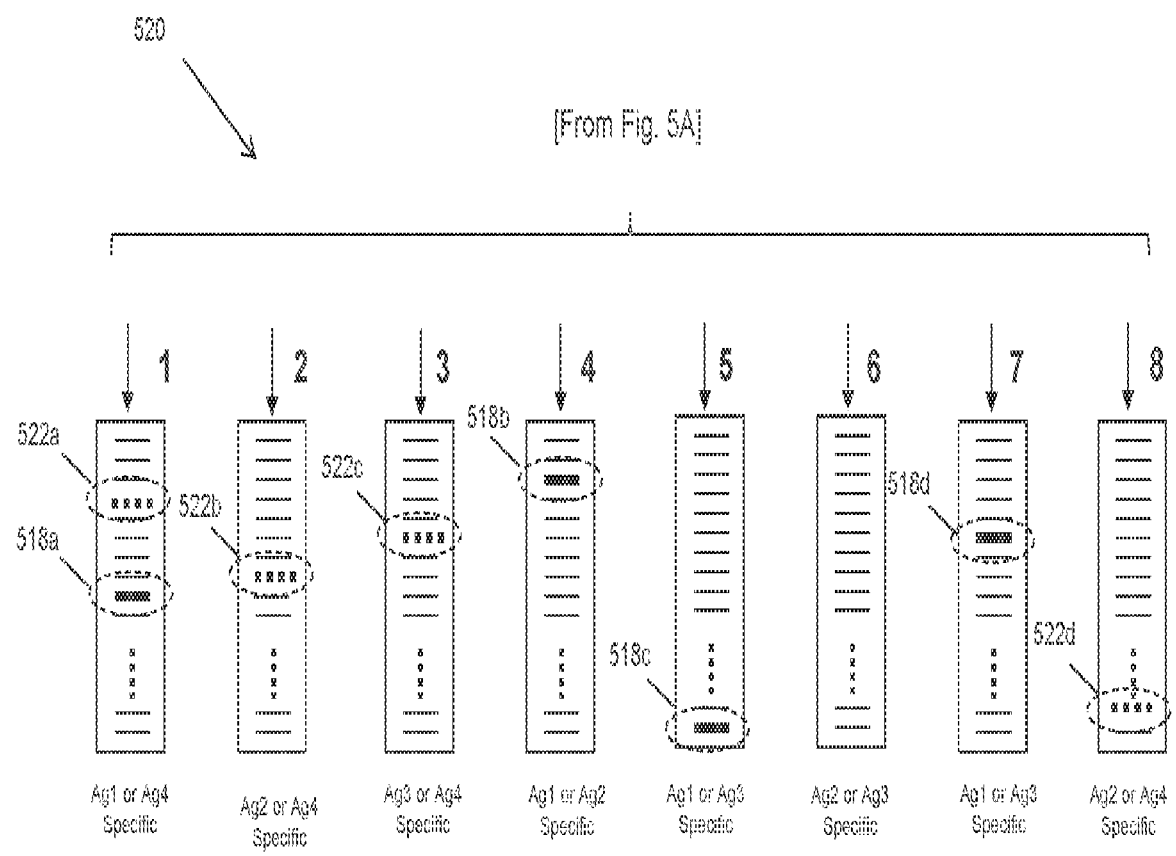

Another embodiment for identifying clonotypes of antigen-specific T cells is illustrated in FIGS. 5A-5B, where a plurality of antigens (500) is exposed to T cells in a plurality of different reaction mixtures. In one aspect, this embodiment permits the identification of antigen-specific T cells from scarce tissue samples, such as from a cancer patient whose tissue sample will be used to identify clonotypes for immune monitoring (e.g. minimal residual disease (MRD) analysis), to produce a patient-specific immunotherapeutic reagent using cancer antigen-specific T cells, or the like. Subsets (or reaction mixtures) (502) from 1 to K (shown in FIGS. 5A-5B as 1-8) are formed from a tissue sample. The number of different antigens employed may vary widely and in some embodiments the number depends on the nature of the antigens. For protein antigens, in some embodiments, a plurality of protein antigens may be employed; in further embodiments, a plurality of protein antigens may be in the range of from 2 to 100 protein antigens; in other embodiments, a plurality may be in the range of from 2 to 50 protein antigens; in other embodiments, a plurality may be in the range of from 2 to 10 protein antigens; in still other embodiments, a plurality may be in the range of from 2 to 1000 protein antigens. Each antigen of plurality (500) is exposed to (or presented to) T cells of a subplurality of reaction mixtures (502) less than the total plurality of K reaction mixtures (in this illustration, subpluralities are each 4). Selections of the subsets of reaction mixtures into which antigens are placed are predetermined for each antigen. In some embodiments, each antigen is applied or exposed to a unique subplurality of subsets. That is, the selection of subsets making up a subplurality corresponding to a particular antigen is unique to that antigen. The size of the subpluralites may be the same or different for each antigen; but in some embodiments, the size of the subpluralities (i.e. the number of subsets in each) are the same for each antigen (which is equal to 4 in FIGS. 5A-5B). In some embodiments, subpluralities of subsets correspond to a different combination of subsets out of the plurality (in this case 8), as mentioned above. Thus, for some embodiments, the number of possible subsets is the same as the number of different combinations of R subsets selected from the total number of subsets, K. (For example, for R=4 and K=8, the number of different combinations is K!/(R!(K−R)!).

A selection of different combinations (or subpluralities) for antigens (500) is indicated by matrix (506) of +'s and −'s which indicate which antigen is exposed to T cells of which subsets. As mentioned above, the selection of subsets into which an antigen is applied (or exposed) is predetermined; thus, for example, antigen $Ag_1$ is applied to subplurality of subsets 1, 4, 5 and 7. A subplurality of subsets which are exposed to antigen may vary between 2 and K−1; however, in some embodiments, the size of the subplurality is an integer equal to or closest to K/2. As above, after exposure to antigen and optional incubation, antigen-specific T cells are selected (504) (e.g. based on interaction with with an antigen in the reaction mixture) and clonotype profiles are generated for recombined nucleic acids encoding a selected TCR chain or a portion thereof (as illustrated for subset 1), which permits its corresponding T cell to be identified and/or isolated. Prior to exposure, a sample of T cells may be taken from the tissue sample subsets (for example, 510). Recombined nucleic acids encoding clonotypes of the same TCR segment are sequenced both in sample (510) and in sample (511) to produce sequence reads (514) and (515) from which clonotypes and clonotype frequencies are determined. Frequencies of clonotypes that increase in the selected pools of T cells (illustrated as lists (520) in FIG. 5B) correspond to T cells specific for antigens (for example, Ag1 or Ag4 in reaction mixture 1) An antigen-specific clonotype may be identified by observing a clonotype that increases in frequency in every reaction mixture of a given antigen. For example, in FIGS. 5A-5B, the same clonotype (518a, 518b, 518c and 518d) is observed to have increased in frequency within reaction mixtures 1, 4, 5 and 7 which corresponds to the unique subplurality of subsets into which antigen 1 was added, but not to have increased in the other reaction mixtures where antigen 1 was absent; therefore, clonotype (518) identifies a T cell with a TCR specific for antigen 1. Likewise, the same clonotype (522a, 522b, 522c and 522d) is observed to have increased in frequency within reaction mixtures 1, 2, 3 and 8, which corresponds to the unique subplurality of subsets into which antigen 4 was added, but not to have increased in frequency in the other reaction mixtures where antigen 4 was absent; therefore, clonotype (522) identifies a T cell with a TCR specific for antigen 4. Since each antigen is exposed to T cells in a unique subplurality of reaction mixtures (or subsets), whenever the same clonotype is observed in each reaction mixture of the unique subplurality, then the clonotype corresponds to a TCR specific for the antigen corresponding to the subplurality.

In one aspect, the above embodiments of the invention for determining clonotypes of antigen-specific T cells in a tissue sample may be carried out with the following steps: (a) forming a plurality of subsets from a tissue sample containing T cells; (b) exposing under interaction conditions T cells in a subplurality of subsets to one or more antigens so that T cells specific for any of the one or more antigens are capable of interacting therewith, and wherein each different antigen is exposed to T cells in a different subplurality; (c) enriching the antigen-interacting T cells of each subset of a subplurality; (d) sequencing recombined nucleic acids encoding a T-cell receptor chain or a portion thereof from said enriched T cells in each subset of the subplurality to provide sequence reads from which clonotypes are determined; (e) sequencing recombined nucleic acids encoding T-cell receptor chain or a portion thereof from said T cells in each subset of the subplurality prior to said step of enriching or from non-enriched T cells in each subset of the subplurality to provide sequence reads from which clonotypes are determined; and (f) identifying a clonotype of a T cell specific for an antigen of the one or more antigens as a clonotype whose frequency increases in each subset of a subplurality corresponding to the antigen and does not increase in subsets outside of such subplurality. That is, in some embodiments, such clonotypes are identified by observing the clonotypes in all reaction mixtures that increase in frequency (520 in FIG. 5B) and identifying clonotypes that appear in each of the subsets of the subplurality corresponding to a given antigen and that is absent in all of the other subsets. In other words, a clonotype of a T cell specific for an antigen increases in frequency only in the subsets or reaction mixtures to which the antigen was added and not in the others. In some embodiments, a clonotype of an antigen-specific T cell may be identified whenever the frequency such clonotype increases in substantially every subset of a subplurality corresponding to the antigen and does not increase in substantially every other subset (every subset not part of the subplurality).

Figure 4:
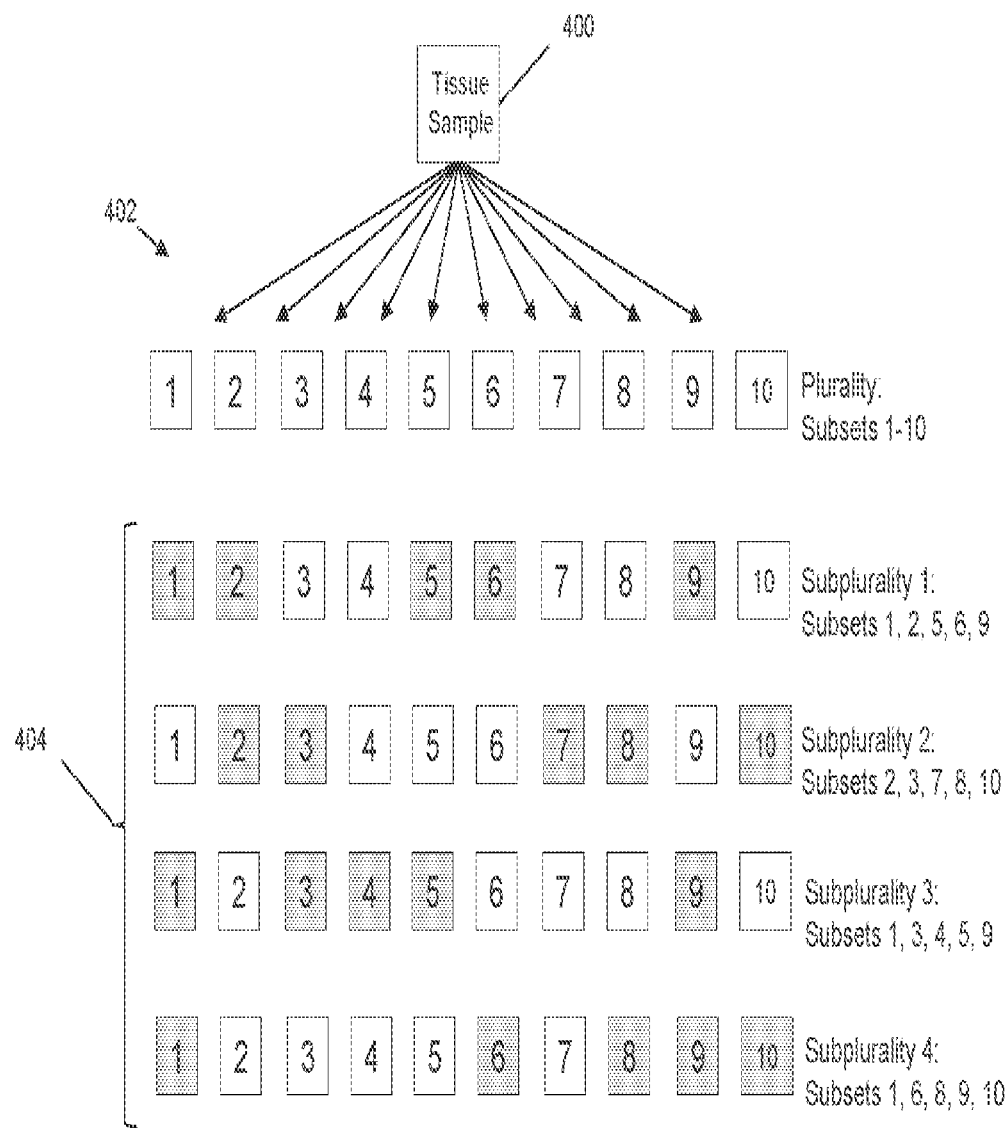
FIG. 4 illustrates an example of a tissue sample divided or aliquoted into a plurality of subsets 1 through 10 and examples of different subpluralities of subsets of the plurality.

For clarity, FIG. 4 illustrates the process of selecting subpluralities of a plurality of subset in accordance with some embodiments of the invention. Tissue sample (400) is separated into a plurality of subsets (402), for example, 10 as shown in FIG. 4. Tissue sample (400) may also be aliquoted into a plurality of subsets, or a plurality of subsets may be formed from it, which may or may not use the entire amount of tissue sample (400). A subplurality of plurality (402) is a selection of from two to nine subsets of plurality (402). In some embodiments, several subpluralities are selected that each have the same number of subsets, such as illustrated in FIG. 4, where each subplurality consists of five subsets. In some embodiments of the invention, a different antigen is exposed to T cells in subsets of a different subplurality. Thus, for example, subplurality 1 may be exposed to antigen 1, subplurality 2 exposed to antigen 2, and so forth. Consequently, in FIG. 4, subset 1 is exposed to antigen 1, antigen 3 and antigen 4; likewise, subset 2 is exposed to antigen 1 and antigen 2; and so forth.

Figure 1E:
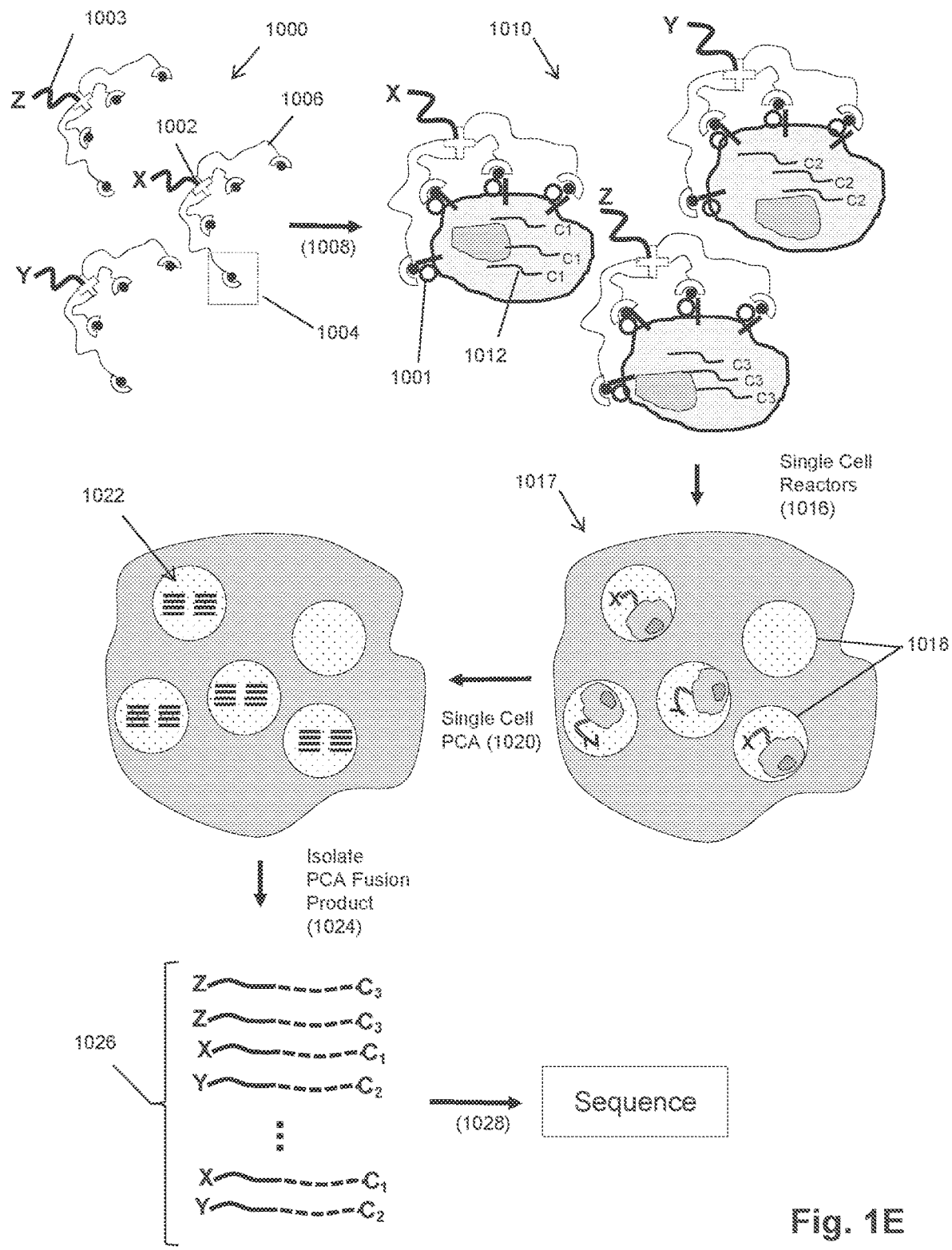
FIG. 1E illustrates steps of an embodiment of the invention for physical identification of antigen-specific T cells using single cell methodology.

Identification of Antigen-Specific T Cell Clonotypes Using Single Cell Techniques In some embodiments, antigen-specific T cell clonotypes may be identified using single cell techniques, such as disclosed in Faham and Willis, U.S. Pat. Nos. 8,236,503 and 8,507,205, which are incorporated herein by reference. In one aspect, the step of selecting T cells that interact with antigen is carried out by disposing T cells exposed to antigen(s) into reactors so that a substantial fraction of reactors contain a single T cell and a single labeled antigen reagent, usually bound to a TCR of the T cell. An objective of these embodiments of the invention is to carry out a polymerase cycling assembly (PCA) reaction (also sometimes referred to as a "linking PCR") on individual cells in the reactors to link their recombined nucleic acid sequences (e.g., encoding a portion of a TCR) to a sequence tag that is associated with, or labels, an antigen reagent present in the reactor with the single T cell. The products of such linking are referred to herein as "fusion products." After their generation, fusion products can be sequenced to identify both the clonotype of the TCR and the sequence tag which, in turn, identifies the antigen reagent. FIG. 1E gives an overview on one embodiment of the invention. Lymphoid cells (1010) (shown combined with antigen reagents (1000)) each have a distinct identifying nucleic acid (1012), which in the figure are exemplified (without any intention of being limiting) as messenger RNAs (mRNAs)(1012), which in the three cells illustrated in the figure are labeled "$C_1$", "$C_2$", and "$C_3$", to indicate that they are three different recombined nucleic acids unique to each cell, respectively. These recombined nucleic acids encode TCRs (for example, 1001) expressed on the surface of the respective T cells. As mentioned above, T cells (1010) are shown combined with antigen reagents (1000), which may be conventional multimers, such as tetramers, which are labeled with sequence tags (for example, 1003) that identify the MHC and peptide portions of the antigen reagent (for example, as shown enclosed in dashed box 1004). Antigen reagent (1000) is exemplified with a conventional structure comprising a framework component (1002), such as a streptavidin molecule; MHC linking moieties (such as, biotinylated peptides (for example, 1006)); and MHC-peptide complexes (1004).

Antigen reagent (1000) may also include sequence tag labels (such as, 1003), which may be produced as taught by Kwong et al, U.S. Pat. No. 8,394,590, which is incorporated herein by reference. The MHC and peptide portion determines the specificity of the reagent for a TCR and vice versa. Antigen reagents (1000) are produced so that substantially every different antigen reagent (e.g. every different multimer) has a different sequence tag. In some embodiments, sequence tags and MHC-peptide portions are selected so that with the knowledge of a tag's sequence, the identity of the MHC-peptide portion can be uniquely determined. That is, for example, there is a one-to-one correspondence between a sequence tag and an MHC-peptide complex, so that (for example), a sequence tag "X" indicates the presence of recombined nucleic acid "$C_1$", a sequence tag "Y" indicates the presence of recombined nucleic acid "$C_2$", and a sequence tag "Z" indicates the presence of recombined nucleic acid "$C_3$". Antigen reagents (1000) are combined (1008) with T cells (1010) in a reaction mixture and are incubated under antigen-interaction conditions which permit the formation of T cell-reagent complexes whenever a TCR is specific for an antigen reagent. After such incubation, cells are disposed (1016) in single cell reactors, which may vary widely and may include, but not be limited to, plates with arrays of nanoliter-volume wells, microfluidic devices, and the like, as described more fully below. In some embodiments, single cell reactors are aqueous micelles in an emulsion, such as illustrated (1017) in FIG. 1E, where a substantial fraction of micelles in the emulsion contain a single T cell together with a single antigen reagent. In one aspect, single-cell emulsion (126) is generated using a microfluidic emulsion generator, such as disclosed by Zeng et al, Anal. Chem., 82: 3183-3190 (2010), or the like.

Reactors (1018) contain a PCA reaction mixture that, for example, may comprise a nucleic acid polymerase, outer primers and linking primers (described more fully below), nucleoside triphosphates, a buffer solution, and the like. In some embodiments, a PCA reaction mixture may also include one or more cell lysing reagents, to give the foregoing reagents access to intracellular recombined nucleic acids, such as mRNAs. For each reactor (1018) containing a cell, PCA reaction (1020) generates fusion products (1022) that may comprise one or more pairs of sequences, such that one member of the pair is a sequence tag and the other member is a predetermined recombined nucleic acid. In other embodiments, fusion products may comprise triplets of sequences, or higher order concatenations, for example, as taught by Faham and Willis, U.S. Pat. No. 8,507,205. In some embodiments of the method of the invention, a single kind of fusion product may be generated for each cell (or per reactor) or a plurality of different kinds of fusion products may be generated for each cell (or per reactor). Such plurality may be at least 2, or it may be in the range of from 2 to 500, or from 2 to 200, or from 2 to 100, or from 2 to 20. In one embodiment, such plurality may be in the range of from 2 to 10. In some embodiments, such plurality is two.

After completion of PCA reaction (1020), emulsion (1017) is broken and fusion products (1026) are isolated (1024). Fusion products (1026) are represented in FIG. 1E as conjugates of sequence tags (X, Y or Z) and recombined nucleic acids (e.g. clonotypes) ($C_1$, $C_2$ and $C_3$). A variety of conventional methods may be used to isolate fusion products (1026) from the reaction mixture, including, but not limited to, column chromatography, ethanol precipitation, affinity purification after use of biotinylated primers, gel electrophoresis, or the like. As part of PCA reaction (1020) or after isolation (1024), additional sequences may be added to fusion products (1026) as necessary for sequencing (1028). Sequencing may be carried out using a conventional high-throughput instrument, e.g. Genome Analyzer Ix (Illumina, Inc., San Diego), or the like.

Polymerase cycling assembly (PCA) reactions permit a plurality of nucleic acid fragments to be fused together to form a single fusion product in one or more cycles of fragment annealing and polymerase extension, e.g. Xiong et al, FEBS Micro biol. Rev., 32: 522-540 (2008). PCA reactions come in many formats. In one format of interest, PCA follows a plurality of polymerase chain reactions (PCRs) taking place in a common reaction volume, wherein each component PCR includes at least one linking primer that permits strands from the resulting amplicon to anneal to strands from another amplicon in the reaction and to be extended to form a fusion product or a precursor of a fusion product. PCA in its various formats (and under various alternative names) is a well-known method for fragment assembly and gene synthesis, several forms of which are disclosed in the following references: Yon et al, Nucleic Acids Research, 17: 4895 (1989); Chen et al, J. Am. Chem. Soc., 116: 8799-8800 (1994); Stemmer et al, Gene, 164: 49-53 (1995); Hoover et al, Nucleic Acids Research, 30: e43 (2002); Xiong et al, Biotechnology Advances, 26: 121-134 (2008); Xiong et al, FEBS Microbiol. Rev., 32: 522-540 (2008); and the like.

Figure 1F:
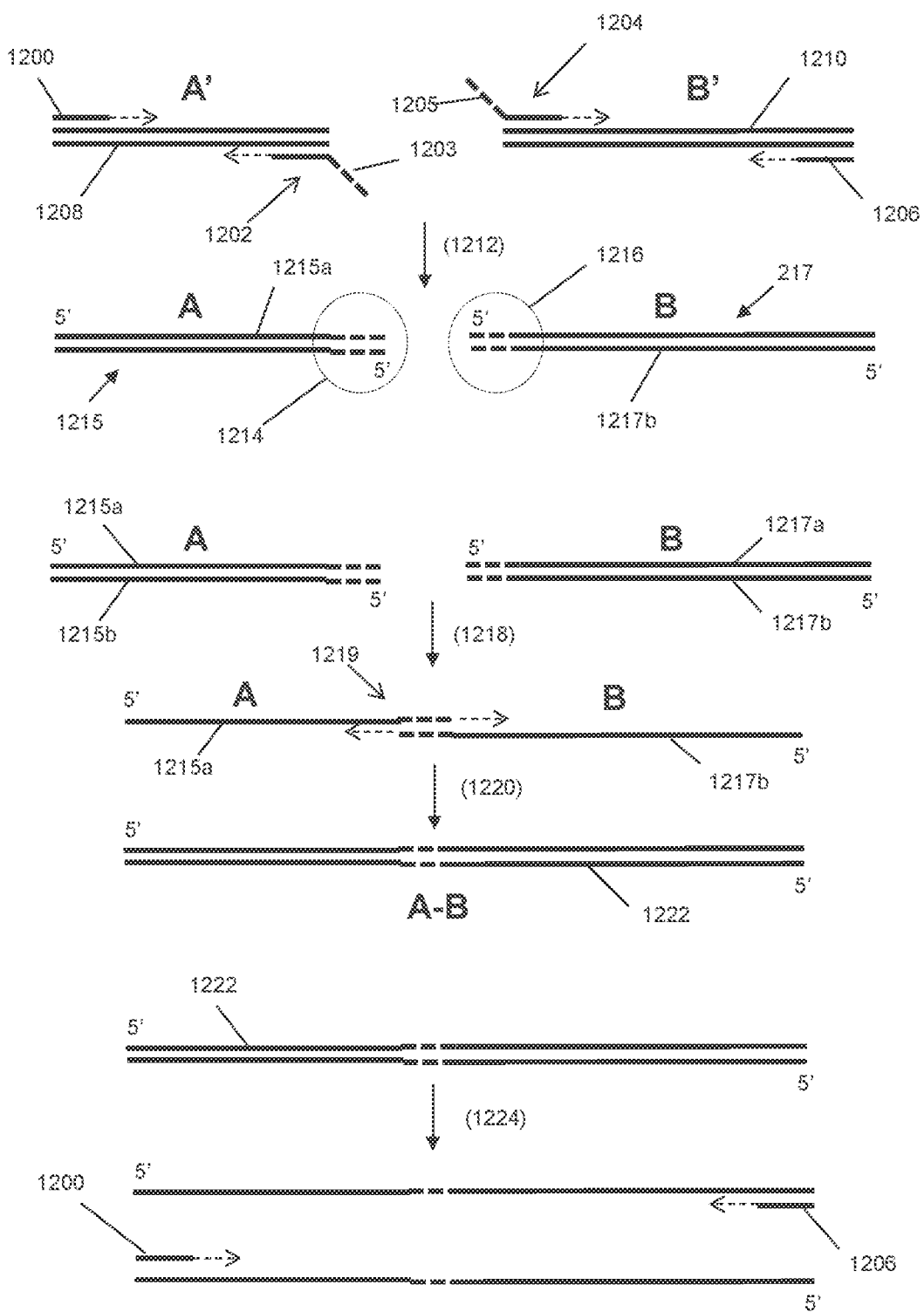
FIG. 1F illustrates a PCA scheme for linking target sequences where pairs of internal primers have complementary.

An exemplary (but not limiting) PCA format useful in the present embodiments is described in FIG. 1F, which illustrates a PCA scheme for joining two separate fragments A' (1208) and B' (1210) into a single fusion product (1222). Fragment A' (1208) is amplified with primers (1200) and (1202) and fragment B' (1210) is amplified with primers (1206) and (1204) in the same PCR mixture. Primers (1200) and (1206) are "outer" primers of the PCA reaction and primers (1202) and (1204) are the "inner" primers of the PCA reaction. Inner primers (1202) and (1204) each have a tail (1203 and 1205, respectively) that are not complementary to A' or B' (or adjacent sequences if A' and B' are segments imbedded in a longer sequence). Tails (1203) and (1205) are complementary to one another. Generally, such inner primer tails are selected for selective hybridization to its corresponding inner primer (and not elsewhere); but otherwise such tails may vary widely in length and sequence. In one aspect, such tails have a length in the range of from 8 to 30 nucleotides; or a length in the range of from 14 to 24 nucleotides. As the PCRs progress (1212), product fragments A (1215) and B (1217) are produced that incorporate tails (1203) and (1205) into end regions (1214) and (1216), respectively. During the PCRs product fragments A (1215) and B (1217) will denature and some of the "upper" strands (1215$a$) of A anneal (1218) to lower strands (1217$b$) of B and the 3' ends are extended (1219) to form (1220) fusion product A-B (1222). Fusion product A-B (1222) may be further amplified by an excess of outer primers (1200) and (1206). In some embodiments, the region of fusion product (1222) formed from tails (1203) and (1205) may include one or more primer binding sites for use in later analysis, such as high-throughput sequencing. Typically, in PCA reactions the concentrations of outer primers are greater than the concentrations of inner primers so that amplification of the fusion product continues after initial formation. For example, in one embodiment for fusing two target nucleic acids outer primer concentration may be from about 10 to 100 times that of the inner primers, e.g. 1 µM for outer primers and 0.01 µM for inner primers. Otherwise, a PCA reaction may comprise the components of a PCR.

Single Cell Analysis. As mentioned above, in some embodiments of the invention, cells from a population are disposed in reactors each containing a single cell. This may be accomplished by a variety of large-scale single-cell reactor platforms known in the art, e.g. Clarke et al, U.S. Patent Application Publication No. 2010/0255471; Mathies et al, U.S. patent publication 2010/0285975; Edd et al, U.S. Patent Application Publication No. 2010/0021984; Colston et al, U.S. Patent Application Publication No. 2010/0173394; Love et al, International Patent Publication No. WO 2009/145925; Muraguchi et al, U.S. Patent Application Publication No. 2009/0181859; Novak et al, Angew. Chem. Int. Ed., 50: 390-395 (2011); Chen et al, Biomed Microdevices, 11: 1223-1231 (2009); and the like, which are incorporated herein by reference. In one aspect, cells are disposed in wells of a microwell array where reactions, such as PCA reactions, take place; in another aspect, cells are disposed in micelles of a water-in-oil emulsion, where micelles serve as reactors. Micelle reactors generated by microfluidics devices, e.g. Mathies et al (cited above) or Edd et al (cited above), are of particular interest because uniform-sized micelles may be generated with lower shear and stress on cells than in bulk emulsification processes. Compositions and techniques for emulsifications, including carrying out amplification reactions, such as PCRs, in micelles is found in the following references, which are incorporated by reference: Becher, "Emulsions: Theory and Practice," (Oxford University Press, 2001); Griffiths and Tawfik, U.S. Pat. No. 6,489,103; Tawfik and Griffiths, Nature Biotechnology, 16: 652-656 (1998); Nakano et al, J. Biotechnology, 102: 117-124 (2003); Dressman et al, Proc. Natl. Acad. Sci., 100: 8817-8822 (2003); Dressman et al, U.S. Pat. No. 8,048,627; Berka et al, U.S. Pat. Nos. 7,842,457 and 8,012,690; Diehl et al, Nature Methods, 3: 551-559 (2006); Williams et al, Nature Methods, 3: 545-550 (2006); Zeng et al, Analytical Chemistry, 82(8): 3183-3190 (2010); Micellula DNA Emulsion & Purification Kit instructions (EURx, Gdansk, Poland, 2011); and the like. In one embodiment, the mixture of homogeneous sequence tags (e.g. beads) and reaction mixture is added dropwise into a spinning mixture of biocompatible oil (e.g., light mineral oil, Sigma) and allowed to emulsify. In another embodiment, the homogeneous sequence tags and reaction mixture are added dropwise into a cross-flow of biocompatible oil. The oil used may be supplemented with one or more biocompatible emulsion stabilizers. These emulsion stabilizers may include Atlox 4912, Span 80, and other recognized and commercially available suitable stabilizers. In some embodiments, the emulsion is heat stable to allow thermal cycling, e.g., to at least 94° C., at least 95° C., or at least 96° C. Preferably, the droplets formed range in size from about 5 microns to about 500 microns, more preferably from about 10 microns to about 350 microns, even more preferably from about 50 to 250 microns, and most preferably from about 100 microns to about 200 microns. Advantageously, cross-flow fluid mixing allows for control of the droplet formation, and uniformity of droplet size.

In some embodiments, micelles are produced having a uniform distribution of volumes so that reagents available in such reactors result in similarly amplified target nucleic acids and sequence tags. That is, widely varying reactor volumes, e.g. micelle volumes, may lead to amplification failures and/or widely varying degrees of amplification. Such failures and variation would preclude or increase the difficulty of making quantitative comparisons of target nucleic acids in individual cells of a population, e.g. differences in gene expression. In one aspect, micelles are produced that have a distribution of volumes with a coefficient of variation (CV) of thirty percent or less. In some embodiments, micelles have a distribution of volumes with a CV of twenty percent of less.

Cells of a tissue sample and antigen reagent may be suspended in a reaction mixture prior to disposition into reactors. In one aspect, a reaction mixture is a PCA reaction mixture and is substantially the same as a PCR reaction mixture with at least one pair of inner (or linking) primers and at least one pair of outer primers. In some embodiments, a step of lysing cells may be accomplished by heating cells to a temperature of 95° C. or above in the presence of a nonionic detergent, e.g. 0.1% Triton X-100 or Tween-20, for a period prior to carrying out an amplification reaction. In one embodiment, such period of elevated temperature may be from 10-20 minutes. Alternatively, a step of lysing cells may be accomplished by one or more cycles of heating and cooling, e.g. 96° C. for 15 min followed by 10° C. for 10 min, in the presence of a nonionic detergent, e.g. 0.1% Triton X-100 or Tween-20. Guidance for carrying out a lysing step is disclosed in Brown et al, J. R. Soc. Interface 5: S131-S138 (2008).

Clearly many microfluidics device configurations may be employed to generate micelles containing single cells, e.g. Zagoni et al, chapter 2, Methods of Cell Biology, 102: 25-48 (2011); Bronzes, chapter 10, Methods of Cell Biology, 102: 105-139 (2011); Wiklund et al, chapter 14, Methods of Cell Biology, 102: 177-196 (2011); Le Gac et al, chapter 7, Methods of Molecular Biology, 853: 65-82 (2012); and the like.

In some embodiments, this aspect of the invention for determining antigen-specific T cells may be implemented with the following steps: (a) exposing under interaction conditions a tissue sample containing T cells to antigen reagents labeled with sequence tags; (b) disposing in multiple reactors single T cells specifically bound to at least one antigen reagent, each reactor containing a polymerase cycling assembly (PCA) reaction mixture comprising a pair of outer primers and one or more pairs of linking primers, at least one pair of such outer and linking primers being specific for a recombined nucleic acid encoding a segment of a TCR chain of the T cell and one or more pairs of such outer and linking primers being specific for a sequence tag attached to the antigen reagent; (c) performing a PCA reaction in the reactors to form fusion products comprising said recombined nucleic acids and said sequence tag; (d) spatially isolating individual molecules of fusion products from the reactors; (e) sequencing the spatially isolated fusion products from the reactors to generate sequence reads from which pairs of clonotypes and sequence tags are determined; and (f) identifying antigen-specificity of T cells by their clonotype and sequence tag pairs. In some embodiments, the reactors are aqueous micelles of a water-in-oil emulsion. In some embodiments, aqueous micelles are generated by a microfluidics device. In some embodiments, the reactors are nanoliter wells in a planar substrate. In some embodiments, a further step of lysing the single T cells in the reactors is carried out prior to performing the PCA reaction.

Antigens

An antigen may be any compound or composition capable of eliciting a cell-mediated immune response (that is, an adaptive immune response), particularly in a mammal, such as a human. In some embodiments, an antigen may be any compound that can be recognized by a T cell in the context of the MHC molecule. More particularly, antigens include, but is not limited to, cells, tissue extracts, tissue or cell lysates, proteins, individually or as a mixture, a plurality of proteins, peptides, mixtures of peptides, lipids, carbohydrates, sugars, and the like. An antigen can be characteristic of a disease, such as an infectious disease, an autoimmune disease, or a cancer. The antigen can be, for example, a viral antigen, a bacterial antigen, a cancer antigen, etc. In some embodiments, an antigen is a cancer antigen or a viral antigen. By "cancer antigen" is meant any molecule (e.g., protein, peptide, lipid, carbohydrate, etc.) solely or predominantly expressed or over-expressed by a tumor cell or cancer cell, such that the antigen is associated with the tumor or cancer.

A cancer antigen may be a cancer antigen of only one type of cancer or tumor, such that the cancer antigen is associated with or characteristic of only one type of cancer or tumor. Alternatively, a cancer antigen may be a cancer antigen (e.g., may be characteristic) of more than one type of cancer or tumor. For example, a cancer antigen may be expressed by both breast and prostate cancer cells and not expressed at all by normal, non-tumor, or non-cancer cells, or expressed only minimally. A cancer antigen may a melanoma cancer antigen or a breast cancer antigen. Exemplary cancer antigens include those of the group consisting of gp100, MART-1, NY-ESO-1, a member of the MAGE family of proteins, e.g., MAGE-A1, mesothelin, Tyrosinase, TRP-1, TRP-2, PMSA, Her-2, and p53.

An antigen may be a viral antigen. In some embodiments, "viral antigen" means those antigens encoded by a part of a viral genome which can be detected by a specific immunological response. Viral antigens include, for example, a viral coat protein, an influenza viral antigen, an HIV antigen, a Hepatitis B antigen, or a Hepatitis C antigen.

An antigen can be naturally, artificially, synthetically, or recombinantly produced. Thus, an antigen can be a synthetic, recombinant, isolated, and/or purified protein, polypeptide, or peptide. Methods of making or obtaining such antigens are known in the art. For example, suitable methods of de novo synthesizing polypeptides and proteins (e.g., antigenic polypeptides and proteins) are described in Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwoood et al., Oxford University Press, Oxford, United Kingdom, 2000; and U.S. Pat. No. 5,449,752. Also, polypeptides and proteins (e.g., antigenic polypeptides and proteins) can be recombinantly produced using nucleic acids which encode the polypeptide or protein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. The nucleotide sequences of many antigens are known in the art and are available from the GenBank database of the National Center for Biotechnology Information (NCBI) website. Further, an antigen can be isolated and/or purified from a source, such as a plant, a bacterium, an insect, a mammal, e.g., a rat, a human, etc. Methods of isolation and purification are well-known in the art.

An antigen can be a free antigen, e.g., unbound antigenic peptide (e.g., a free peptide), or can be a bound antigen, e.g., an MHC-peptide tetramer or an antigenic peptide presented by a carrier cell which was pulsed with the peptide.

In some embodiments, peripheral blood mononuclear cells (PBMCs) (for example, which may be obtained from blood, for example, as a leukapheris product) from a subject may be cultured directly in the presence of antigen, to load antigen presenting cells (APCs) among the PBMCs with the antigen and to activate/stimulate antigen-specific T cells present in the PBMC. In this regard, PBMC may be collected from an individual, contacted with an antigen of interest, such as a tumor antigen, or a viral lysate, etc. In this manner, the APCs present in the PBMCs are loaded with the antigen, which is then presented to the T cells present in the sample. In some embodiments, antigen-specific T cells may be activated with peptide-MHC tetramers, see for example Altman, et al., Science 1998 Jun. 19; 280(5371):1821. In some embodiments, a protein antigen may be exposed to T cells indirectly by generating a set of peptides for binding to MHC molecules, where the sequences of the peptides are based on the amino acid sequence of the protein, e.g. Stickler et al, Toxicol. Sci., 77(2): 280-289 (2004). In some such embodiments, peptides are overlapping peptides covering the protein. In some embodiments, peptides each have a size of from 10 to 20 amino acids.

T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may be obtained from a single individual or a population of individuals, for example, a population of individual who all suffer from the same disease, such as, a cancer or an infectious disease.

In some embodiments, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis or leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Baxter) according to the manufacturer's instructions. After washing, the cells may be resuspended in a variety of biocompatible buffers, such as, for example, Ca++/Mg++ free PBS. Alternatively, the undesirable components of the apheresis sample may be removed and the cells directly resuspended in culture media.

In other embodiments, T cells are isolated from peripheral blood lymphocytes by lysing the red blood cells and by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, CD3+, CD28+ T cells can be positively selected using CD3/CD28 conjugated magnetic beads (e.g., DYNABEADS® M-450 CD3/CD28 T Cell Expander). In some embodiments, enrichment of a T cell population by negative selection can be accomplished with a combination of antibodies directed to surface markers unique to the negatively selected cells. One such method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Another method for preparing T cells for stimulation is to freeze the cells after the washing step, which does not require the monocyte-removal step. Wishing not to be bound by theory, the freeze and subsequent thaw step provides a more uniform product by removing granulocytes and, to some extent, monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

Uses of Reconstituted TCRs

Reconstituted T cell receptors have a variety of uses both individually and as a group, including, but not limited to, as binding compounds for immunotherapy, as components of transfected T cells for adoptive immunotherapy, as antigen sources in vaccines, and as indicators of immune status. Matched TCR chains in soluble format may be used as high affinity binding compounds linked to T cell capturing agents for unique anti-cancer therapeutics, e.g. as taught by Jakobsen et al, U.S. Pat. Nos. 7,329,731 and 7,666,604; which are incorporated herein by reference. Matched TCR chains may be used to construct vectors which may, in turn, be used to transfect autologous T cells for adoptive immunotherapy of a patient. In one embodiment of this application, samples from which TCRs are analyzed may be taken before and after a patient has been immunized with a cancer antigen, so that elevated anti-cancer TCR chains are readily matched and selected. References disclosing such applications include Turcotte et al, Adv. Surg., 45: 341-360 (2011); Morgan et al, Science, 314: 126-129 (2006); Walchli et al, PlosOne, 6: e27930 (2011); Robbins et al, U.S. patent publication 2010/0034834; and the like.

A population of matched or reconstituted TCRs from a sample comprises a unique profile of an individual's immune system, which contains much more information than profiles of single-sequence clonotypes. That is, a population of matched TCR chains or matched heavy and light chain immunoglobulins comprises a clonotype profile where the clonotypes are pairs of nucleotide sequences that encode pairs of TCR chains expressed in the same T cell or pairs of heavy and light chain immunoglobulins expressed in the same B cell. In both cases, such pairs may be related directly to T cell function, for example, by interaction with sets of MHC tetramer-peptide complexes, e.g. Palmowski et al, Immunol. Rev., 188: 155-163 (2002); Hadrup et al, Nature Methods, 6: 520-526 (2009), or to B cell function, for example, by ELISAs, e.g. Reddy et al, Nature Biotechnology, 28(9): 965-969 (2010). In one embodiment, clonotype profiles of matched immune receptor chains comprise at least 100 clonotype pairs, wherein each clonotype of the pair comprises a sequence of from 30 to 300 nucleotides. In another embodiment, clonotype profiles of matched immune receptor chains comprise at least 500 clonotype pairs, wherein each clonotype of the pair comprises a sequence of from 30 to 300 nucleotides. In another embodiment, clonotype profiles of matched immune receptor chains comprise at least 1000 clonotype pairs, wherein each clonotype of the pair comprises a sequence of from 30 to 300 nucleotides. In still another embodiment, such clonotype profiles of matched immune receptor chains comprise pairs of TCRα and TCRβ clonotypes. In another embodiment, such clonotype profiles of matched immune receptor chains comprise pairs of TCRγ and TCRδ clonotypes.

Samples

Samples, or tissue samples, of T-cells (T lymphocytes) may include, for example, helper T cells (effector T cells or Th cells), cytotoxic T cells (CTLs), memory T cells, and regulatory T cells, as well as other cell types normally found in a tissue sample. In one aspect, a sample of T cells includes at least 1,000 T cells; but more typically, a sample includes at least 10,000 T cells, and more typically, at least 100,000 T cells. In another aspect, a sample includes a number of T cells in the range of 1000 to 100,000 cells.

Samples used in the methods of the invention can come from a variety of tissues as noted above, including, for example, tumor tissue, blood and blood plasma, lymph fluid, cerebrospinal fluid surrounding the brain and the spinal cord, synovial fluid surrounding bone joints, and the like. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be a tumor biopsy. The biopsy can be from, for example, from a tumor of the brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

The sample can be a biopsy, e.g., a skin biopsy. The biopsy can be from, for example, brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

As discussed more fully below, in some embodiments, a sample of lymphocytes is sufficiently large so that substantially every T cell or B cell with a distinct clonotype is represented therein, thereby forming a repertoire (as the term is used herein). In some embodiments, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of T cells includes at least a half million cells, and in another embodiment such sample includes at least one million cells.

Blood samples are of particular interest and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 μL to 10 mL; in one aspect, blood sample volumes are in the range of from 200 μL to 2 mL. Optionally, subsets of white blood cells, e.g. lymphocytes, may be further isolated using conventional techniques, e.g. fluorescently activated cell sorting (FACS) (Becton Dickinson, San Jose, Calif.), magnetically activated cell sorting (MACS)(Miltenyi Biotec, Auburn, Calif.), or the like.

Since the identifying recombinations are present in the DNA of each individual's adaptive immunity cells as well as their associated RNA transcripts, either RNA or DNA can be sequenced in the methods of the provided invention. A recombined sequence from a T-cell encoding a T cell receptor molecule, or a portion thereof, is referred to as a clonotype. The DNA or RNA can correspond to sequences from T-cell receptor (TCR) genes. For example, the DNA and RNA can correspond to sequences encoding α, β, γ, or δ chains of a TCR. In a majority of T-cells, the TCR is a heterodimer consisting of an α-chain and β-chain. The TCRα chain is generated by VJ recombination, and the β chain receptor is generated by V(D)J recombination. For the TCRβ chain, in humans there are 48 V segments, 2 D segments, and 13 J segments. Several bases may be deleted and others added (called N and P nucleotides) at each of the two junctions. In a minority of T-cells, the TCRs consist of γ and δ delta chains. The TCR γ chain is generated by VJ recombination, and the TCR δ chain is generated by V(D)J recombination (Kenneth Murphy, Paul Travers, and Mark Walport, *Janeway's Immunology* 7th edition, Garland Science, 2007).

Amplification of Nucleic Acid Populations

Amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors, or portions thereof. Guidance for carrying out multiplex PCRs of such immune molecules is found in the following references, which are incorporated by reference: Faham and Willis, U.S. Pat. Nos. 8,236,503 and 8,628,927; Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 1544308B1; and the like.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al, Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego, Calif.); 50 μL final reaction volume; 100 ng sample DNA; 10 pmol of each primer (subject to adjustments to balance amplification as described below); dNTPs at 200 μM final concentration; $MgCl_2$ at 1.5 mM final concentration (subject to optimization depending on target sequences and polymerase); Taq polymerase (1-2 U/tube); cycling conditions: preactivation 7 min at 95° C.; annealing at 60° C.; cycling times: 30 s denaturation; 30 s annealing; 30 s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Real time PCR, picogreen staining, nanofluidic electrophoresis (e.g. LabChip) or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In one embodiment, amplification bias may be avoided by carrying out a two-stage amplification (as described in Faham and Willis, cited above) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100.000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has been carried out by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5\times10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths.

In one aspect, a sequence-based clonotype profile of an individual is obtained using the following steps: (a) obtaining a nucleic acid sample, for example, a sample containing T-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules to provide sequence reads; and (d) determining abundances of different sequences of the nucleic acid molecules from the nucleic acid sample to generate the clonotype profile. In some embodiments, the step of sequencing includes coalescing at least a plurality of sequence reads to form each clonotype. As described more fully below, such a step of coalescing is a process of combining sequence reads with error rates (for example, from sequencing and/or amplification errors) to produce clonotypes that are correct with a high degree of likelihood, such as with a 99% confidence level.

In one aspect, for each sample from an individual, the sequencing technique used in the methods of the invention generates sequences of least 1000 sequence reads per run; in another aspect, such technique generates sequences of at least 10,000 sequence reads per run; in another aspect, such technique generates sequences of at least 100,000 sequence reads per run; in another aspect, such technique generates sequences of at least 500,000 ssequence reads per run; and in another aspect, such technique generates sequences of at least 1,000,000 sequence reads per run. From such sequence reads clonotypes are determined, for example, as described below, or as disclosed in Faham and Willis (described above).

The sequencing techniques used in the methods generate sequence reads having lengths of at least 30 nucleotides. In some embodiments, a step of sequencing generates sequence reads having lengths of at least 50 nucleotides; and in some embodiments, a step of sequencing generates sequence reads having lengths of at least 100 nucleotides.

Clonotype Determination from Sequence Data

Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least $0.5$-$1.0\times10^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

In one aspect of the invention, sequences of clonotypes (including but not limited to those derived from TCRα, TCRβ, TCRγ, and/or TCRδ, may be determined by combining information from a plurality of sequence reads sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads).

Sequence reads of the invention may have a wide variety of lengths, depending in part on the sequencing technique being employed. For example, for some techniques, several trade-offs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 2 to 1000 sequence reads are generated for determining the sequence of each clonotype; in another embodiment, 2 to 100 sequence reads are generated for determining the sequence of each clonotype; and in another embodiment, 2 to 10 sequence reads are generated for determining the sequence of each clonotype; and in still another embodiment, at least 10 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads that in combination (but not separately) encompass a D and/or NDN region are sufficient.

In another aspect of the invention, sequences of clonotypes are determined in part by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (as mentioned above) are aligned to V and J region reference sequences, a tree search algorithm may be employed, e.g. as described generally in Gusfield (cited above) and Cormen et al, Introduction to Algorithms, Third Edition (The MIT Press, 2009).

Figure 3A:
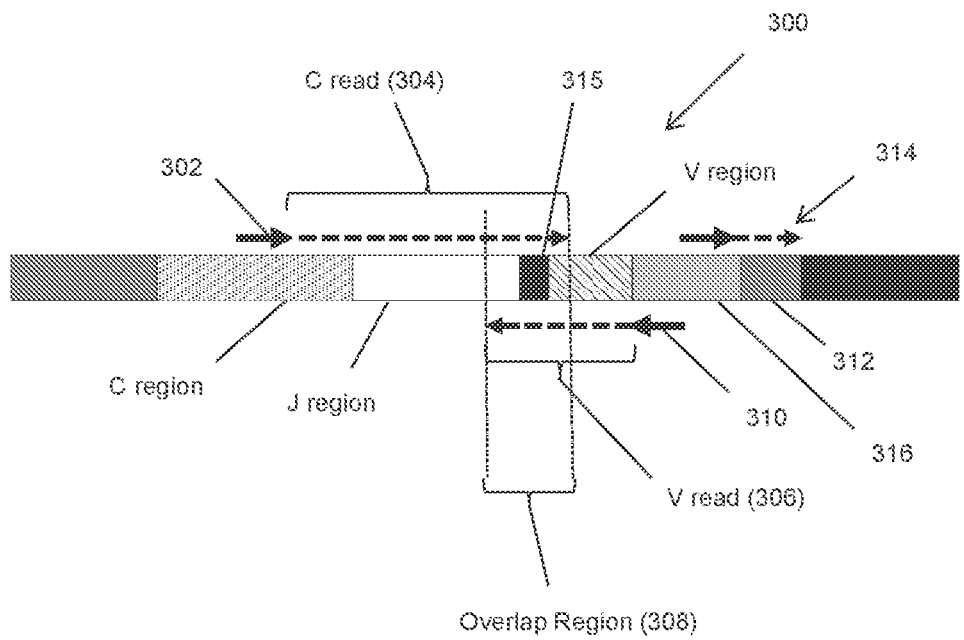
FIG. 3A illustrates details of determining a nucleotide sequence of the PCR product of FIG. 2C.
Figure 3B:
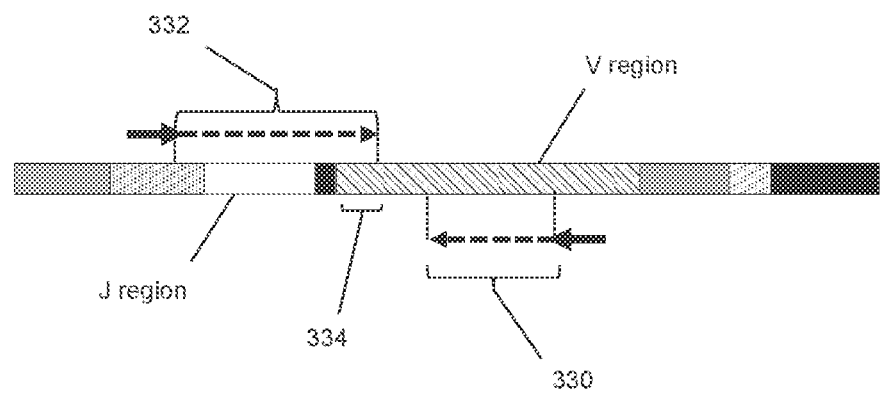
FIG. 3B illustrates details of another embodiment of determining a nucleotide sequence of the PCR product of FIG. 2C.

In another aspect, an end of at least one forward read and an end of at least one reverse read overlap in an overlap region (e.g. 308 in FIG. 3B), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCR β and IgH chains (illustrated in FIG. 3B) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 3B. Overlap region (308) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers, e.g. (302) and (310) in FIG. 3B, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCR β or IgH chain and includes a portion of the adjacent V region, e.g. as illustrated in FIGS. 3B and 3C. In one aspect, the overlap of the V read and the C read in the V region is used to align the reads with one another. In other embodiments, such alignment of sequence reads is not necessary, e.g. with TCRβ chains, so that a V read may only be long enough to identify the particular V region of a clonotype. This latter aspect is illustrated in FIG. 3C. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 3B, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

Reducing a set of reads for a given sample to a set of distinct clonotypes and recording the number of reads for each clonotype would be a trivial computational problem if sequencing technology was error free. However, in the presence of sequencing errors, each genuine clonotype is surrounded by a 'cloud' of reads with varying numbers of errors with respect to the its sequence. The "cloud" of sequencing errors drops off in density as the distance increases from the clonotype in sequence space. A variety of algorithms are available for converting sequence reads into clonotypes. In one approach, coalescing of sequence reads (that is, merging candidate clonotypes determined to have one or more sequencing errors) depends on at least three factors: the number of sequences obtained for each of the clonotypes being compared; the number of bases at which they differ; and the sequencing quality score at the positions at which they are discordant. A likelihood ratio may be constructed and assessed that is based on the expected error rates and binomial distribution of errors. For example, two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In one embodiment of the invention, the algorithm described below may be used for determining clonotypes from sequence reads. In one approach, sequence reads are first converted into candidate clonotypes. Such a conversion depends on the sequencing platform employed. For platforms that generate high Q score long sequence reads, the sequence read or a portion thereof may be taken directly as a candidate clonotype. For platforms that generate lower Q score shorter sequence reads, some alignment and assembly steps may be required for converting a set of related sequence reads into a candidate clonotype. For example, for Solexa-based platforms, in some embodiments, candidate clonotypes are generated from collections of paired reads from multiple clusters, e.g. 10 or more, as mentioned above.

The cloud of sequence reads surrounding each candidate clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given 'cloud' sequence Y with read count $C_2$ and E errors (with respect to sequence X) being part of a true clonotype sequence X with perfect read count $C_1$ under the null model that X is the only true clonotype in this region of sequence space. A decision is made whether or not to coalesce sequence Y into the clonotype X according the parameters $C_1$, $C_2$, and E. For any given $C_1$ and E a max value $C_2$ is pre-calculated for deciding to coalesce the sequence Y. The max values for $C_2$ are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above the threshold $C_2$ for coalescing into clonotype X then it becomes a candidate for seeding separate clonotypes (such as with candidate clonotype 2. An algorithm implementing such principles would also make sure that any other sequences Y2, Y3, etc. which are 'nearer' to this sequence Y (that had been deemed independent of X) are not aggregated into X. This concept of 'nearness' includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype if they happen to be 'near' more than one clonotype.

In some embodiments, an algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

As mentioned above, in another embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X. Successful implementation of the above algorithm for coalescing candidate clonotypes is dependent upon having an efficient way of finding all sequences with less than E errors (i.e. less than some sequence distance measure) from some input sequence X. One approach is using a sequence tree. The implementation of such trees has some unusual features in that the nodes of the tree are not restricted to being single letters of the DNA sequences of the candidate clonotypes. The nodes can have arbitrarily long sequences, which allows for a more efficient use of computer memory.

For example, all of the reads of a given sample are placed into the sequence tree. Each leaf nodes holds pointers to its associated reads. A unique sequence of a candidate clonotype is retrieved by traversing backwards in the tree from the leaf to the root node. The first sequence is placed into a simple tree with one root node and one leaf node that contains the full sequence of the read. Sequences are next added one by one. For each added sequence either anew branch is formed at the last point of common sequence between the read and the existing tree or add the read to an existing leaf node if the tree already contains the sequence. Having placed all the reads into the tree it is easy to use the tree for the following purposes: 1) Finding the highest read count: sorting leaf nodes by read count allows one to find the leaf node (i.e. sequence) with the most reads, and successively lower numbers of reads; 2) Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

TCRβ Repertoire Analysis

In this example, TCRβ chains are analyzed and clonotypes are determined. The analysis includes amplification, sequencing, and analyzing the TCRβ sequences. One primer is complementary to a common sequence in Cβ1 and Cβ2, and there are 34 V primers capable of amplifying all 48 V segments. Cβ1 or Cβ2 differ from each other at position 10 and 14 from the J/C junction. The primer for Cβ1 and Cβ2 ends at position 16 bp and has no preference for Cβ1 or Cβ2. The 34 V primers are modified from an original set of primers disclosed in Van Dongen et al, U.S. patent publication 2006/0234234, which is incorporated herein by reference. The modified primers are disclosed in Faham et al, U.S. patent publication 2010/0151471, which is also incorporated herein by reference.

The Illumina Genome Analyzer is used to sequence the amplicon produced by the above primers. A two-stage amplification is performed on messenger RNA transcripts (200), as illustrated in FIGS. 2A-2B, the first stage employing the above primers and a second stage to add common primers for bridge amplification and sequencing. As shown in FIG. 2A, a primary PCR is performed using on one side a 20 bp primer (202) whose 3' end is 16 bases from the J/C junction (204) and which is perfectly complementary to Cβ1 (203) and the two alleles of Cβ2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having primer binding site (218)

specific for P7 primers (220). After a conventional multiplex PCR, amplicon (216) is formed that contains the highly diverse portion of the J(D)V region (206, 208, and 210) of the mRNA transcripts and common primer binding sites (203 and 218) for a secondary amplification to add a sample tag (221) and primers (220 and 222) for cluster formation by bridge PCR. In the secondary PCR, on the same side of the template, a primer (222 in FIG. 2B and referred to herein as "C10-17-P5") is used that has at its 3'end the sequence of the 10 bases closest to the J/C junction, followed by 17 bp with the sequence of positions 15-31 from the JC junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 front the J/C junction. The looping of positions 11-14 eliminates differential amplification of templates carrying Cβ1 or Cβ2. Sequencing is then done with a primer complementary to the sequence of the 10 bases closest to the J/C junction and bases at positions 15-31 from the J/C junction (this primer is called C'). C10-17-P5 primer can be HPLC purified in order to ensure that all the amplified material has intact ends that can be efficiently utilized in the cluster formation.)

In FIG. 2A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that all amplified.

As illustrated in FIG. 2A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification primer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer, C-10-17-P5 (222, FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Figure 2C:
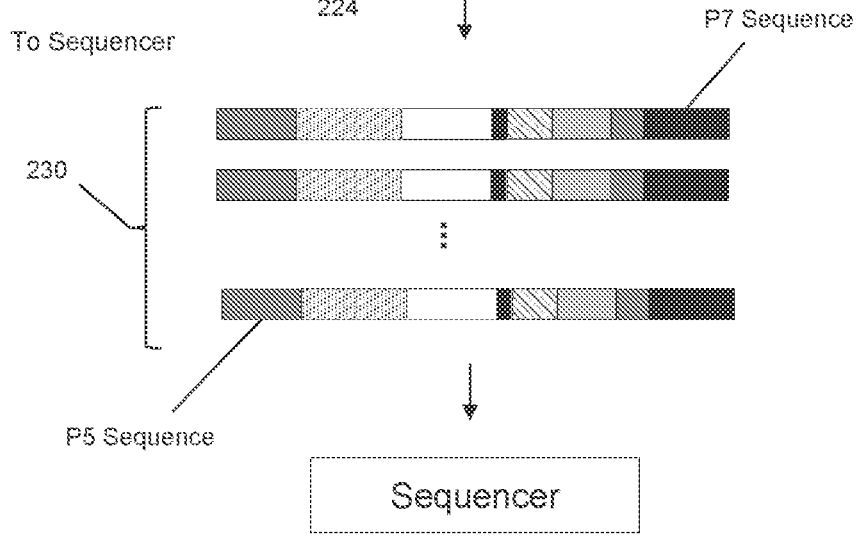

Amplicon (230) resulting from the 2-stage amplification illustrated in FIGS. 2A-2C has the structure typically used with the Illumina sequencer as shown in FIG. 2C. Two primers that anneal to the outmost part of the molecule, Illumina primers P5 and P7 are used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using a tag primer provided by the manufacturer (Illumina). The final read is the Read 2 primer, also provided by the manufacturer (Illumina). Using this primer, a 100 bp read in the V segment is generated starting with the 1st PCR V primer sequence.

EXAMPLES

In this example steps common to some embodiments, such as the embodiment of FIG. 1C, are described for particular applications, including but not limited to, exposing a tissue sample comprising T cells to antigen, activating T cell in a tissue sample by antigen, obtaining recombined nucleic acids from T cells of a tissue sample, isolating (or recovering, or sorting, or separating) activated T cells, sequencing recombined nucleic acids, forming clonotypes, and determining clonotypes of antigen-specific T cells.

Tissue Samples. Characterized PBMCs were purchased from Cellular Technology Limited. Cells were thawed, washed and either lysed with RLT plus buffer (Qiagen) for nucleic acid purification or cultured overnight in the presence of peptides (see below) to identify antigen-specific T cells.

Antigen-Specific T Cell Assavs, Flow Cytometry and Cell Sorting. Antigen-specific cells were identified using a variety of assays: pentamer binding, cell surface marker upregulation (CD137, CD107) following short-term peptide incubation, and proliferation following relatively long-term peptide incubation. Pentamer-specific T cells were identified by incubating PBMCs with HCMV pp65$_{495-504}$ Pentamer (ProImmune) according to manufacturer's instructions. The procedures for obtaining viable antigen-specific T cells based on acquisition of the cell surface markers CD137/107 (for CD8 antigen-specific T cells) following brief in vitro incubation with peptides are well-known, e.g. Chattopadhyay et al, Nature Medicine, 11: 1113-1117 (2005); Meier et al, Cytometry A, 73: 1035-1042 (2008); Wolfl et al, Blood, 110: 201-210 (2007); Wolfl et al, Cytometry A, 73: 1043-1049 (2008); and the like. Briefly, complete media containing 15% Fetal Bovine Serum (FBS), non-essential amino acids, glutamine and antibiotics was used for peptide incubations. Thawed PBMCs were washed and suspended at ~400,000 cells per well (96-well i-bottom plates) in complete media. Unconjugated antibodies directed against CD28 and CD49d were then added to the wells containing the suspended cells. Peptides derived from CMV pp65 (HCMVA (pp65) (JPT Peptide Technologies) were added directly to the cell/antibody mixture, according to manufacturer's instructions. A single peptide derived from CMV pp65 (sequence NLVPMVATV; herein referred to as 'pp65$_{495}$') was used at 2 µg/ml. pp65 'PepMix" and CEF+ peptide pools (JPT Peptide Technologies) were added directly to the cell/antibody mixture, according to manufacturer's instructions. Following addition of peptides, cells were incubated at 37° C. for ~18 hours. Negative control incubations were prepared as outlined above without addition of peptides. At the end of the incubation, cells were harvested from the culture and stained with antibodies for analysis and sorting by flow cytometry. For each CD8 antigen-specific assay (CD137 and CD107), fluorescently conjugated antibodies to the following cell surface markers were used for flow cytometry: CD8, CD3 and either CD137 or CD107a and CD107b. Cells were then washed and suspended in PBS containing FBS (2%) and 4',6-diamidino-2-phenylindole (DAPI) for exclusion of non-viable cells. Carboxyfluorescein diacetate, succinimidyl ester (CFSE)-labeled PBMCs were incubated as outlined above for 6 days in the presence of peptide and antibodies directed against CD28 and CD49d. Antigen-specific CD8+ T cells were identified and sorted based on CFSE dilution at day 6. Cells were acquired and sorted using a FACSAria (BD Biosciences) instrument. Sorted antigen-specific (CD3+CD8+CMVpentamer+, CD3+CD8+CD137+, CD3+CD8+CD107a/b+, or CD8+CFSE$^{low}$) and non-antigen-specific (CD3+CD8+CD137−, CD3+CD8+CD107a/b−) cells were pelleted and lysed in RLT Plus buffer for nucleic acid isolation. Analysis of flow cytometry data files was performed using FlowJo (Ashland, OR).

RNA and cDNA Preparation. RNA (and DNA) was isolated using AllPrep DNA/RNA mini and/or micro kits, according to manufacturer's instructions (Qiagen). RNA was reverse transcribed to cDNA using Vilo kits (Life Technologies).

TCRβ Amplification and Sequencing. cDNA was amplified using locus specific primer sets for TCRβ. This amplification reaction reproducibly amplified all possible RNA transcripts found in the sample containing the rearranged TCRβ locus regardless of which variable (V) segment and which common constant (C) region allele each rearranged molecule possessed, while appending the necessary sequences for cluster formation and sample indexing.

First stage primers were designed so as to allow for the amplification of all known alleles of the germline sequences, as described above and in the following; Faham et al, Blood, 120: 5173-5180 (2012). At the 5' ends of the V segment primers, universal sequences complementary to second stage PCR primers were appended. Primers were optimized such that each possible V and C segment was amplified at a similar rate so as to minimally skew the repertoire frequency distribution during the amplification process. Specificity of the primers was, in contrast, not optimized as the primer sequences could be mapped and removed from the eventual sequence read. Thus a given sequence may have been amplified by multiple primers.

In the second stage PCR, primers on the C side annealed to the C segment with a 5' tail that contained the sequence primer and the P5 sequence used for cluster formation in the Illumina Genome Analyzer sequencer. Primers on the V side annealed to the V segment with a 5' tail that contained the sequence primer and the P7 sequence used for cluster formation. For each sample, one pair of primers is used in the second stage. On the C side, it is always the same primer. On the V side, it is one of a set of primers which differs by a 6 base index. Specifically, the primers on the V side of the amplification constituted one of a set of primers, each of which had a 3' region that annealed to the overhang sequence appended in the first reaction but which further contained one of multiple 6 base pair indices that allowed for sample multiplexing on the sequencer. Each of these primers further contained a 5' tail with the P7 sequence used for cluster formation in the Illumina Genome Analyzer sequencer.

First stage PCR was carried out using a high fidelity polymerase (AccuPrime, Life Technologies) for 16 cycles. A second stage PCR was carried out for 22 cycles on 1/100 of the amplification products from the first stage PCR. Each sample contained a unique identifying tag. Samples were pooled and purified using the QIAquick PCR purification kit (Qiagen). Cluster formation and sequencing in both directions was carried out per the manufacturer protocol (Illumina, Inc., La Jolla, Calif.). Specifically, three sequencing reactions were performed. First 115 bp were sequenced from the C side sufficient to sequence through the junctional sequence from C to V. At this point, the synthesized strand was denatured and washed off A second sequencing primer was annealed that allowed the sample index to be sequenced for 6 cycles to identify the sample. At this point the reverse complement strand was generated per the Illumina protocol. A final sequencing read of 95 bp was obtained from the V-to-C direction providing ample sequence to map the V segment accurately. The sequencing data was then analyzed to determine the clonotype sequences, as described above.

Clonotype Determination. A clonotype was defined when at least 2 identical sequence reads were obtained. Briefly, after exclusion of low quality reads, sequence data were then analyzed to determine the clonotype sequences including mapping to germline V and J consensus sequences. First, the sample index sequences were used to identify which of the sequences originate from which of the pooled samples. Sequences whose index were not a perfect match to one of the indices used in a specific run were excluded. Next the forward read was used to map the J segment. Since all the sequences started from the same position of the J segments, all the J segments started at a predefined sequencing position. The first 25 bp of the J segments were used to map the J segment. Any read with more than 5 high quality mismatches to the known J segments was excluded from further analysis.

After J segment identification, V segments were mapped. The reverse read was used for this purpose. First, the V primer was mapped and excluded. Thereafter, the next 70 bases of the reverse read were mapped to the known V segments. Reads that did not map to J and V segments were excluded. The next step in mapping involved identifying the frame that related the forward and reverse reads and this allowed a continuous sequence from J to V to be constructed. This was done using the last 15 bases of the forward read which were reliably within the V segment regardless of NDN length. While these bases could be of relatively lower sequence quality as they were at the terminal end of a long read, they could be used to map within a single identified V segment in order to identify the position at which the two reads could be joined. Finally, the known V and J sequences to which the reads map were used to identify the point in the forward read at which the sequences at the junctions diverged from these mapped segments.

Following clonotype determination, relative frequencies of the clonotypes were analyzed in the unsorted, antigen-specific and non-antigen-specific populations. Clonotype frequency comparisons between two samples are shown in several figures. Clonotypes that are present in sample A but not in sample B (where frequencies in sample A and B are being compared) are represented to have the frequency of a clonotype with a single read in sample B. Therefore the frequency of the missing clonotype in a sample depends on the sequencing depth of a particular sample. In these cases where a clonotype is missing in a sample, because the frequency of a single read is assigned to these clonotypes, the observed frequency is overestimated. Thus, in the vast majority of these cases, the real clonotype frequency is likely to be overestimated. Clonotypes absent in both samples appear where the axes intersect. Clonotypes present in one sample but not the other however lie along either the x- or y-axis.

Clonotypes from the antigen-specific T cell analyses were selected based on the following three criteria. First, clonotypes had frequencies that were at least 10-fold increased in sorted antigen-specific versus non-antigen-specific or unsorted cells, e.g. FIG. 6 panels A and B. Second, these clonotypes were also at lower frequency in sorted "not antigen-specific" cells compared to unsorted cells if greater than 1/100,000 in order to avoid sub-sampling error (Poisson noise) associated with very low frequency clonotypes in sorted samples. Third, because of the limited number of input antigen-specific cells after sorting (generally less than <30,000 cells), a greater than '20-cell' equivalent threshold was applied based on the relatively low input number of cells in these samples. This minimum threshold enabled exclusion of clonotypes that appeared enriched in sorted antigen-specific samples but were due only to the presence of one or a few cells in the sample. For example, consider a sorted population of 10,000 pentamer+ cells out of a sample with a million T cells. If a single cell with a frequency of 1 per million in the unsorted sample is incidentally sorted in the pentamer+ sample, its frequency in the sorted sample will be 1/10,000 and would appear to be 100 fold enriched in the pentamer+ sample compared to the unsorted sample. To ameliorate this problem, a clonotype was required to represent 20 cells in the sorted pentamer+ sample. Specifically, the log 10 frequency threshold required in the pentamer+ sample was calculated as log 10(1/(n/20)), where n is the number of input sorted cells for that sample as determined by flow cytometry (For example, in FIG. 7 panel A, 16,281 is number of input sorted cells and the calculated threshold frequency is 10-2.9). Those sequences meeting the three criteria outlined above were classified as antigen-specific T cell clonotypes.

Results. The combination of sorting and sequencing was used to identify antigen-specific clonotypes in an individual with a known positive response to a cytomegalovirus (CMV) antigen. First, TCRβ sequencing was paired with a multimer-based immune assay to validate this method for identification of antigen-specific CD8 TCRβ clonotypes. A peptide derived from CMV pp65(495-404) (referred to herein as the "pp65495 peptide") is an HLA-A*0201 restricted immunodominant epitope that induces responses in CMV-positive individuals. To directly identify T cells specific to this antigen, a commercially available pentamer reagent containing pp65495 peptide bound to an MHC molecule was used. In principle, all of the T cells carrying the sequences that bind the pentamer should be detected irrespective of their functional potential. pp65495-specific CD8 T cells were identified by sequencing the TCRβ repertoire of cells that were sorted based on pentamer binding (pentamer+).

Frozen PBMCs were obtained from an individual with a characterized response to pp65495 by ELISPOT assay. Two populations were sorted from this individual: CD8 pentamer+ and pentamer− T cells. Nucleic acids encoding TCRβ clonotypes were sequenced in these two populations along with the unsorted PBMC sample, so that the relative frequencies of the clonotypes in each population could be determined. Three criteria were used to identify pp65495-specific TCRβ clonotypes: 1) Clonotypes that are enriched (i.e. have substantially higher frequency) in the pentamer+ population compared to the pentamer− population; 2) Clonotypes that are enriched in the pentamer+ population compared to the unsorted sample; and 3) Clonotypes that are de-enriched (i.e. have lower frequency) in the pentamer− population compared to the unsorted sample.

Figure 6A:
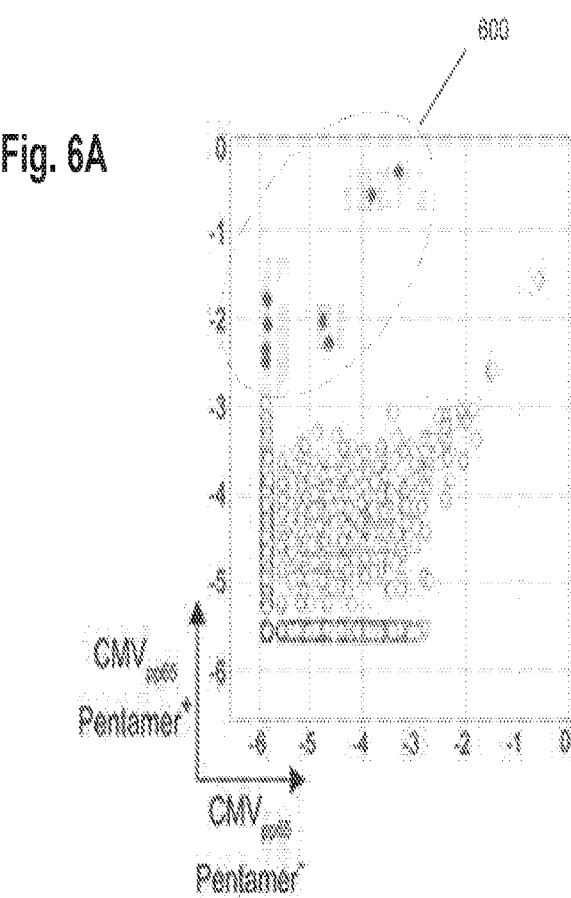
FIG. 6A-FIG. 6B show data for identification of CMV pp65$_{495}$-specific T cell clonotypes from sorted pentamer+ T cells.
Figure 6B:
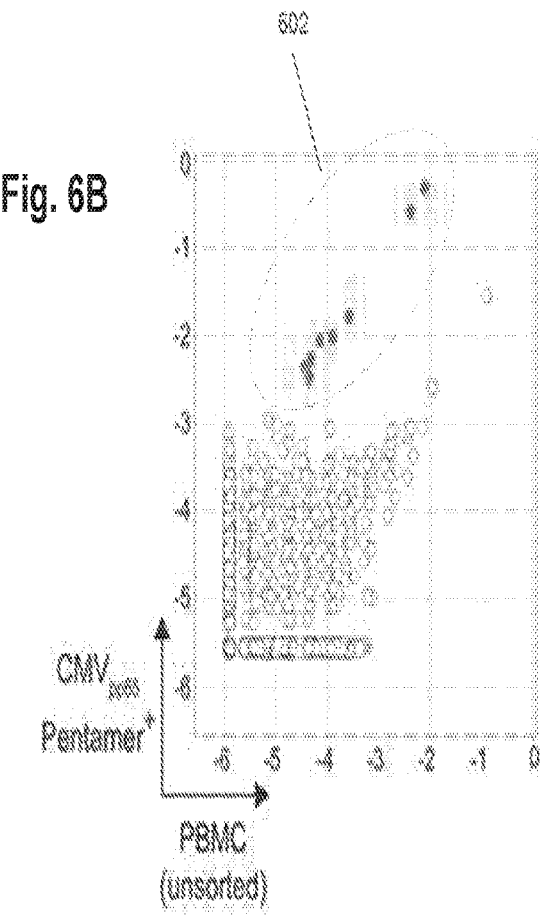
Figure 9A:
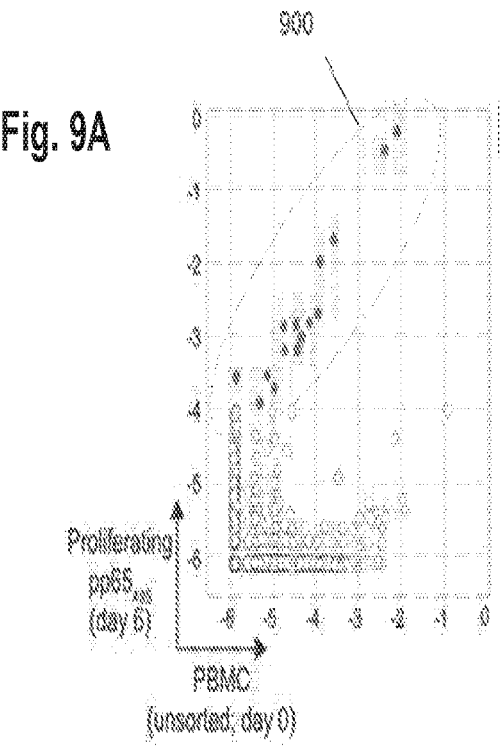
FIG. 9A-FIG. 9D shows data for identification of low-frequency CMV pp65495-specific T cell clonotypes following peptide incubation and proliferation.
Figure 9B:
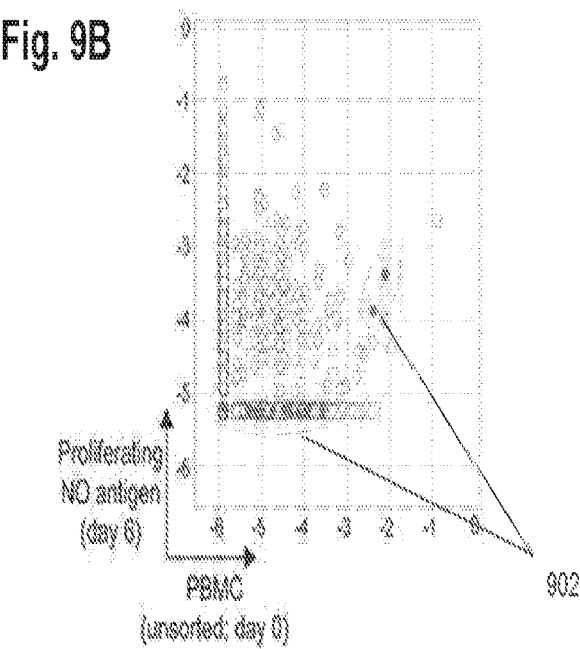
Figure 9C:
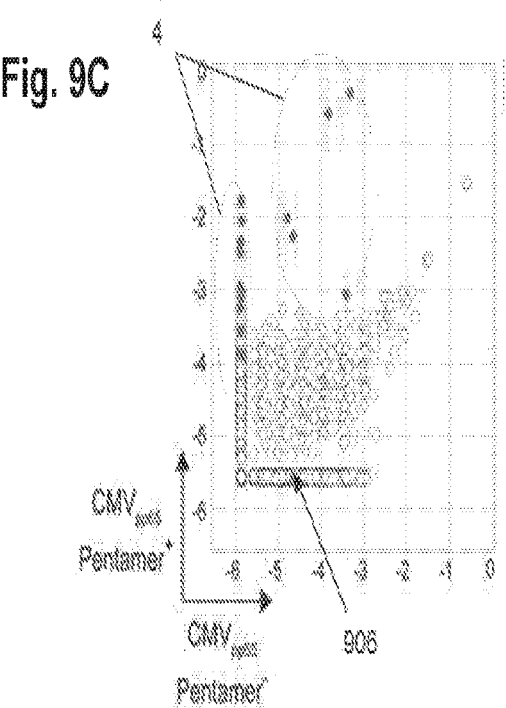
Figure 9D:
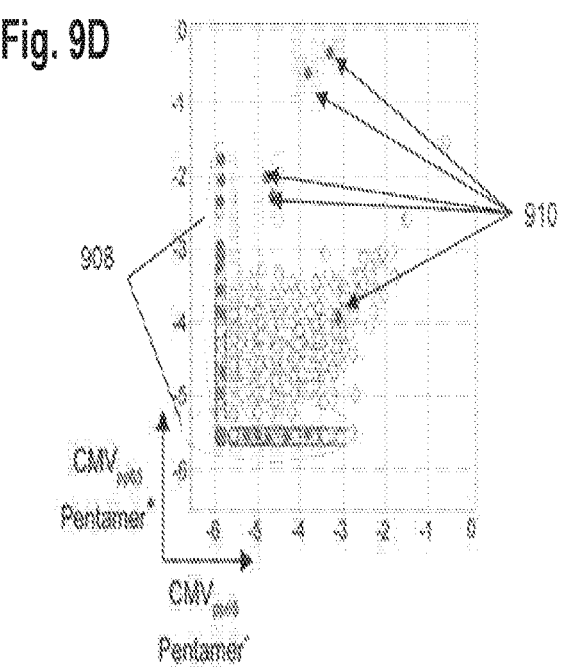

Eight clonotypes were identified that are substantially enriched (~1,000 fold) in the pentamer+ compared to the pentamer− population (FIG. 6 panel A). The frequencies of these clonotypes were compared in the pentamer+ and the unsorted populations (FIG. 6 panel B). The highest of these clonotypes has a frequency of 0.81% in the unsorted sample, which is consistent with the expected elevated response to $pp65_{495}$ in this individual. However, several of the other clonotypes were present at a level below $10^{-4}$. The 8 clonotypes are enriched in the pentamer+ population by a factor of ~100 fold compared to their frequency in unsorted PBMC.

PBMCs from the same individual were used to assess whether immune assays that rely on indirect or functional changes in the T cells following antigen stimulation are effective for identification of $pp65_{495}$-specific CD8 TCRβ clonotypes. PBMCs were stimulated with $pp65_{495}$ followed by flow cytometry 18 hours after the stimulation to capture cells based on expression of the activation marker CD137. The TCRβ repertoire was amplified and sequenced from sorted CD137+ and CD137− cells. The criteria for identification of $pp65_{495}$-specific TCRβ clonotypes with this assay was similar to that used in the pentamer assay. Specifically, $pp65_{495}$-specific TCRβ clonotypes were expected to be present at much higher frequencies in the CD137+ population compared to the CD137− population.

Nine clonotypes were identified that are substantially enriched (~1,000 fold) in the CD137+ population compared to the CD137− population (FIG. 7 panel A). The frequency of these clonotypes in the unsorted sample ranged from as high as 0.81% to as low as 0.004% (FIG. 7 panel B). These clonotypes were enriched in the CD137+ population compared to the unsorted PBMC sample by ~100 fold. To ensure that these cells were activated due to stimulation with the peptide, a control experiment was performed with no peptide. None of the 9 clonotypes that were enriched with the peptide in the CD137+ population enriched following incubation without peptide in CD137+ cells (FIG. 7 panel C).

Specific clonotypes identified by the pentamer and CD137 assays were compared and found to substantially overlap. All 8 clonotypes that were identified with the pentamer assay were also identified by CD137 assay (FIG. 8 panel A), although an additional clonotype was identified by the CD137 assay that was not identified in the pentamer assay.

A third functional assay for identification of antigen-specific clonotypes was conducted by combining capture of proliferating cells following incubation with $pp65_{495}$ peptide and repertoire sequencing. Cells were labeled with CFSE and incubated with either $pp65_{495}$ or no peptide for 6 days. Proliferating CD8 cells were then sorted based on dilution of CFSE. $pp65_{495}$-specific clonotypes were identified based on their relative frequency in the $CFSE_{low}$ population compared to that of fresh unsorted PBMCs.

Sixteen clonotypes were identified that were substantially increased in the $CFSE^{low}$ population, and the frequency of some of the identified clonotypes was below $10^{-5}$ (FIG. 9 panel A). An identical proliferation assay was used that lacked the peptide as a control. None of the 16 clonotypes identified by the proliferation assay were enriched in the $CFSE_{low}$ population when no peptide was used (FIG. 9 panel B).

One advantage to using indirect immune monitoring assays compared to pentamer reagents is the ability to assess responses to more than one peptide antigen at the same time. A pool of 138 peptides spanning the entire pp65 protein (herein referred to as pp65pool) was used to stimulate PBMCs in the proliferation assay to identify pp65pool-specific T cells. Repertoire analysis of proliferating cells following pp65pool incubation enabled identification of 25 clonotypes. Of these 25 clonotypes identified using the pp65pool, 12 of these were also deemed antigen-specific with the single pp65$_{495}$ peptide, demonstrating the repeatability of the approach.

Seven of eight clonotypes identified by the pentamer assay were identified in the pp65pool proliferation assay, demonstrating that the use of peptide pool does not substantially decrease sensitivity. In addition the proliferation assay with the pp65pool enabled identification of additional clonotypes that are presumably specific to other peptides within the pool. Most of the additional clonotypes identified with the pp65pool were not enriched in the pentamer+ population (FIG. 9 panel D) consistent with them being not specific to the pp65$_{495}$ peptide.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Komberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6$^{th}$ edition (Saunders, 2007).

"Activation" or "immune activation" or "activated", especially in reference to T-cells, means a phase of an adaptive immune response that follows the antigen recognition phase (during which antigen-specific lymphocytes bind to antigens) and is characterized by proliferation of lymphocytes and their differentiation into effector cells, e.g. Abbas et al, Cellular and Molecular Immunology, Fourth Edition, (W.B. Saunders Company, 2000). Activation of T cells may be associated with secretion of certain cytokines that are detectable using conventional assays, such as an ELISPOT assay, and may be associated with the expression of characteristic cell surface markers, such as CD25, CD134, CD69, CD137, CD154, or the like, e.g. Gratama et al, Cytometry A, 73A: 971-974 (2008).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonotype" means a recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR 3, a DJ rearrangement of TCR β, a VJ rearrangement of TCR α, a VJ rearrangement of TCR γ, a VDJ rearrangement of TCR δ, a VD rearrangement of TCR δ, a Kde-V rearrangement, or the like. Clonotypes may also encode translocation breakpoint regions involving immune receptor genes, such as Bcl1-IgH or Bcl1-IgH. In one aspect, clonotypes have sequences that are sufficiently long to represent or reflect the diversity of the immune molecules that they are derived from; consequently, clonotypes may vary widely in length. In some embodiments, clonotypes have lengths in the range of from 25 to 400 nucleotides; in other embodiments, clonotypes have lengths in the range of from 25 to 200 nucleotides.

"Clonotype profile" means a listing of distinct clonotypes and their relative abundances that are derived from a population of lymphocytes. Typically, the population of lymphocytes are obtained from a tissue sample. The term "clonotype profile" is related to, but more general than, the immunology concept of immune "repertoire" as described in references, such as the following: Arstila et al, Science, 286: 958-961 (1999); Yassai et al, Immunogenetics, 61: 493-502 (2009); Kedzierska et al, Mol. Immunol., 45(3): 607-618

(2008); and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes; in other embodiments, clonotype profiles may comprise at least $10^4$ distinct clonotypes; in other embodiments, clonotype profiles may comprise at least $10^5$ distinct clonotypes; in other embodiments, clonotype profiles may comprise at least $10^6$ distinct clonotypes. In such embodiments, such clonotype profiles may further comprise abundances or relative frequencies of each of the distinct clonotypes.

In one aspect, a clonotype profile is a set of distinct recombined nucleotide sequences (with their abundances) that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (i.e. the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR β chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a clonotype profile comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$.

In a particular embodiment, a clonotype profile of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a clonotype profile of the invention comprises a set of nucleotide sequences that encodes substantially all segments of the V(D)J region of a TCR β chain. In another embodiment, a clonotype profile of the invention comprises a set of nucleotide sequences having lengths in the range of from 25-200 nucleotides and including segments of the V, D, and J regions of a TCR β chain. In another embodiment, a clonotype profile of the invention comprises a set of nucleotide sequences having lengths in the range of from 25-200 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR β chain. In still another embodiment, "substantially equivalent" means that with ninety-nine percent probability a clonotype profile will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. In some embodiments, clonotype profiles are derived from samples comprising from $10^3$ to $10^7$ lymphocytes. Such numbers of lymphocytes may be obtained from peripheral blood samples of from 1-10 mL.

"Coalescing" means treating two candidate clonotypes with sequence differences as the same by determining that such differences are due to experimental or measurement error and not due to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Data structure" means an organization of information, usually in a computer or memory device, for better algorithm efficiency. Exemplary data structures include queues, stacks, linked lists, heaps, hash tables, arrays, trees, and the like. Data structures may have substructures that correspond to units of information or to subsets of related information. For example, arrays have rows and columns of entries; trees have nodes, branches, subtrees, and leaves; or the like. In one aspect, a data structure used herein is a sequence tree, an array or a hash table.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003

"Percent homologous," "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, WI), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, WI). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred µL, e.g. 200 µL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("tagman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, 02-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymerase cycling assembly" or "PCA" reaction (also referred to herein as "linked PCR") means a PCR that comprises at least one pair of outer primers and at least one pair of inner primers. An inner primer has a 3' portion that is complementary to a target nucleic acid (or its complement) and a 5' portion that is complementary to the 5' portion of another inner primer corresponding to a different target nucleic acid.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Quality score" means a measure of the probability that abase assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Sequence read" means a sequence of nucleotides determined from a sequence or stream of data generated by a sequencing technique, which determination is made, for example, by means of base-calling software associated with the technique, e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tag" (or "tag") or "barcode" means an oligonucleotide that is attached, usually via a covalent bond, to another molecule or molecular complex and that is used to identify and/or track the other molecule in a reaction or a series of reactions. Sequence tags may vary widely in size and compositions; the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g. via a hybridization reaction or via an enzymatic reaction, such as amplification and sequencing; whether they are labeled, e.g. with a fluorescent dye or the like; the number of distinguishable sequence tags required to unambiguously identify a set of molecules of interest, and the like, and how different must tags of a set be in order to ensure reliable identification, e.g. freedom from cross hybridization, misidentification from sequencing errors, or the like. In some embodiments, sequence tags may each have a length within a range of from 6 to 36 nucleotides, or from 4 to 30 nucleotides, or from 8 to 40 nucleotides, or from 6 to 50 nucleotides, respectively; provided, however, that the term "sequence tag" may also be used in reference to a sequence tag of the foregoing lengths sandwiched between a pair of primers that may be used to amplify or otherwise manipulate the sequence tag, for example, in order to identify it by DNA sequencing. In one aspect, sets of sequence tags are used wherein each sequence tag of a set has a unique nucleotide sequence that differs from that of every other tag of the same set by a plurality of bases; in some embodiments, such plurality is at least three bases; in another aspect, sets of sequence tags are used wherein the sequence of each tag of a set differs front that of every other tag of the same set by at least four bases.

"Sequence tree" means a tree data structure for representing nucleotide sequences. In one aspect, a tree data structure of the invention is a rooted directed tree comprising nodes and edges that do not include cycles, or cyclical pathways. Edges from nodes of tree data structures of the invention are usually ordered. Nodes and/or edges are structures that may contain, or be associated with, a value. Each node in a tree has zero or more child nodes, which by convention are shown below it in the tree. A node that has a child is called the child's parent node. A node has at most one parent. Nodes that do not have any children are called leaf nodes. The topmost node in a tree is called the root node. Being the topmost node, the root node will not have parents. It is the node at which operations on the tree commonly begin (although some algorithms begin with the leaf nodes and work up ending at the root). All other nodes can be reached from it by following edges or links.

The invention claimed is:

1. A method for identifying clonotypes of antigen-specific T cells in a sample comprising T cells, wherein each clonotype comprises the nucleotide sequences of a TCRα segment and a TCRβ segment that are a pair of sequences specific to a T cell, the method comprising the steps of:
   (a) exposing the sample to a plurality of antigens in a plurality of different reaction mixtures, wherein each antigen of said plurality of antigens is present in a predetermined unique subplurality of the plurality of reaction mixtures;
(b) selecting antigen-specific T cells from each of the plurality of reaction mixtures;
(c) sequencing nucleic acids encoding the TCRα segment and the TCRβ segment from:
   (i) the antigen-specific T cells selected in step (b) from each of the plurality of reaction mixtures, wherein the sequencing produces a plurality of sequence reads for each reaction mixture from which clonotypes and clonotype frequencies are determined, and
   (ii) T cells obtained from the sample prior to step (a), wherein the sequencing produces a plurality of sequence reads from which clonotypes and clonotype frequencies are determined;
(d) for each reaction mixture, comparing the clonotype frequencies determined in step (c) (i) with the clonotype frequencies determined in step (c) (ii); and
(e) for each of the plurality of antigens, identifying a clonotype of an antigen-specific T cell that has an increased frequency in each of the reaction mixtures in which the antigen was present and does not have an increased frequency in each of the reaction mixtures in which the antigen was absent.

2. The method of claim 1, wherein the sample comprises at least 1000 T cells.

3. The method of claim 2, wherein the sequencing is performed by high-throughput sequencing.

4. The method of claim 3, wherein the high-throughput sequencing comprises a step of spatially isolating individual molecules of the nucleic acids on a solid surface and sequencing the isolated individual molecules in parallel to provide the sequence reads.

5. The method of claim 3, wherein the plurality of antigens comprises a plurality of proteins or a plurality of peptides.

6. The method of claim 5, wherein the antigen-specific T cells are selected based on interaction with an antigen in the reaction mixture.

7. The method of claim 6, wherein the T cells in the sample are from a population of individuals.

8. The method of claim 1, wherein the sequencing is performed by high-throughput sequencing.

9. The method of claim 8, wherein the high-throughput sequencing comprises a step of spatially isolating individual molecules of the nucleic acids on a solid surface and sequencing the isolated individual molecules in parallel to provide the sequence reads.

10. The method of claim 1, wherein the plurality of antigens comprises a plurality of proteins or a plurality of peptides.

11. The method of claim 1, wherein the antigen-specific T cells are selected based on interaction with an antigen in the reaction mixture.

12. The method of claim 1, wherein the T cells in the sample are from a population of individuals.

13. The method of claim 1, wherein the sample is a tissue sample.

14. The method of claim 13, wherein the tissue sample is a blood sample or a sample of peripheral blood mononuclear cells derived from peripheral blood.

15. The method of claim 13, wherein the plurality of antigens are presented by gene-modified cells expressing the antigens.

16. The method of claim 14, wherein the plurality of antigens are presented by gene-modified cells expressing the antigens.

17. A method of producing a patient-specific immunotherapeutic reagent comprising:
   (a) identifying clonotypes of antigen-specific T cells in a sample comprising T cells, wherein each clonotype comprises the nucleotide sequences of a TCRα segment and a TCRβ segment that are a pair of sequences specific to a T cell, and wherein the method comprises the steps of claim 1; and
   (b) producing a patient-specific immunotherapeutic reagent comprising a TCRα segment and a TCRβ segment that are encoded by one of the clonotypes identified in step (a).

18. The method of claim 17, wherein the patient-specific immunotherapeutic reagent is a reconstituted T cell.

19. The method of claim 17, wherein the patient has cancer and wherein the antigen-specific T cells are cancer antigen-specific T cells.

* * * * *